(12) United States Patent
Khashaba

(10) Patent No.: US 11,373,296 B1
(45) Date of Patent: Jun. 28, 2022

(54) SYSTEM AND METHOD FOR ANALYSIS OF CHIP AND BURR FORMATION IN DRILLED FIBER REINFORCED PLASTIC COMPOSITES USING IMAGE PROCESSING

(71) Applicant: King Abdulaziz University, Jeddah (SA)

(72) Inventor: Usama Abdelmoneim Ali Khashaba, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 17/677,347

(22) Filed: Feb. 22, 2022

(51) Int. Cl.
| | |
|---|---|
| *G01N 3/08* | (2006.01) |
| *G01N 3/26* | (2006.01) |
| *G01N 3/28* | (2006.01) |
| *G01N 3/24* | (2006.01) |
| *G06T 7/00* | (2017.01) |
| *G06T 7/194* | (2017.01) |
| *G01N 23/2251* | (2018.01) |
| *G01N 3/06* | (2006.01) |
| *B23B 49/00* | (2006.01) |

(Continued)

(52) U.S. Cl.
CPC .............. *G06T 7/001* (2013.01); *B23B 49/00* (2013.01); *B29C 65/48* (2013.01); *B29C 66/02242* (2013.01); *B29C 66/721* (2013.01); *B29C 66/7422* (2013.01); *C23C 14/02* (2013.01); *C23C 14/20* (2013.01); *C23C 14/24* (2013.01); *G01N 3/066* (2013.01); *G01N 3/08* (2013.01); *G01N 3/24* (2013.01); *G01N 23/2251* (2013.01); *G06T 7/194* (2017.01); *G06T 7/62* (2017.01); *G01N 2203/0017* (2013.01); *G01N 2203/0025* (2013.01); *G01N 2203/04* (2013.01); *G01N 2203/0617* (2013.01); *G01N 2223/07* (2013.01); *G01N 2223/418* (2013.01); *G01N 2223/507* (2013.01); *G06T 2207/10061* (2013.01)

(58) Field of Classification Search
CPC combination set(s) only.
See application file for complete search history.

(56) References Cited

U.S. PATENT DOCUMENTS

2021/0148213 A1\* 5/2021 Madasu ................ E21B 49/003

FOREIGN PATENT DOCUMENTS

| CN | 105738382 A | \* | 7/2016 |
| CN | 105738382 A | | 7/2016 |

(Continued)

*Primary Examiner* — Brandi N Hopkins
(74) *Attorney, Agent, or Firm* — Oblon, McClelland, Maier & Neustadt, L.L.P.

(57) ABSTRACT

A system and a method for measuring drilling damage in fiber reinforced plastic (FRP) composites is described. Multiple holes are drilled in the FRP composite using a drill having nominal diameter, and the FRP composite is separated into multiple drilled blocks. Each block, covered with the black substrate, is scanned on a scanner to generate a scanned image depicting a hole region, a background, and delamination damage peaks. For each scanned image, a maximum delamination damage peak and a maximum diameter of a first circle concentric with the drilled hole and passing through tip of the maximum delamination peak, are measured. Further, a delamination size and a delamination factor are calculated based on the maximum diameter of the first circle and the nominal diameter of the drill.

20 Claims, 43 Drawing Sheets

(51) Int. Cl.
*C23C 14/20* (2006.01)
*C23C 14/02* (2006.01)
*C23C 14/24* (2006.01)
*B29C 65/48* (2006.01)
*B29C 65/00* (2006.01)
*G06T 7/62* (2017.01)

(56) References Cited

FOREIGN PATENT DOCUMENTS

| | | | |
|---|---|---|---|
| CN | 105138842 B | 12/2017 | |
| CN | 106940318 B | 4/2019 | |
| CN | 111832209 A | 10/2020 | |
| WO | WO-2014157570 A1 * | 10/2014 | ............. B23B 35/00 |

* cited by examiner

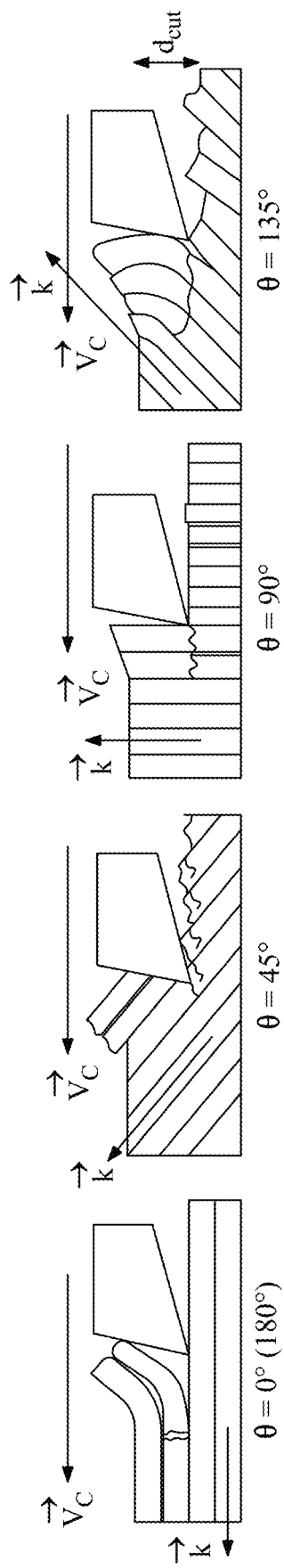

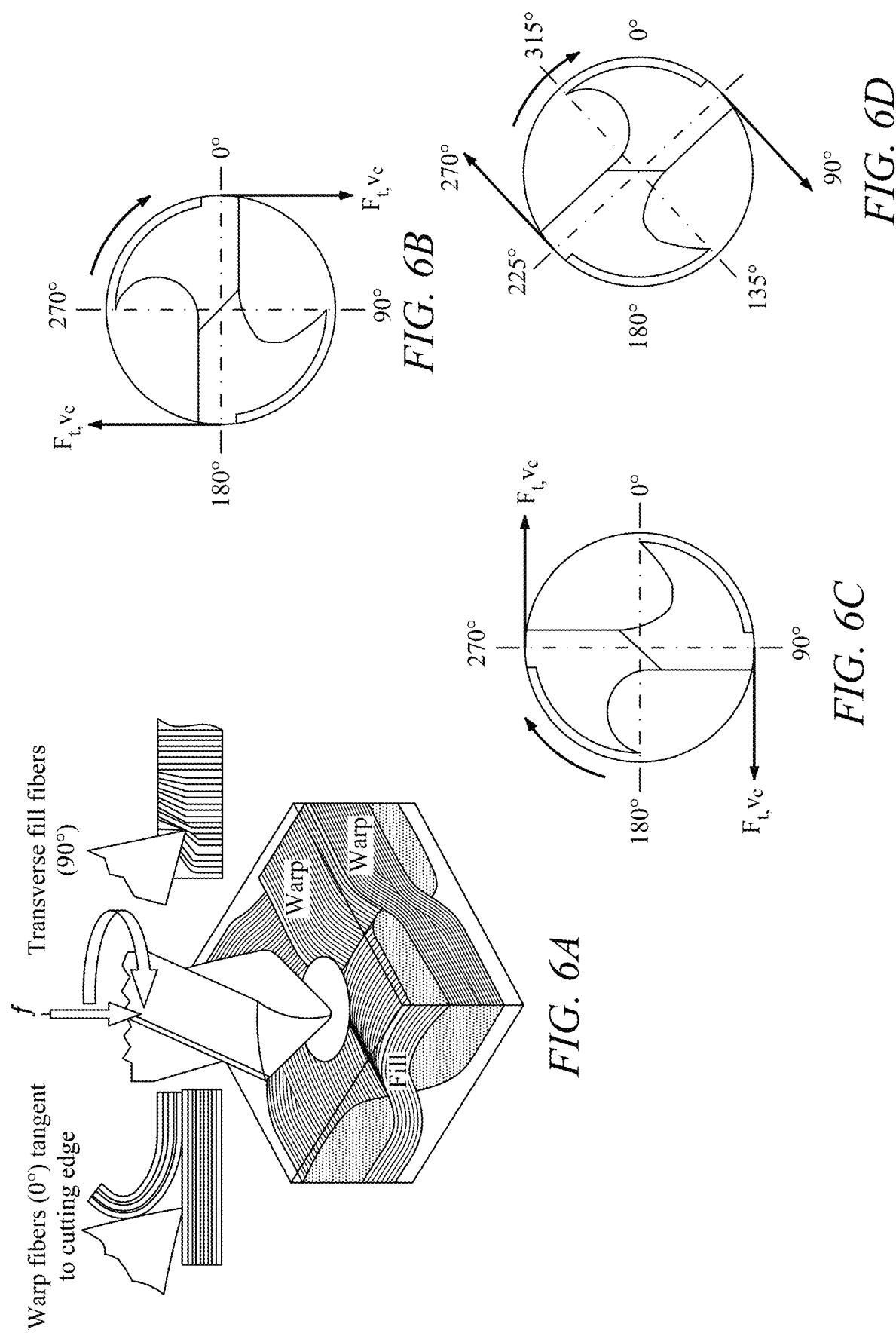

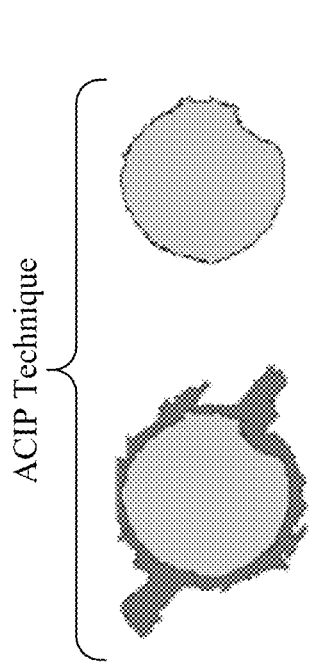
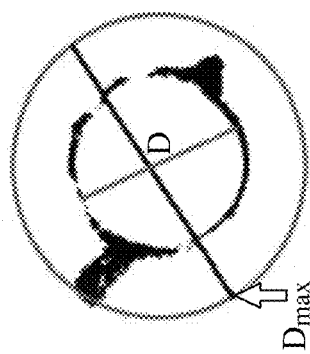
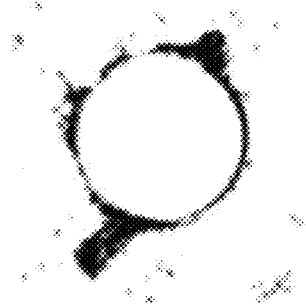
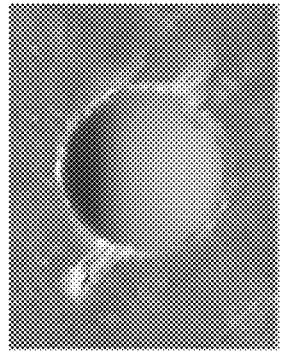
FIG. 13
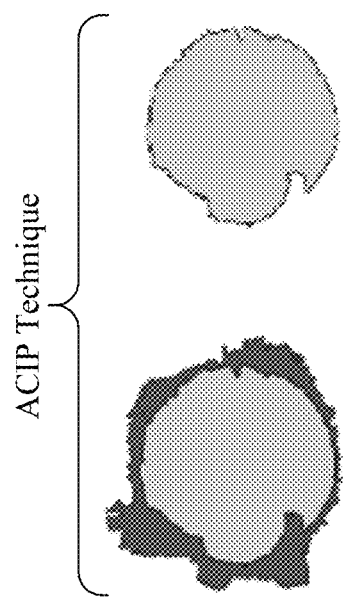
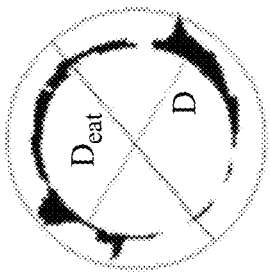
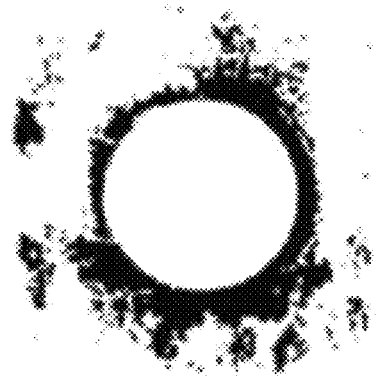
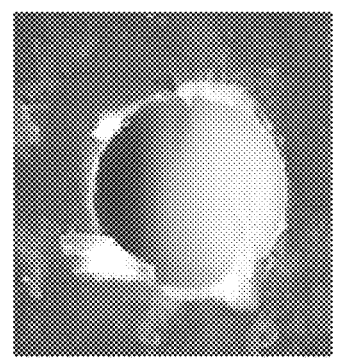
FIG. 14

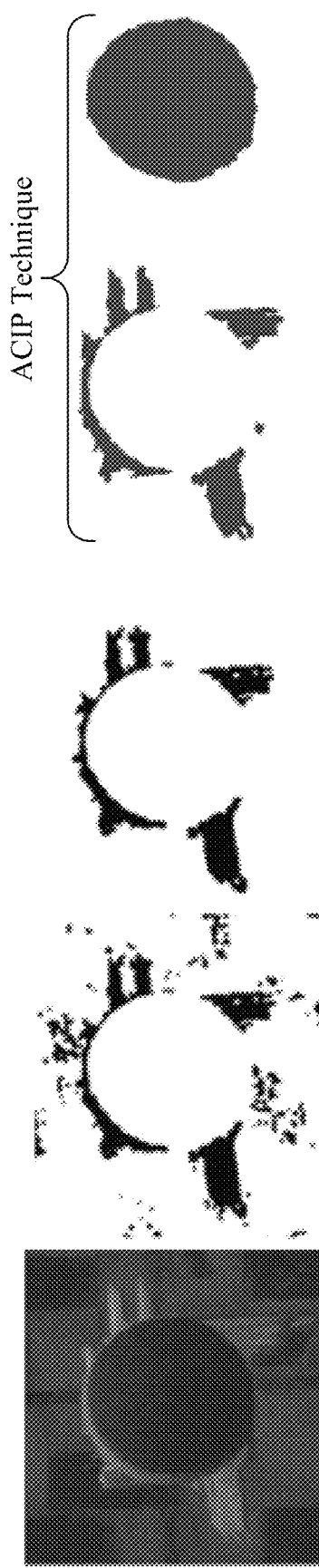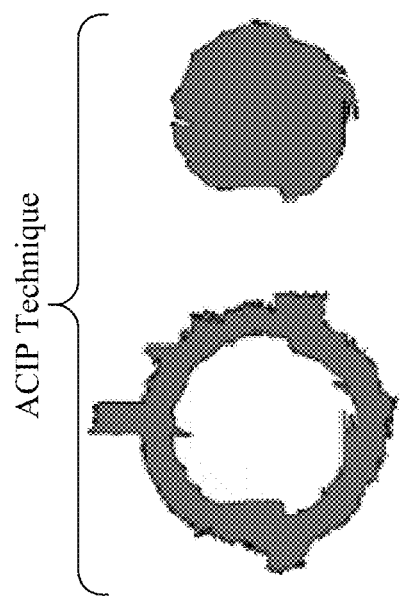
FIG. 15
FIG. 16

| | (a) Peel-up Delamination | | | | | | | | |
|---|---|---|---|---|---|---|---|---|---|
| Feed (mm/r) | Specimen image | Image of $A_p$-$A_h$ | Image of $A_h$ | $D_{max}$ (mm) | $D_{min}$ (mm) | $A_p$ (mm$^2$) | $A_h$ (mm$^2$) | $A_d$ (mm$^2$) | $A_b$ (mm$^2$) |
| 0.05 | | | | 14.095 | 14.095 | 113.717 | 72.733 | 35.178 | 5.807 |
| 0.1 | | | | 15.142 | 14.053 | 114.371 | 71.599 | 35.831 | 6.941 |
| 0.15 | | | | 15.505 | 14.720 | 116.353 | 74.830 | 37.813 | 3.710 |
| 0.23 | | | | 16.097 | 15.303 | 120.187 | 77.500 | 41.647 | 1.040 |

FIG. 18

| (b) Push-out Delamination | | | | | | | | |
|---|---|---|---|---|---|---|---|---|
| 0.05 | 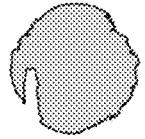 |  |  | 15.882 | 15.090 | 110.317 | 71.088 | 31.777 | 7.452 |
| 0.1 | 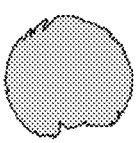 | 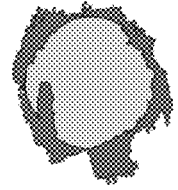 |  | 16.093 | 15.348 | 127.164 | 50.230 | 48.624 | 28.310 |
| 0.15 | 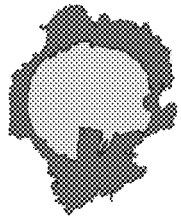 | 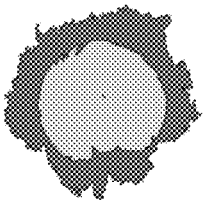 | 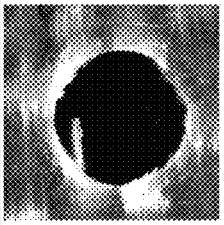 | 16.988 | 16.453 | 129.976 | 62.501 | 51.436 | 16.039 |
| 0.23 | 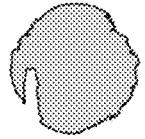 |  |  | 17.000 | 16.081 | 142.858 | 71.109 | 64.318 | 7.431 |
FIG. 18 (Cont'd)

| Feed (mm/r) | Specimen image | Image of $A_p$-$A_h$ | Image of $A_h$ | $D_{max}$ (mm) | $D_{min}$ (mm) | $A_p$ (mm²) | $A_h$ (mm²) | $A_d$ (mm²) | $A_b$ (mm²) |
|---|---|---|---|---|---|---|---|---|---|
| | | | (a) Peel-up Delamination | | | | | | |
| 0.05 | | | | 15.032 | 14.693 | 116.896 | 74.951 | 38.356 | 3.589 |
| 0.1 | | | | 15.833 | 15.455 | 118.019 | 74.670 | 39.479 | 3.870 |
| 0.15 | | | | 15.337 | 15.337 | 131.075 | 70.091 | 52.535 | 8.449 |
| 0.23 | | | | 16.353 | 16.312 | 139.829 | 76.784 | 61.289 | 1.756 |

FIG. 19

(b) Push-out Delamination

| | | | | | | | | |
|---|---|---|---|---|---|---|---|---|
| 0.05 | | | 15.814 | 15.814 | 126.424 | 61.395 | 47.884 | 17.145 |
| 0.1 | | | 16.228 | 15.663 | 130.325 | 52.601 | 51.785 | 25.939 |
| 0.15 | | | 16.142 | 15.778 | 140.933 | 53.113 | 62.393 | 25.426 |
| 0.23 | | | 17.883 | 17.423 | 164.377 | 57.298 | 85.838 | 21.242 |

FIG. 19 (Cont'd)

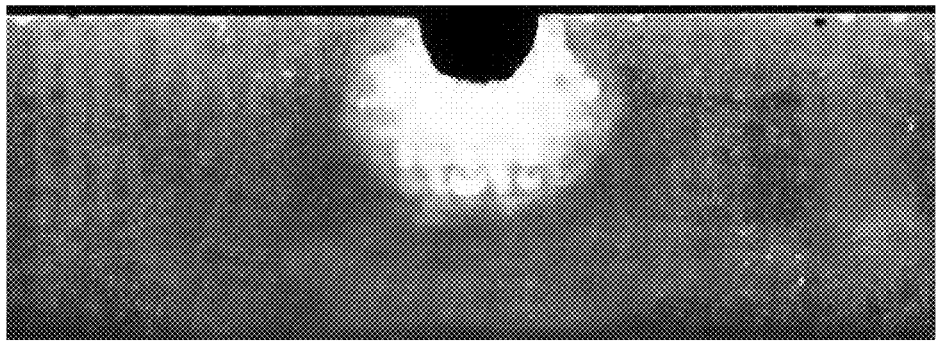
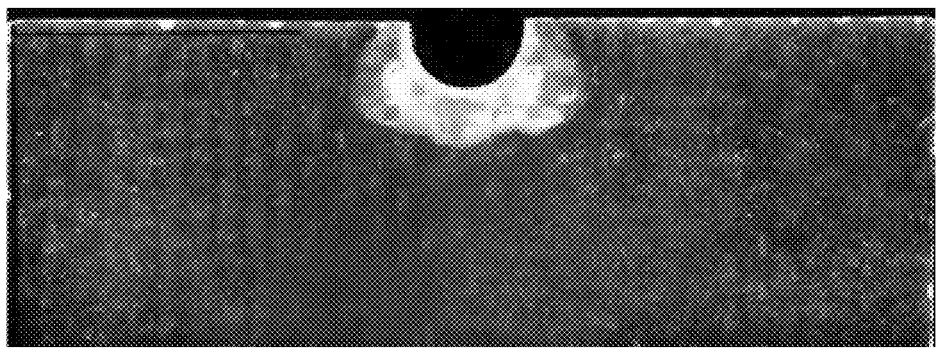
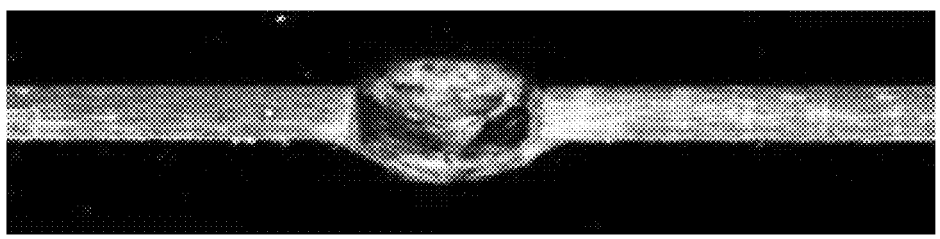
FIG. 25C

SYSTEM AND METHOD FOR ANALYSIS OF CHIP AND BURR FORMATION IN DRILLED FIBER REINFORCED PLASTIC COMPOSITES USING IMAGE PROCESSING

STATEMENT OF ACKNOWLEDGEMENT

The inventors acknowledge the financial support provided by the Deputyship for Research & Innovation, Ministry of Education in Saudi Arabia through project number 2021-098 and by King Abdulaziz University, DSR, Jeddah, Saudi Arabia.

BACKGROUND

Technical Field

The present disclosure is directed to system and method for measuring drilling damage in fiber reinforced plastic composites.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Mechanical drilling with a drill bit is commonly used for drilling holes for riveted and bolted joints during assembly operations. However, defects and damages, such as delamination, burr, microcracking, swelling, splintering and fiber pullout, may be visible after drilling. Delaminations formed at the entry and the exit planes of the workpiece are critical defects, resulting in decreased bearing strength. Additional manufacturing operations must be performed to repair and increase the service life of the workpiece under fatigue loads.

Many solutions have been developed to determine drilling damages caused to the workpiece during the entry and exit of the drill, for example CN111832209A describes a progressive failure analysis of a composite material laminated plate structure under stress using an electron microscope; CN105138842B describes carbon fiber composite material drilling damage characterization using an acoustic microscope; CN106940318B describes a fiber reinforced composite material processing effect evaluation method using a three dimensional acoustic microscope, each incorporated by reference in their entirety. However, the characterization of drilling damage in the aforementioned patents uses expensive equipment and time consuming procedures which are not automatic. Additionally, the above references fail to realize quantization of the burr and delamination damages.

Accordingly, it is one object of the present disclosure to provide a system and methods to automatically characterize chip and burr formation in fiber reinforced plastic composites due to drilling.

SUMMARY

In an exemplary embodiment, a method for measuring drilling damage in fiber reinforced plastic composites is disclosed. The method includes drilling a plurality of holes in a fiber reinforced plastic composite with a drill having a nominal diameter, $D_{nom}$; separating, with a cutting tool, the fiber reinforced plastic composite into a plurality of drilled blocks, each drilled block including one drilled hole; covering each drilled block with a black substrate; scanning, with a scanner, each drilled block covered with the black substrate on the scanner, thus generating a scanned image of each drilled hole, the scanned image depicting a hole region, delamination damage peaks radiating from the hole region and a background. For each scanned image, the method includes measuring, with a computing device, a maximum delamination damage peak and a maximum diameter $D_{max}$ of a first circle concentric with a center of each drilled hole, where the maximum diameter $D_{max}$ extends through the center to a tip of the maximum delamination damage peak. The method further includes calculating, with the computing device, a delamination size, $S_d$, and a delamination factor, $F_d$, of each drilled block.

In another exemplary embodiment, a system for measuring drilling damage in fiber reinforced plastic composites is disclosed. The system includes a plurality of blocks, each block having a drilled hole; a plurality of black substrates, each black substrate covering a side of a block over the drilled hole; a scanner configured to scan the side of each block covered by the black substrate and generate a scanned image, wherein the scanned image depicts a hole region, delamination damage peaks radiating from the hole region and a background region; and a computing device including drawing software. The computing device is a non-transitory computer readable medium that includes circuitry and a memory storing program instructions, which include the drawing software, in which the program instructions, when executed by one or more processors, cause the one or more processors to perform the tasks of operating the drilling tool, receiving the images from the scanner, measuring the images, generating curves and tracings of the images, shading the images, and determining the sizes of chip and burr regions and providing charts, graphs and reports regarding the measurement results. The computing device is configured to measure a maximum delamination damage peak; measure a maximum diameter $D_{max}$ of a first circle concentric with a center of each drilled hole, where the maximum diameter $D_{max}$ extends through the center to a tip of the maximum delamination damage peak; and calculate a delamination size, $S_d$, and a delamination factor, $F_d$, of each drilled block. The computing device is further configured to measure the radius of each delamination damage peak; sort the radii from largest to smallest; select the delamination peaks having the three largest radii; generate a second circle eccentric to the drilled hole and tangent to the delamination peaks having the three largest radii; determine a maximum second circle diameter, $D_{min}$; calculate a delamination parameter, $F_{dmin}$, based on the maximum second circle diameter, $D_{min}$ and the nominal diameter $D_{nom}$.

In another exemplary embodiment, a method for determining a feed velocity and a drilling speed for drilling holes in fiber reinforced plastic composites is disclosed. The method includes drilling, with a drilling tool, a first set of a plurality of holes at a first feed velocity and a first drill speed; drilling, with the drilling tool, a second set of a plurality of holes at a second feed velocity and a second drill speed; measuring, with a computing device, a burr formation and a chip formation of each of the first set and the second set; comparing, with the computing device, the burr formation and chip formation of the first set to the second set; determining, with the computing device, whether the first set or the second set has the smallest amount of burr formation and chip formation; and identifying, with the computing device, the feed velocity and drill speed which gives the smallest amount of burr formation and chip formation.

The foregoing general description of the illustrative embodiments and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein:

FIG. 4A illustrates cutting of fibers by a cutting tool at a fiber cutting angle of 0 or 180°, according to certain embodiments;

FIG. 4B illustrates cutting of fibers by the cutting tool at a fiber cutting angle of 45°, according to certain embodiments;

FIG. 4C illustrates cutting of fibers by the cutting tool at a fiber cutting angle of 90°, according to certain embodiments;

FIG. 4D illustrates cutting of fibers by the cutting tool at a an obtuse fiber cutting angle, according to certain embodiments;

FIG. 6A illustrates the instantaneous position of cutting lips and a velocity vector with respect to a drill bit in a woven braid interlaced with warp and fill fibers, according to certain embodiments;

FIG. 6B illustrates the instantaneous position of cutting lips and the velocity vector with respect to the drill bit where a force vector and the velocity vector are perpendicular to the warp fibers at edge position angles equal to 0° and 180°, according to certain embodiments;

FIG. 6C illustrates the instantaneous position of cutting lips and the velocity vector with respect to the drill bit where the force vector and the velocity vector are perpendicular to the warp fibers at edge position angles equal to 90° and 270°, according to certain embodiments;

FIG. 6D illustrates the instantaneous position of cutting lips and the velocity vector with respect to a drill bit where a force vector and the velocity vector are perpendicular to the warp fibers at edge position angles equal to 45° and 225°, according to certain embodiments;

FIG. 13 shows digital scanned images of push-out delamination in drilling quasi-transparent GFRP composite, according to certain embodiments;

FIG. 14 shows digital scanned images of push-out delamination in a drilling opaque GFRP composite, according to certain embodiments;

FIG. 15 shows digital scanned images of push-out delamination in drilling carbon fiber reinforced epoxy (CFRE) composites, according to certain embodiments;

FIG. 16 shows optical microscopy images of push-out delamination in drilling the CFRE composites, according to certain embodiments;

FIG. 18 shows representative images of the induced damages in drilling woven GFRP samples at various feeds at a speed of 14.3 m/min, where a) shows peel-up delamination and b) shows push-out delamination, according to certain embodiments;

FIG. 19 shows representative images of the induced damages in drilling woven GFRP samples at various feeds at a speed of 27.5 m/min, where a) shows peel-up delamination and b) shows push-out delamination, according to certain embodiments;

FIG. 25C shows representative fracture samples in the pin-bearing tests, according to certain embodiments;

DETAILED DESCRIPTION

Figure 1:
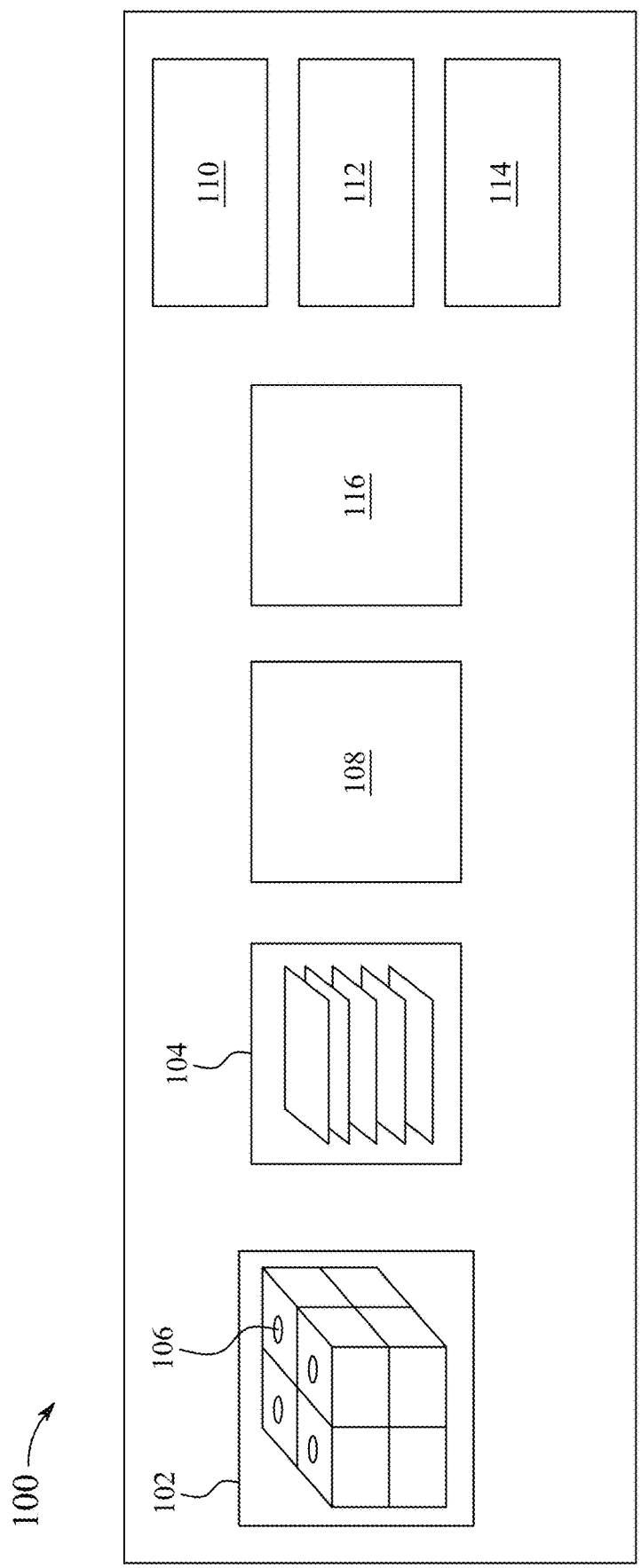
FIG. 1 is an exemplary block diagram of a system for measuring drilling damage in fiber reinforced plastic composites, according to certain embodiments.

In the drawings, like reference numerals designate identical or corresponding parts throughout the several views. Further, as used herein, the words "a," "an" and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values therebetween.

Aspects of this disclosure are directed to a system and a method for measuring drilling damage in fiber reinforced plastic composites. Specifically, the influence of cutting parameters (feed and speed) on a large number of machinability parameters is determined. The machinability parameters include, but are not limited to, thrust force, torque, delamination, surface roughness, size error, burr factor, notched strength and bearing strength. The present disclosure provides simple and inexpensive image processing techniques for evaluating damage (for example delamination) and burr areas. In some aspects of the present disclosure, the mechanics of chip and burr formation are also investigated with the aid of scanning electron microscope (SEM) examination of drilled specimens. The present disclosure provides a new, easy, inexpensive, and accurate AutoCAD image processing (ACIP) technique for measuring the delamination and burr areas and factors in drilling GFRP composites.

FIG. 1 illustrates an exemplary block diagram of a system 100 for measuring drilling damage in fiber reinforced plastic composites. The system 100 includes a plurality of drilled blocks 102, a plurality of black substrates 104, where each drilled block includes a drilled hole 106 and each black substrate 104 covers one side of each block over the drilled hole 106. The system 100 also includes a scanner 108 configured to: (i) scan the side of each block covered by the black substrate 104 and (ii) generate a scanned image, where the scanned image depicts a hole region, a background region, and delamination damage peaks radiating from the hole region. The scanner may be a color scanner to capture the light pattern of the features, such as the hole, chips, and burrs, generated by the scanner light. A color scanner will capture gradations in the light pattern, which indicate depth of the features. In some aspects, any model of a high-resolution color scanner can be used. The black substrate may be a black film, black paper, a black light filter, a black cellulose film. The black substrate absorbs light in the visible region of the spectrum, thus isolating the drilled hole and features of interest, such as the chips and burrs from the solid section of the drilled block.

In addition, the system 100 includes a computing device 116 including drawing software; a scanning electron microscope 110 (hereinafter referred to as "the SEM 110"); a tensile strength tester 112; and an in-plane shear tester 114. In a non-limiting example, the scanner 108 may be an Epson V370, model 4800×9600 dpi, available from Epson America, Inc., 3131 Katella Avenue. Los Alamitos, Calif. 90720. In a non-limiting example, the SEM 110 may be a Nova Nano SEM-230, available from FEI Company, Oregon, United States.

Figure 2A:
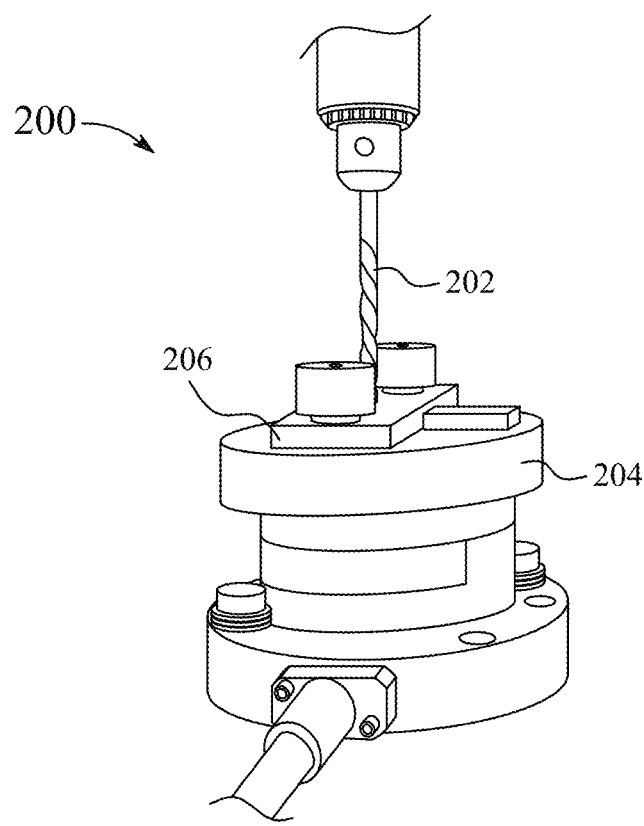
FIG. 2A illustrates drilling a hole, according to certain embodiments.
Figure 2B:
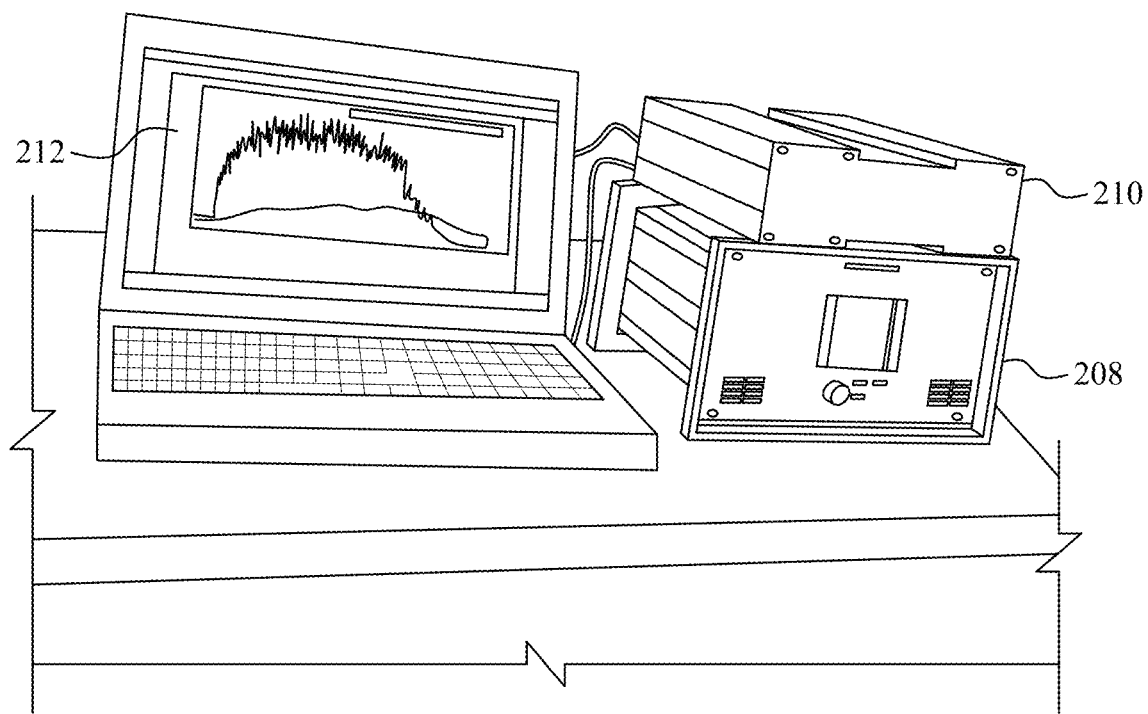
FIG. 2B illustrates a drilling test setup, according to certain embodiments.

FIG. 2A illustrates drilling a hole in a test sample 206 and FIG. 2B illustrates a computer of the drilling test setup, according to aspects of the present disclosure. Specifically, FIG. 2A illustrates a drilling test setup 200, according to an aspect of the present disclosure. The drilling test setup 200 includes a drill bit 202 having a nominal diameter of about 10 mm and a platform 204 arranged vertically below the drill bit 202. In a non-limiting example, the drill bit 202 may be a m2 HSS twist drill bit; ASTM A681 (Din 17350), available from Irwin Tools, 8936 Northpointe Executive Dr, Suite 200, Huntersville, N.C., United States. In a non-limiting example, the drilling test setup 200 may be a conventional radial drilling press machine, such as the RD-750 Radial Drill Press available from Willis Machinery & Tools Co., 4545 South Ave., Toledo, Ohio, United States.

The test sample 206, such as glass fiber reinforced plastic (GFRP) (or, alternatively fiber reinforced plastic), is mounted on the platform 204 and one or more holes are drilled into the test sample 206 using the drill bit 202. In a non-limiting example, the measurement control of the drilling test setup 200 is a Kistler dynamometer 9272, available from Kistler Instruments Corp., Novi, Mich., United States. The drilling test setup 200 also includes a multichannel charge amplifier 208, a data acquisition unit 210, and a display device 212 coupled to the data acquisition unit 210 to display data relating to, for example, forces measured during the drilling. The thrust force and torque are measured using the Kistler dynamometer that is connected to the display device 212 via the multichannel charge amplifier 208. In a non-limiting example, data of the thrust force and the torque may be collected at an acquisition rate of 500 Hz via Dynoware software (See: Abrão A M, Rubio J C, Faria P E, Davim, Japan). In an aspect of the present disclosure, five samples are drilled for each test condition, where three samples (of size 30×150 mm) are used for characterizing a notched strength and other two samples (of size 60×80 mm) are used for measuring a bearing strength.

According to an aspect, the GFRP composite is fabricated from 10-layers of plain-woven E-glass fiber using hand lay-up technique. In a non-limiting example, the areal weight of the fabric is 324 g/cm² and the epoxy is Araldite LY 5138-2/HY 5138 (100:23 part by weight). The lower fabric areal weight gives better fiber/matrix impregnation and enhances performance of mechanical properties. The fiber volume fraction (Vf) is established using an ignition method in accordance with ASTM D3171-09.

$$Vf = \frac{n*Aw}{\eta f*t}$$

where n equals the number of laminate layers (10-layers), Aw is the areal weight of the fabric, t is the laminate thickness (3.1 mm), and $\eta f$ the fiber density (2.5 g/cm³).

Figure 3A:
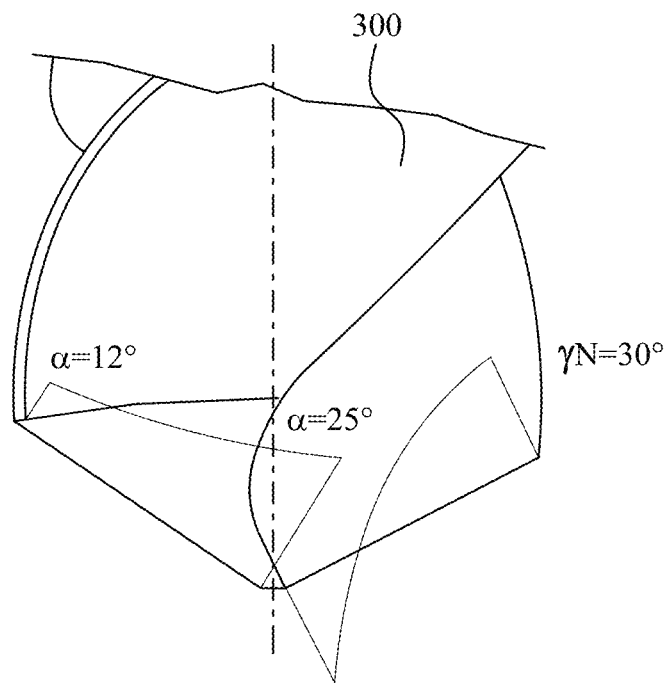
FIG. 3A illustrates a variation of a normal rake angle and a clearance angle along a cutting edge of a twist drill, according to certain embodiments.

FIG. 3A illustrates a variation of a normal rake angle ($\gamma$) and a clearance angle ($\alpha$) along a cutting edge of a twist drill 300. In a non-limiting example, the twist drill 300 may be a HSS drill, available from Irwin Tools, 8936 Northpointe Executive Dr, Suite 200, Huntersville, N.C., United States. Geometries of the twist drill 300 play a vital role in chip formation in drilling of FRP composites. The negative rake angles of a chisel edge contribute about 40-60% of total thrust force irrespective of hole diameter. The chisel edge with zero speed at drill center extrudes the material rather than shearing it. (See: Choudhury M R, Srinivas M S, Debnath K. "Experimental investigations on drilling of lignocellulosic fiber reinforced composite laminates". Journal of Manufacturing Processes 2018; 34:51-61; Khashaba U A, El-Keran A A. "Drilling analysis of thin woven glass-fiber reinforced epoxy composites". Journal of Materials Processing Tech. 2017; 249: 415-425; Tsao C C, Hocheng H. "The effect of chisel length and associated pilot hole on delamination when drilling composite materials". Int. J. Mach. Tools Manuf. 2003; 43: 1087-1092, each incorporated herein by reference in its entirety).

Figures 3B, 3C, 3D:
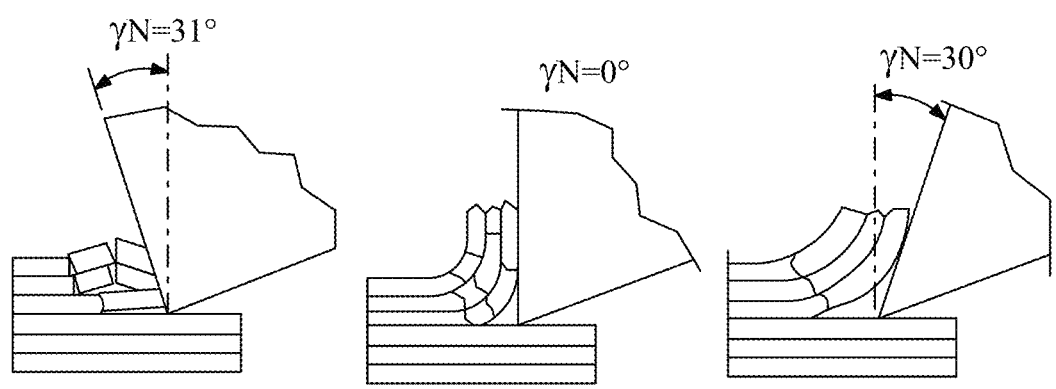
FIG. 3B illustrates the effect of the variation to a negative rake angle on chip formation when cutting at 0° fiber direction, according to certain embodiments.
FIG. 3C illustrates the effect of bending stress on peel-up delamination when cutting from the 0° fiber direction, according to certain embodiments.
FIG. 3D illustrates an effect of the variation to a positive rake angle on delamination when cutting at 0° fiber direction, according to certain embodiments.

Also, the chisel edge contributes about 50% of the total thrust force in drilling by using a pilot hole (See: Tsao C C, Hocheng H. "The effect of chisel length and associated pilot hole on delamination when drilling composite materials". Int. J. Mach. Tools Manuf. 2003; 43: 1087-1092, incorporated herein by reference in its entirety). Further, a relief angle of the margin edges is equal to zero, which increases the friction with a wall of the machined hole. In addition, the margins have the maximum diameter (i.e. maximum speed), which is the main reason for intensive wear which limits life of the twist drill 300. The variation of the rake angle ($\gamma$) and a clearance angle ($\alpha$), as well as the cutting speed, along the lips of the twist drill 300 results in complex chip mechanism, as illustrated in FIG. 3B through FIG. 3D. The normal rake angle ($\gamma$) is positive at a lip-flute intersection and decreases continuously to negative value at a chisel-lip crossing, as shown in FIG. 3A. A negative rake angle ($\gamma$) at the chisel-lip intersection leads to increase in the thrust force. Fiber buckling is determined as a main type of chip formation in cutting the FRP composites at the negative rake angle ($\gamma$), as shown in FIG. 3B. As shown in FIG. 3C, the rake angle ($\gamma$) is zero near the middle of the cutting edge, which increases a bending stress on the fiber. Hence, the fiber is fractured in tension/compression mode before an interlaminar shear (also referred to as the delamination). This mechanism is applicable for brittle glass fibers and hence it is preferred to use drills with a small rake angle ($\gamma$) to minimize peel-up delamination (See: Choudhury M R, Srinivas M S, Debnath K. "Experimental investigations on drilling of lignocellulosic fiber reinforced composite laminates". Journal of Manufacturing Processes 2018; 34:51-61, incorporated herein by reference in its entirety). High toughness fibers tend to bend and buckle without fracture. As shown in FIG. 3D, a positive value of the rake angle ($\gamma$) at the lip-flute intersection results in delamination at an entrance of the twist drill 300. The three chip types illustrated in FIG. 3B through FIG. 3D may be observed when drilling blind holes.

FIG. 4A to FIG. 4D illustrates the cutting of fibers by a drilling tool, such as the twist drill 300, at different fiber cutting angles. Chip separation mechanisms in drilling the FRP composites are dependent on the rake angle ($\gamma$) of the cutting lips, and the angle between a fiber orientation (k) and an instantaneous velocity vector (Vc) of the cutting edges during the drilling cycle (See: Poulachon G, Outeiro J, Ramirez C, André V, Abrivard G.: Hole surface topography and tool wear in CFRP drilling". Procedia CIRP 2016; 45:35-38; Xu J, Mkaddem A, El Mansori M. "Recent advances in drilling hybrid FRP/Ti composite: A state-of-the-art review". Composite Structures 2016; 135: 316-338; Wang D H, Ramulu M, Arola D. "Orthogonal cutting mechanisms of graphite/Epoxy composite. Part I: unidirectional laminate". Int J Mach Tools Manufact 1995; 35(12): 1623-1638; Shu L, Li S, Fang Z, Kizaki T, Kimura K, Arai G, Arai K, Sugita N. "Study on dedicated drill bit design for carbon fiber reinforced polymer drilling with improved cutting mechanism". Composites: Part A 2021; 142: 106259; Pervaiz S, Kannan S, Huo D. Mamidala R. "Ecofriendly inclined drilling of carbon fiber-reinforced polymers" (CFRP). Int J Adv Manuf Technol 2020; 111: 2127-2153, each incorporated herein by reference in its entirety). The chip formation mechanisms in drilling the FRP composites are classified into (i) a layered peeling fracture when the direction of Vc is parallel to the fibers with an orientation of 0° or 180°, as shown in FIG. 4A; (ii) a shear fracture owing to a compression loading across an axis of the fiber when the Vc direction makes an acute angle with the fiber, as shown in FIG. 4B; (iii) a compression shear and sliding movement which crushes the fiber at an orientation of 90°, as shown in FIG. 4C; and (iv) a bending shear as the Vc direction which makes an obtuse angle with the fiber, as shown in FIG. 4D.

Figure 5A:
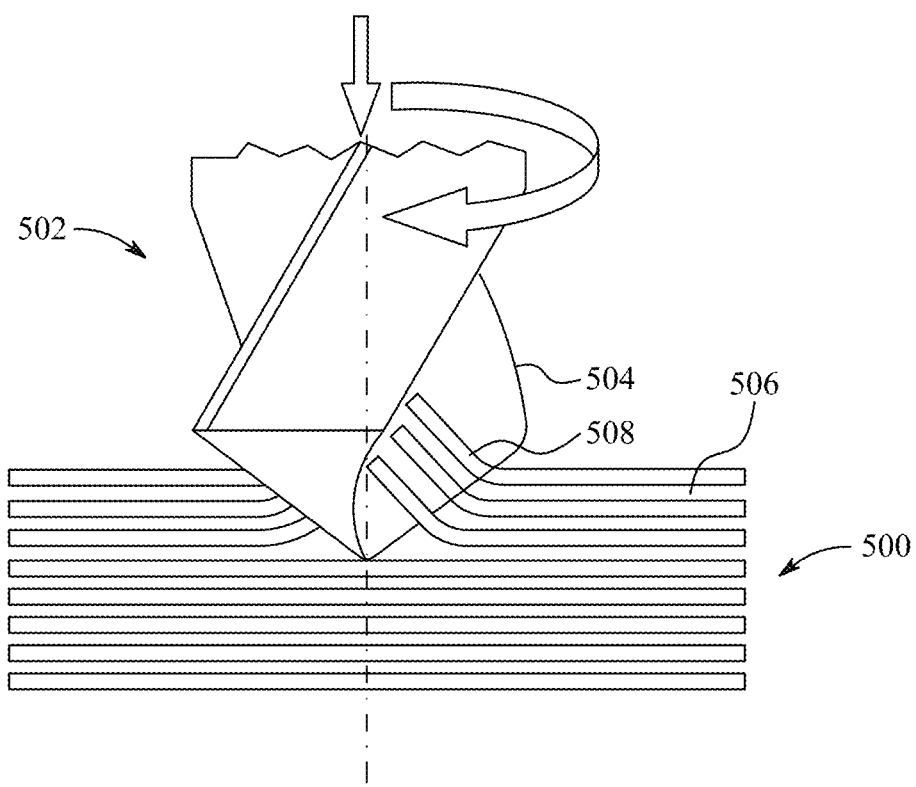
FIG. 5A illustrates delamination in drilling a fiber reinforced plastic (FRP) composite at a drill entry plane, according to certain embodiments.
Figure 5B:
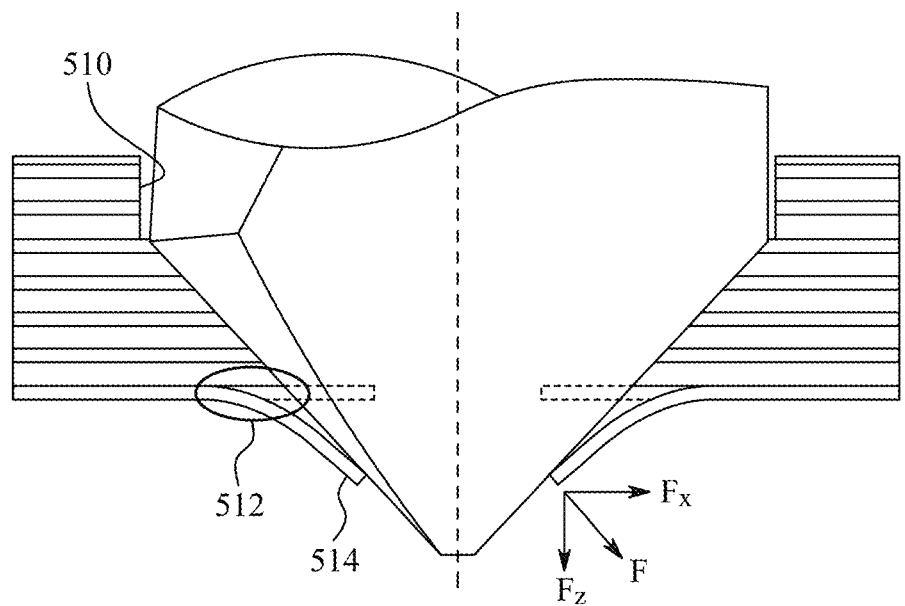
FIG. 5B illustrates delamination in drilling a fiber reinforced plastic (FRP) composite at a drill exit plane, according to certain embodiments.

FIG. 5A and FIG. 5B illustrate delamination in drilling the FRP composite 500 at a drill entry plane and a drill exit plane, respectively, according to an aspect to the present disclosure. Particularly, FIG. 5A illustrates the drill bit 502 contacting the entry plane of the FRP composite 500, where a flute 504 of the drill bit 502 contacts the resin fibers 506 of the FRP composite 500 and produces peel-up delamination 508. With further travel into the FRP composite 500, the drill bit 502 forms a hole 510 as shown in FIG. 5B. During an exit from the FRP composite 500, the drill bit 502 produces a push-out delamination 512 at the exit plane.

After the drill bit 502 penetrates the FRP composite 500, an upper lamina slides inside the flute 504 before being completely cut. Accordingly, the size of the peel-up delamination 508 primarily depends on the geometry of the drill bit 502 (such as, rake and helix angles). As the drill bit 502 advances toward the exit plane, a thickness of uncut fiber piling under the drill bit 502 becomes thinner and, thus, a resistance to bending decreases. At this instant, the compressive thrust force exceeds the interlaminar bonding strength and thus, the push-out delamination 512 occurs around the drilled hole at the exit plane. A burr formation 514 is aggravated for composite materials with high toughness fibers that exhibit significant downward bending rather than shearing, as shown in FIG. 5B. Hence, the fibers which are not cut by the drill bit 502 lead to the burr formation in the exit plane. The delamination 512 and the burr formation 514 in the FRP composite 500 may be reduced by decreasing the thrust force (Fz) and the radial force (Fx).

FIG. 6A illustrates the instantaneous position of cutting lips and the velocity vector Vc with respect to the drill bit 502 of FIG. 5A in a woven braid made by interlacing of warp fibers and fill fibers. The woven braid consists of orthogonal warp fiber tows (0°) and fill fiber tows) (90°, where each cutting lip of the drill bit 502 contacts four tangent fiber bundles per one revolution per layer. Two warp fiber bundles are located at the edge position angles of 0° and 180°, as shown in FIG. 6B, and two fill fiber bundles are located at edge position angle of 90° and 270°, as shown in FIG. 6C. The compressive loading of these fibers result in higher peripheral (tangential) force and the torque.

According to an aspect, the FRP composite 500 is fabricated from at least 10 layers. Thus, when cutting edges of the drill bit 502 penetrates the FRP composite 500 (for example, for a depth of 3 mm), each cutting edge contacts 20 fill fibers, 20 warp fibers, and 40 interlaced warp/fill fibers at 45°, 135°, 225° and 315°, as shown in FIG. 6A to 6D, thereby defining onset of delamination at various cutting edge positions. As illustrated in FIG. 6A, parallel warp fibers result in peel-up delamination portions (such as the peel-up delamination portion 306 shown in FIG. 3B) whereas the fill fibers are subjected to deformation and/or crushing.

Figure 7A:
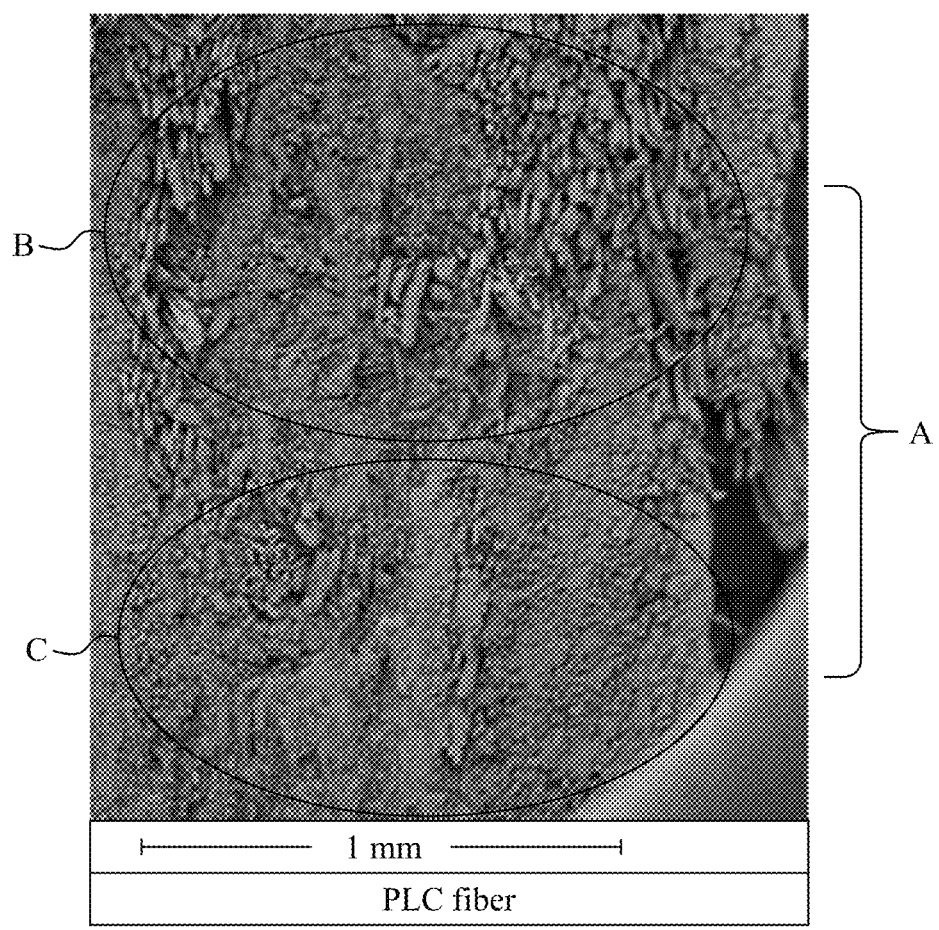
FIG. 7A is a representative sample of a scanning electron microscope (SEM) image of a drilled hole showing peel-up delamination at a drill entry and a push-out delamination at a drill exit, according to certain embodiments.

FIG. 7A illustrates a representative sample of an SEM image of drilled holes. Region "A" of FIG. 7A represents peel-up delamination due to stretching of top lamina in Mode-I interlaminar shear developed in a hole drilled at 0.05 mm/r and 14.3 m/min. The microstructure of the machined surface reveals fibers which are fractured due to the different fiber orientations within single lamina. Region "B" of FIG. 7A represents interlaced warp/fill fibers having a 45° orientation which are fractured with rougher surface and region "C" of FIG. 7A represents fibers having about 90° orientation which are fractured with a relatively smoother surface.

Figure 7C:
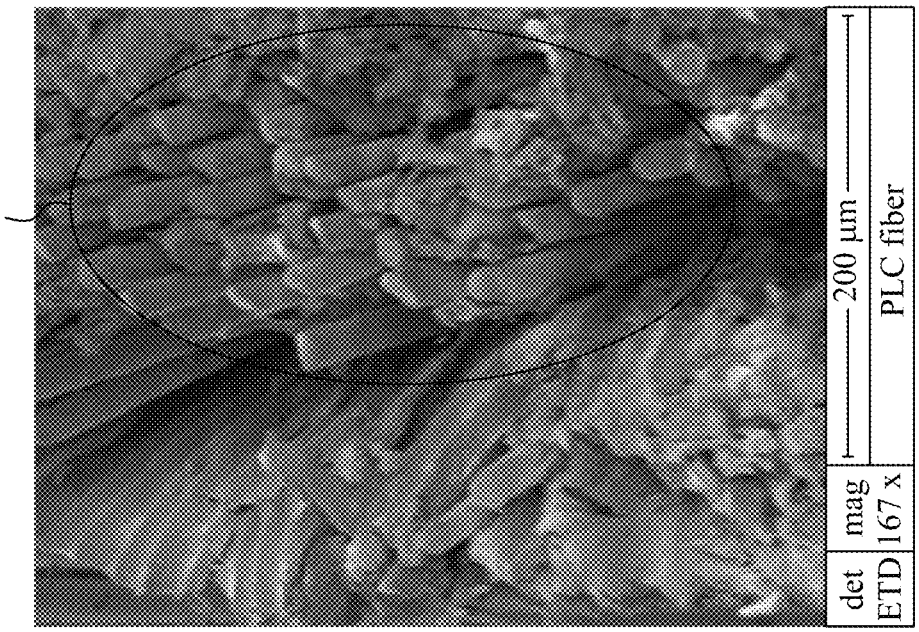
FIG. 7C illustrates a sample of an SEM image showing magnification of an interlaminar shear area in FIG. 7B, according to certain embodiments.
Figure 7B:
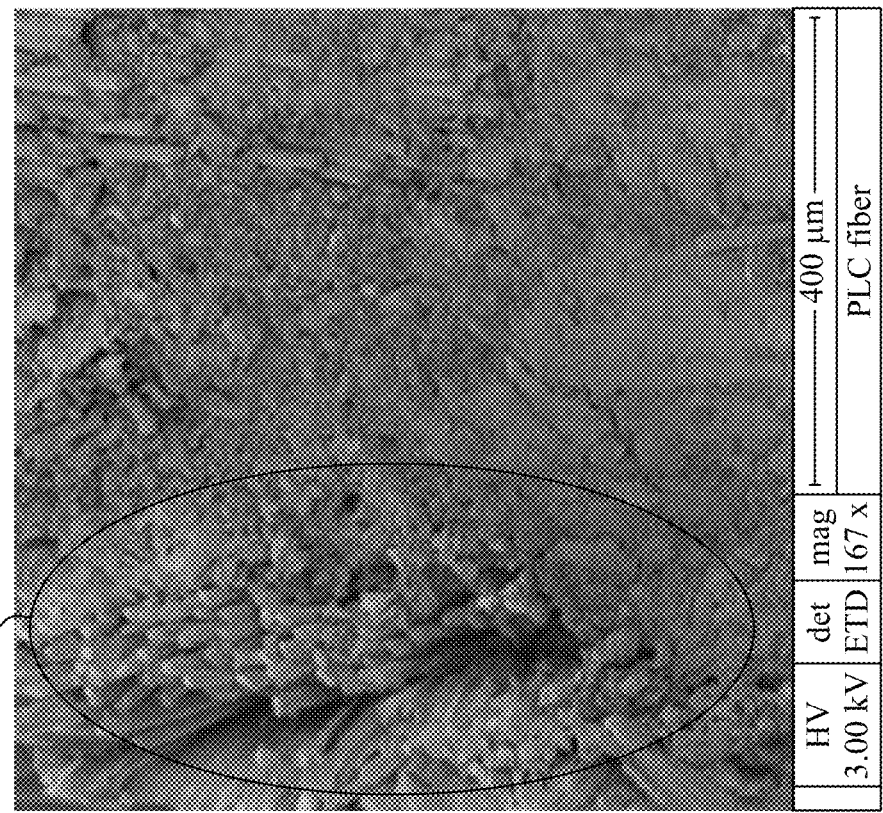
FIG. 7B illustrates a sample of an SEM image of holes drilled at 0.05 mm/r and 14.3 m/min with push-out delamination in Mode-I at the drill exit, according to certain embodiments.
Figure 7D:
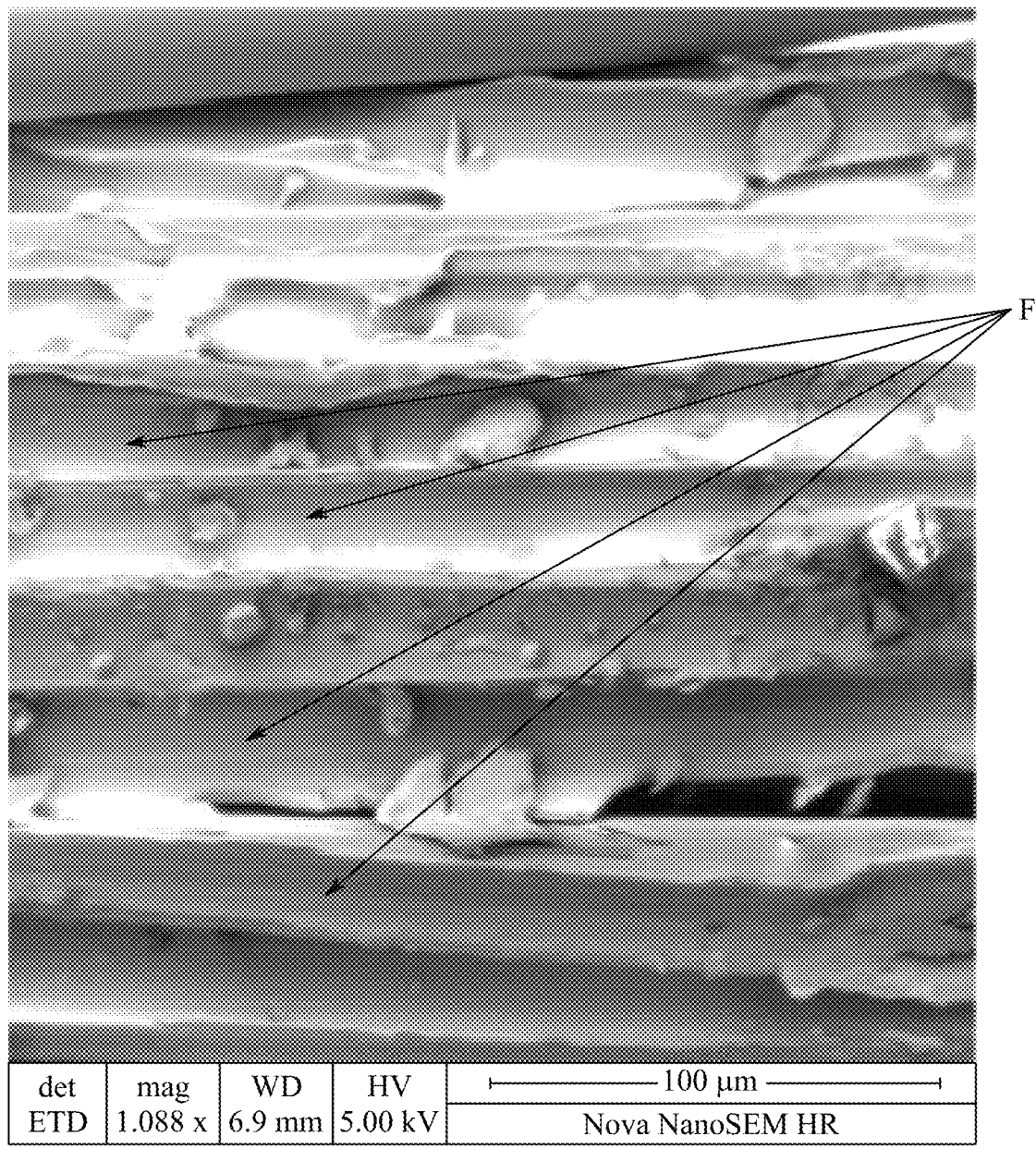
FIG. 7D illustrates a sample of an SEM image showing a matrix of the delaminated layer, according to certain embodiments.

It can be observed from FIG. 7B that the push-out delamination (represented by region "D") is dominated by stretching a last lamina in Mode-I interlaminar shear via compressive thrust force. Clean fiber surfaces (represented by region "E") in FIG. 7C demonstrate weak interfacial bond strength between the fibers and the matrix material, which result in the smoother surface (represented by region "F") of the delaminated fibers, as shown in FIG. 7D. In an aspect of the present disclosure, permanent flexural deformation of the matrix material at the drill exit (as shown in FIG. 5C) demonstrates softening of the fibers due to increase of accumulated heat with increase in hole depth (or cutting time).

FIG. 8A to FIG. 8F illustrate a set of representative samples of SEM images of holes drilled in a woven GFRP composite at a feed of 0.05 mm/r and speed of 14.3 m/min. It may be observed from FIG. 8A to FIG. 8F that the variation of fiber breaking type with respect to fiber orientation contributes significantly to the severe hole-wall damage formation.

As the tool, such as the drill bit 502 of FIG. 5A, feeds into the woven GFRP composite, the peeled layer slips up the rake face of the tool, leading to bending fracture resulting in fiber cantilever beams. The peel-up delamination is caused due to stretching of a top lamina in Mode-I interlaminar shear, as described with respect to FIG. 4A. A resulting fracture surface of an individual glass fiber due to a bending stress is illustrated in FIG. 8A. It may be understood that a compressive side 802 of the fibers is characterized by a shear failure at about 45° to a neutral axis 804 of the fiber. A tensile fracture side 806 is located approximately at a right angle (90°) with respect to the neutral axis 804 of the fiber. Both the compressive and tensile fracture sides 802, 806 are separated by the neutral axis 804, thereby demonstrating that the fiber is subjected to bending stress or bending fracture.

Figure 8B:
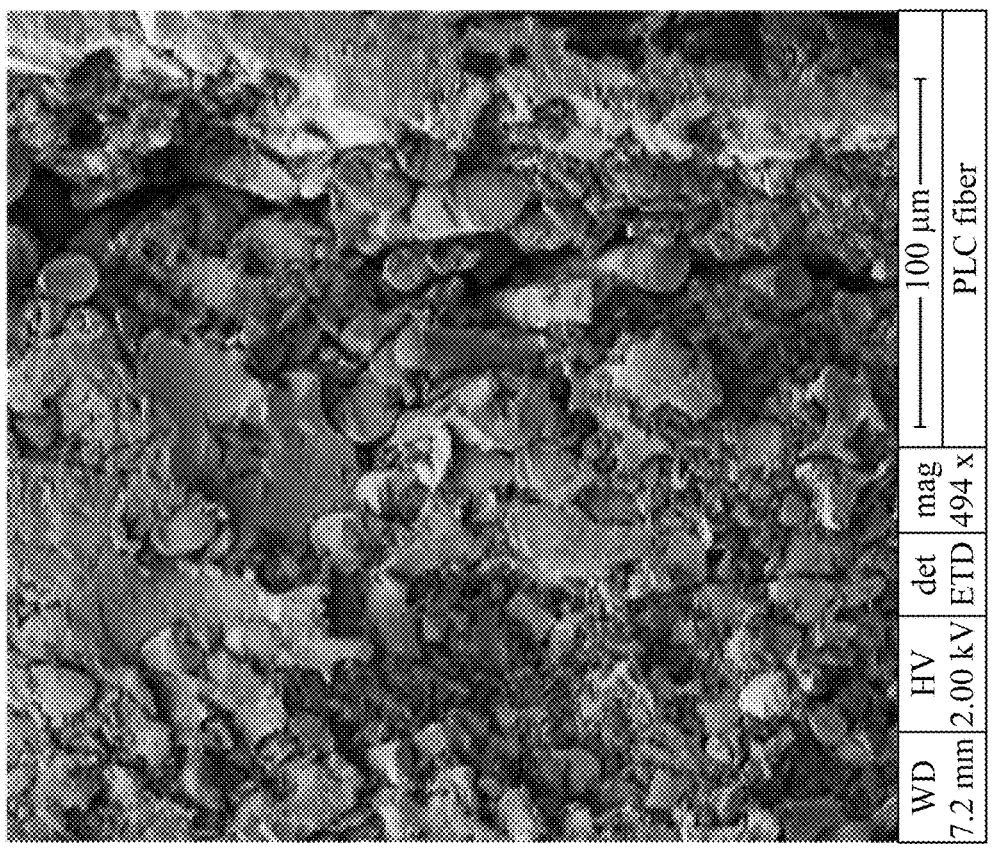
FIG. 8B is a representative sample of an SEM image showing the fiber fracture due to compressive induced shear at an angle of about 45°, according to certain embodiments.
Figure 8A:
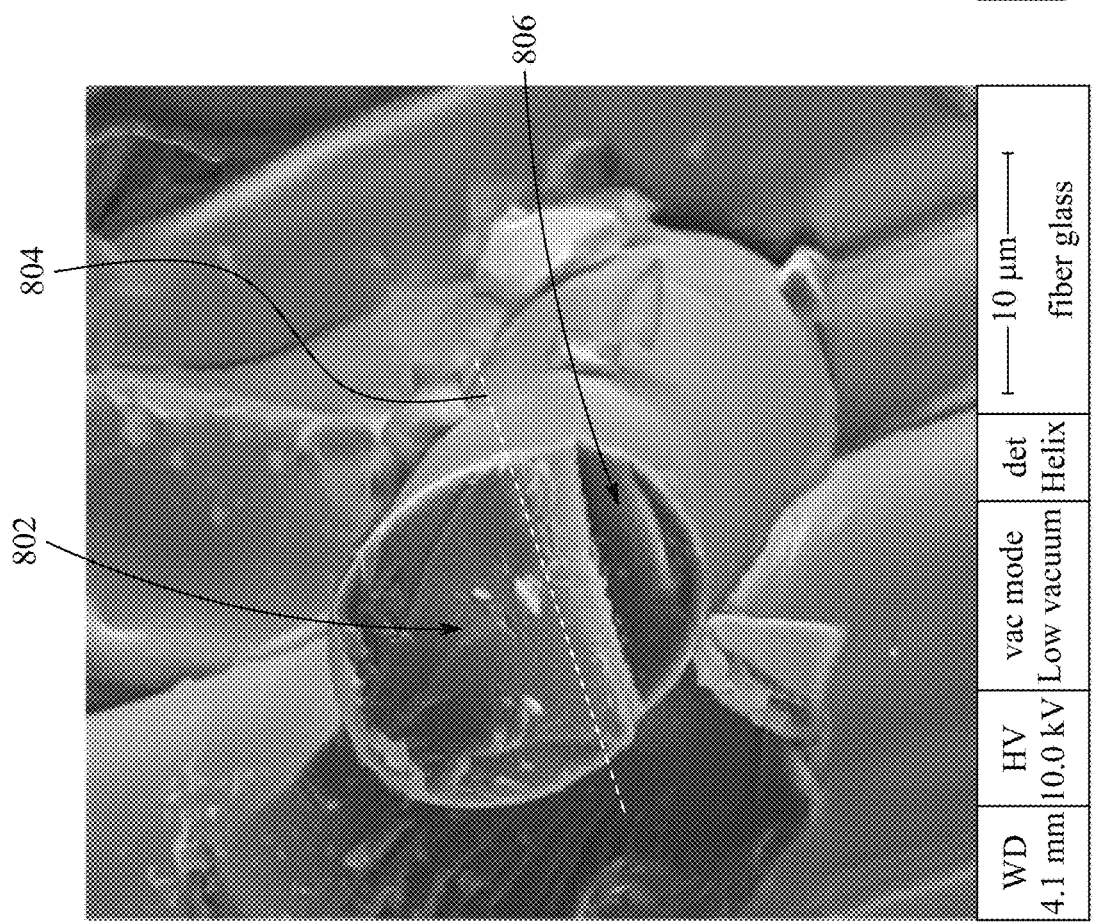
FIG. 8A is a representative sample of an SEM image showing bending fracture of fibers, according to certain embodiments.
Figure 8D:
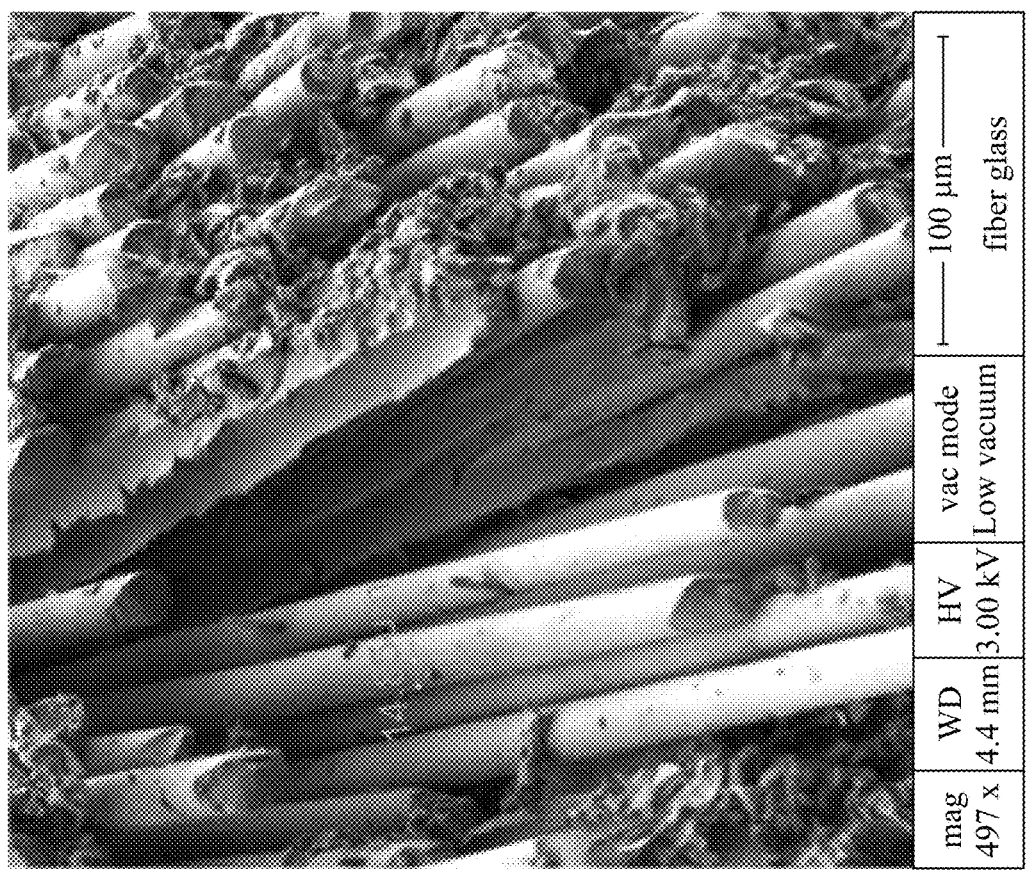
FIG. 8D is a representative sample of an SEM image showing inter-laminar shear failure, according to certain embodiments.
Figure 8C:
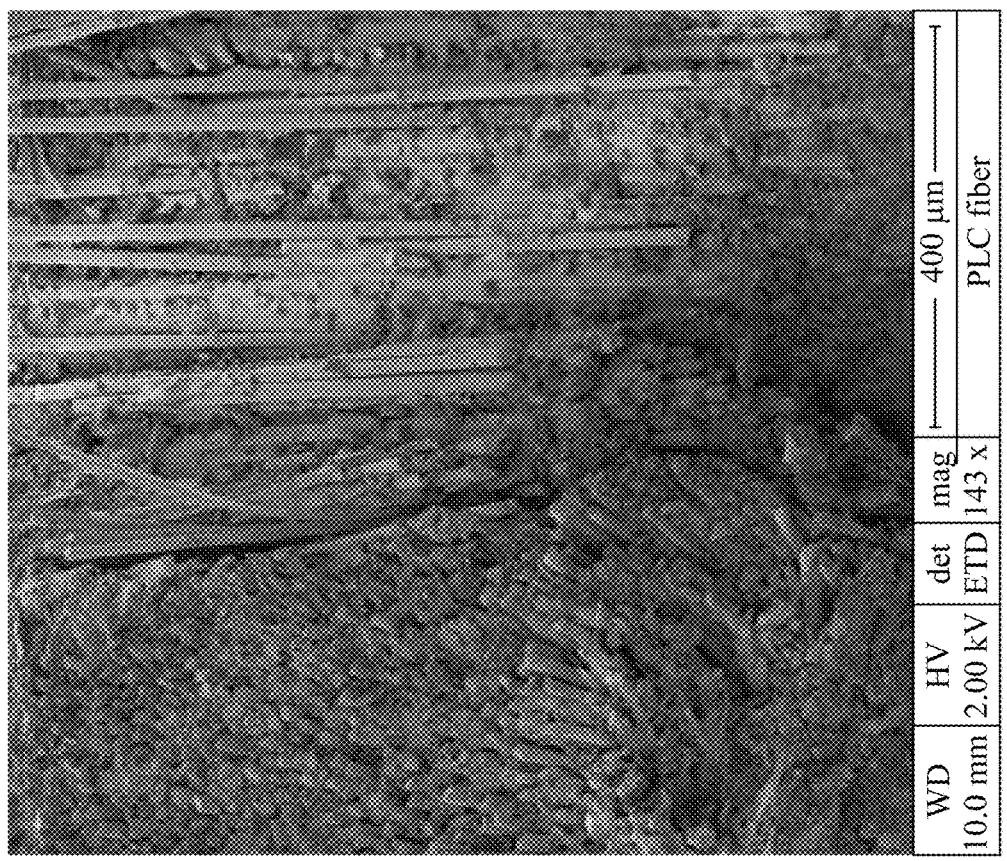
FIG. 8C is a representative sample of an SEM image showing interlaced woven/fill fibers, according to certain embodiments.
Figure 8F:
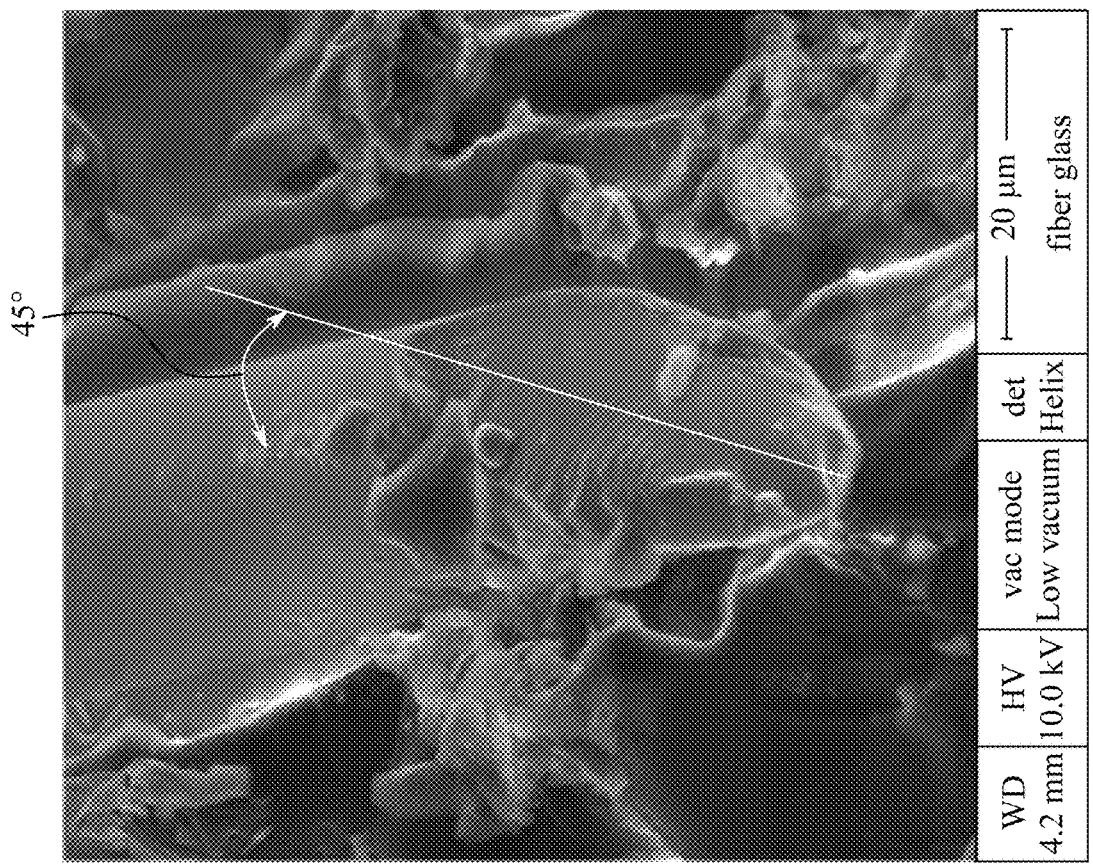
FIG. 8F is a representative sample of an SEM image showing fiber shear at an angle of 45°, according to certain embodiments.
Figure 8E:
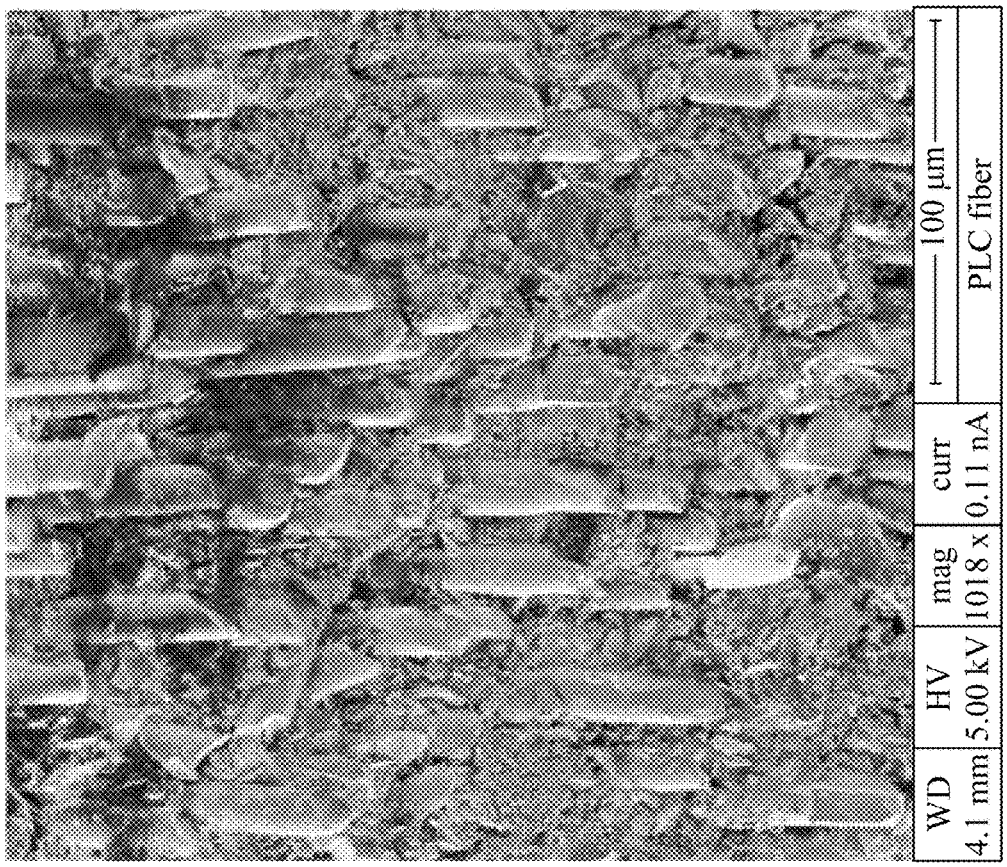
FIG. 8E is a representative sample of an SEM image showing a rough surface produced at a cutting angle of 135°, according to certain embodiments.

FIG. 8B illustrates the fibers fractured due to a compressive induced shear at an orientation of 45°. The fibers are sheared across axes thereof at different positions resulting in an irregular machined surface of periphery of the hole as shown in FIG. 4B. FIG. 8C illustrates interlaced woven/fill fibers, where the fill fibers with 90° orientation are associated with relatively smother surface compared to the wrap (0°) fibers. Such difference in surface texture may be attributed to compression shear accompanied with crushing of the fibers. The warp fibers (0° and 180°) illustrated in FIG. 8D exhibit inter-laminar shear failure, which is a main cause of the delamination, where the warp (0°) fibers are parallel to an instantaneous velocity vector of the drill bit. However, the fractured glass fibers have relatively clean surfaces without epoxy material attaching to them, which indicates weak interfacial bond strength of the warp (0°) fibers. FIG. 8E illustrates a rough surface resulting from a cutting angle oriented at about 135° and FIG. 8F illustrates shear of the fibers at about a 45° orientation. The SEM images of FIG. 8E and FIG. 8F indicate that the fibers are sheared at different angles to their respective axis when the cutting edge is at an angle of)−45° (135°. It is apparent from these figures that the shear fracture is a predominant failure mode of the glass fibers at about 45° to their axis, which is characterized by shiny appearance as seen in FIG. 8F.

Figure 9A:
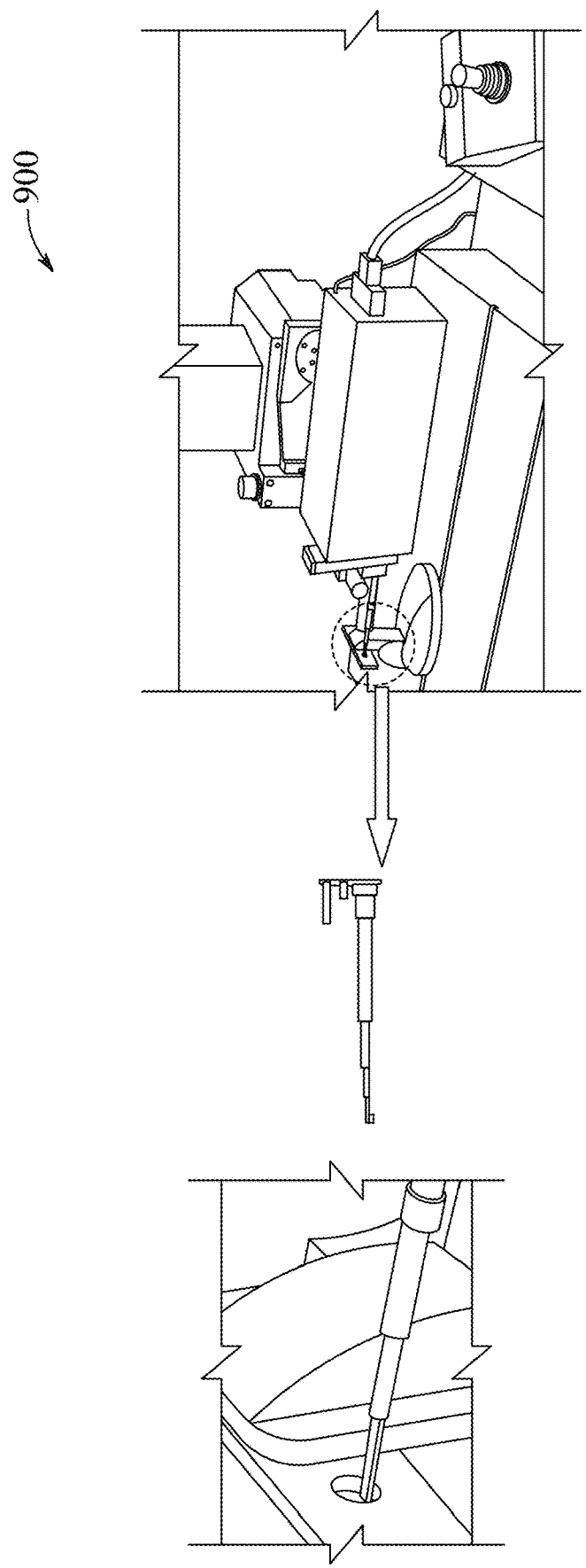
FIG. 9A is a surface roughness apparatus, according to certain embodiments.

FIG. 9A illustrates a setup 900 for determining surface roughness of the hole. According to an aspect, the surface roughness is measured along the periphery of the hole at various positions using a probe having a length of about 60 mm and provided with a coni-sphere diamond tip of 2 μm radius. In a non-limiting example, the probe may be a Talysurf series-2 and stylus probe, available from Berg Engineering and Sales Company, Inc. A cutoff value during the surface roughness measurement was considered as 0.8 mm. A surface roughness measurement instrument is connected to a computer, such as the computing device 116, to display a surface roughness profile and estimate many roughness parameters, such as Ra (an arithmetic average of a roughness profile along the periphery of the hole), Rq (a root mean square value of the roughness profile), Ry (a maximum height of the roughness profile), Rz (an average maximum height of the roughness profile), Rv (a maximum profile valley depth of the roughness profile), Rp (a maximum profile peak height), and $R_s$ (a mean spacing of profile irregularities). Due to an anisotropic and a non-homogeneity of the FRP composite 500, the surface roughness was measured at 0°, 45°, and 90° along the periphery of the hole and an average value was considered.

Figure 9B:
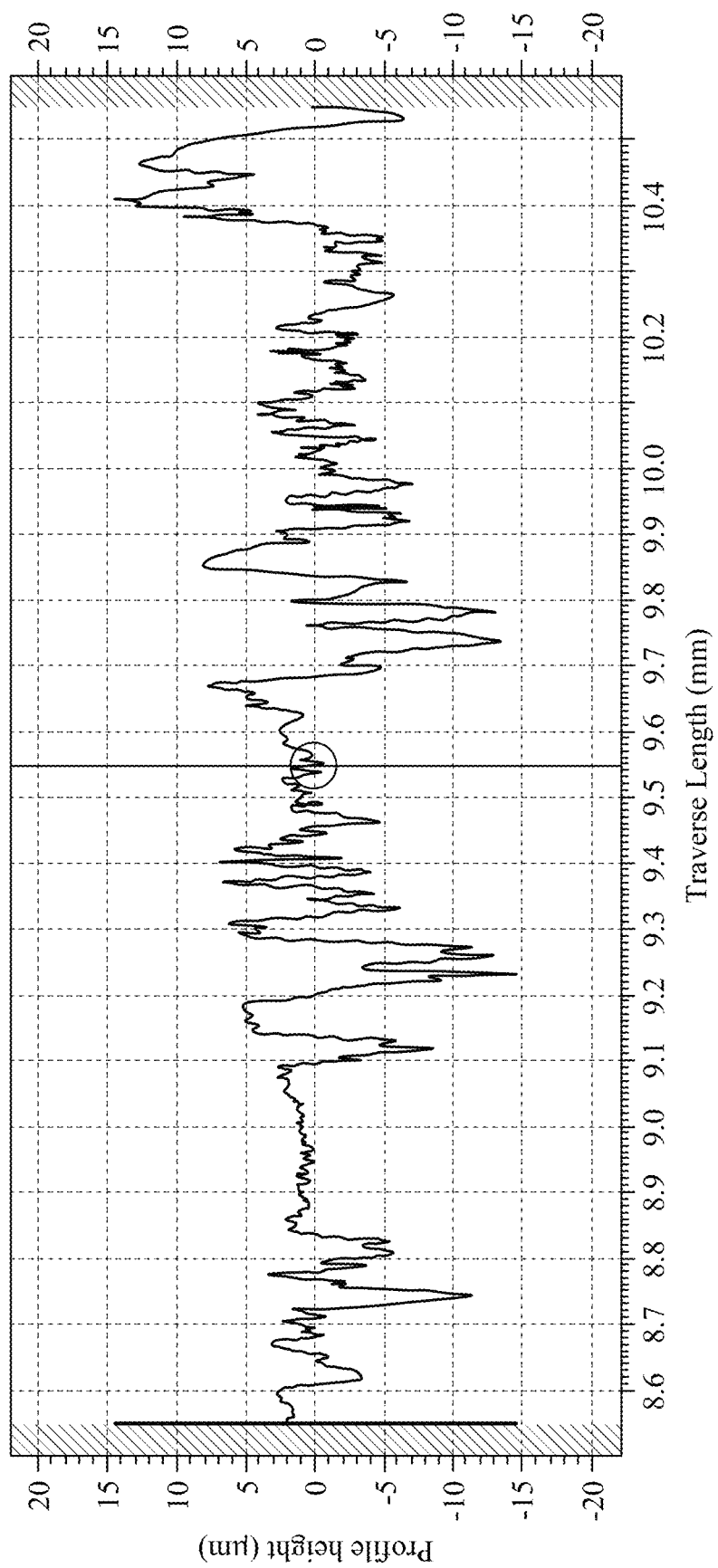
FIG. 9B is a graph of a surface roughness profile and parameters determined in drilling a hole, according to certain embodiments.

FIG. 9B illustrates a graph depicting representative sample of the surface roughness profile and parameters determined in drilling a hole at a feed of 0.05 mm/r and at a speed of 27.5 m/min. An exemplary table showing the roughness parameter and corresponding profile height (m) is provided below.

TABLE 1

Roughness parameters and corresponding profile height

| Roughness Parameter | Profile height (m) |
|---|---|
| Ra | 3.3675 |
| Rq | 4.5385 |
| Rp | 6.5427 |
| Rv | 8.6874 |
| Ry | 28.7947 |
| Rz | 15.2302 |
| Rs | 23.84 |

Figure 9D:
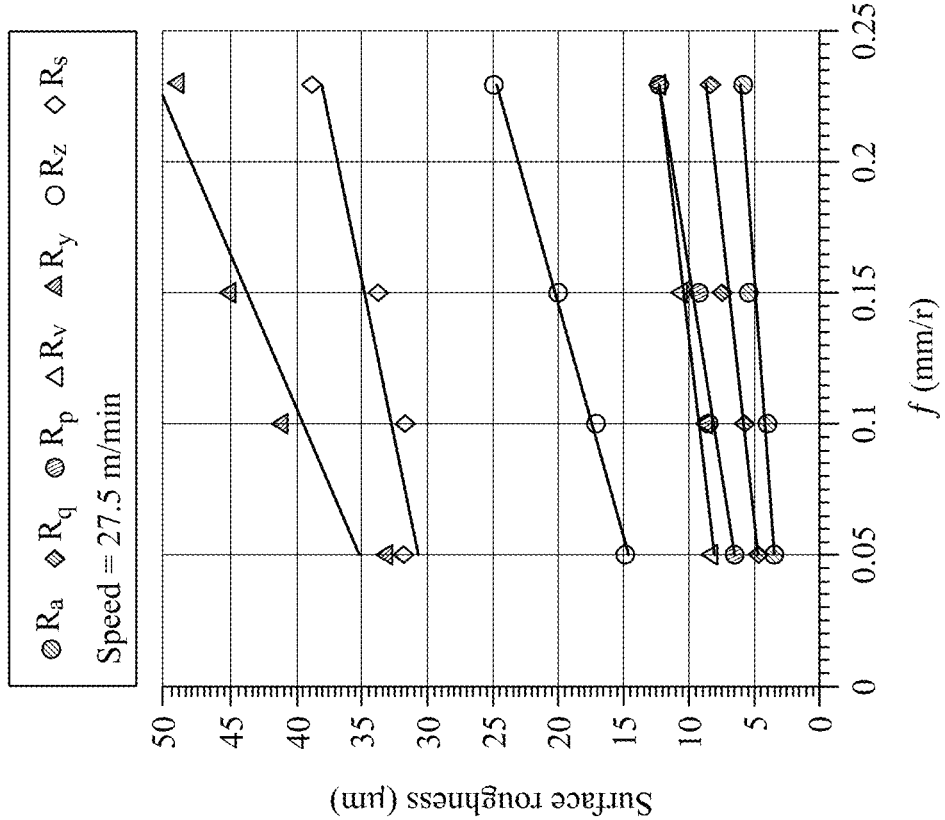
FIG. 9D illustrates the influence of the feed on the surface roughness of holes drilled at a speed of 27.5 m/min, according to certain embodiments.
Figure 9C:
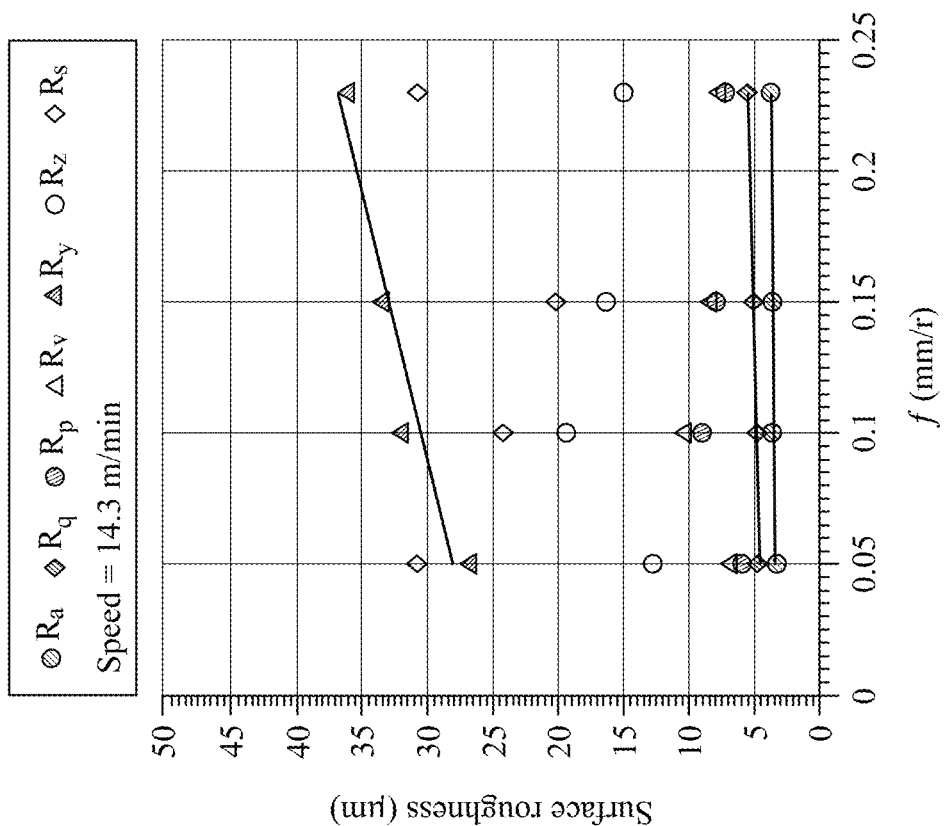
FIG. 9C illustrates the influence of the feed on the surface roughness of holes drilled at a speed of 14.3 m/min, according to certain embodiments.

FIG. 9C and FIG. 9D illustrate the influence of the feed on the surface roughness of holes drilled at a speed of 14.3 m/min and 27.5 m/min, respectively. The roughness parameters Ra, Rq and Ry are the parameters that may be used for representing the influence of the feed on the surface roughness in drilling the woven FRP composites. It can be observed from FIG. 9C and FIG. 9D that the surface roughness is increased with the feed (as observed in Palanikumar K. "Modeling and analysis for surface roughness in machining glass fiber reinforced plastics using response surface methodology". Materials and Design 2007; 28: 2611-2618; and Yaar N, Günay M. "The Influences of Varying Feed Rate on Hole Quality and Force in Drilling CFRP Composite". GU J Sci 2017; 30(3): 39-50, both incorporated herein by reference in their entirety). The influence of the cutting speed on the surface roughness was found to vary based on the amount of heat generated during the drilling and a configuration of the composite. As seen in FIGS. 9C and 9D, the surface roughness is increased with increasing cutting speed due to an increase in the generated heat, which leads to softening of the matrix, resulting in incomplete fiber cutting and fiber pull-out.

Measurement of Delamination and Burr Factors:

An experiment was performed in which a plurality of holes were drilled in the FRP composite 500 using the drill bit 502 having a nominal diameter, $D_{nom}$. The FRP composite 500 was separated (for example, divided by a cutting tool) into a plurality of blocks (such as blocks 102 in FIG. 1), such that each block defined one drilled hole. Each drilled block was covered with the black substrate 104 and scanned on a scanner 108 to generate a scanned image of each drilled hole. In a non-limiting example, the scanner 108 may be a high-resolution color flatbed scanner. A specimen of the FRP composite 500 was placed at the center of the scanner glass plate to avoid acquiring an image with an inclined hole wall. In some aspects, brightness, contrast, and intensity were adjusted on the scanner 108 to obtain a clear image of the overall damage area. The present disclosure provides an accurate AutoCAD image processing (ACIP) technique to separate the delamination 512 and the burr formation 514 at the nominal diameter, $D_{nom}$ of the drill bit 502. The scanned image was imported to a CorelDraw software to measure the size of the delamination 512 by drawing concentric and eccentric circles with the nominal diameter, $D_{nom}$. The diameters of the circles were measured with a resolution of $10^{-3}$ mm. Further, delamination factors were estimated as a ratio between a measured concentric and eccentric diameters and the nominal hole diameter, $D_{nom}$. The delamination and burr factors, based on the damage areas, were also measured using the developed ACIP technique with resolution of $10^{-6}$ mm.

Figure 10:
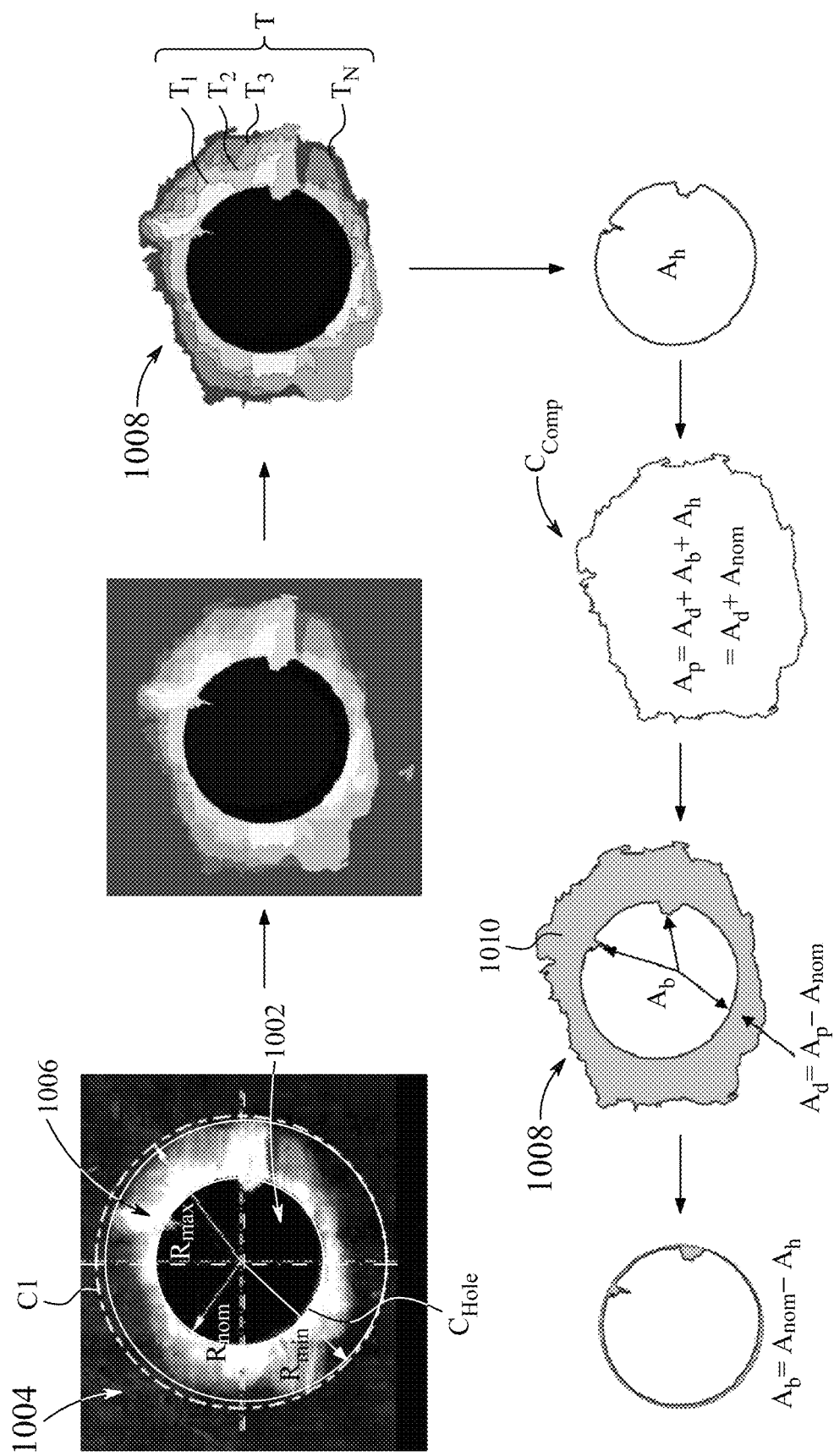
FIG. 10 shows a step-by-step process to determine delamination and burr formation areas from digital images of push-out delamination obtained in drilling woven GFRP composite, according to certain embodiments.
Figure 11:
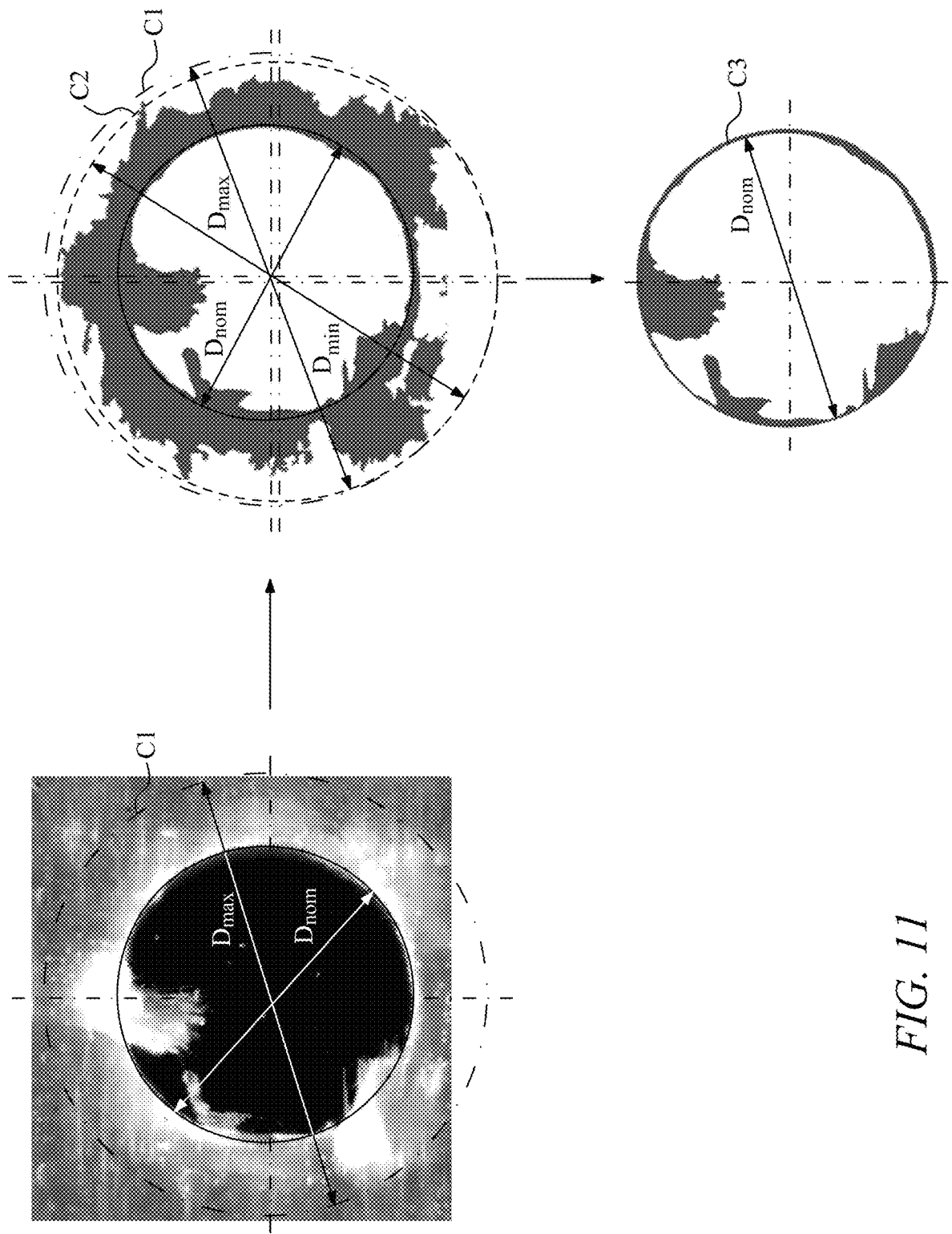
FIG. 11 shows details of the step-by-step process to determine delamination and burr formation areas from digital images of push-out delamination obtained in drilling woven GFRP composite, according to certain embodiments.

FIG. 10 and FIG. 11 each illustrate aspects of a step-by-step process for determining the delamination and the burr formation areas using digital images of the push-out delamination obtained in drilling woven GFRP composites at a feed of 0.1 mm/r and a cutting speed of 27.5 m/min. The arrow marks in FIG. 10 and FIG. 11 indicate an order of successive images in the step-by-step process. Since the light transmitted from the scanner varies brightness of the damaged zones (brightness being proportional with the damage severity), it may be observed that a color tone of the scanned image is brighter at the periphery of the hole and reduced in a radial outward direction with respect to a center of the hole "H". The scanned image depicts a hole region 1002, a background region 1004, and delamination damage peaks 1006 radiating from the hole region 1002, as shown in the first three steps of FIG. 10.

For each scanned image, the computing device 116 is then configured to measure a maximum delamination damage peak and a maximum diameter $D_{max}$ of a first circle "C1" (shown in FIG. 11) concentric with the center of each drilled hole. As used herein, the maximum diameter $D_{max}$ may be understood as a length of a chord of the first circle "C1" extending through the center thereof to a tip of the maximum delamination damage peak.

Further, the computing device 116 is configured to calculate a delamination size, $S_d$, and a delamination factor, $F_d$, of each drilled block based on the maximum diameter $D_{max}$ and the nominal diameter, $D_{nom}$.

$$S_d = \frac{(D_{max} - D_{nom})}{2} \quad (1)$$

$$F_d = \frac{D_{max}}{D_{nom}} \quad (2)$$

Computing device 116 is further configured to measure a radius of each delamination damage peak, sort the radii from largest to smallest, select the delamination peaks having the three largest radii, and generate a second circle "C2" (shown in FIG. 11) eccentric to the drilled hole "H" and tangent to the delamination peaks having the three largest radii. The computing device 116 is configured to determine a maximum second circle diameter, $D_{min}$, and calculate a delamination parameter, $F_{dmin}$, (given by equation (3) below), based on the maximum second circle diameter, $D_{min}$.

$$F_{dmin} = \frac{D_{min}}{D_{nom}} \quad (3)$$

According to an aspect, the computing device 116 comprises drawing software and is configured to separate a burr area from a delamination damage area of each scanned image of each drilled hole. In a non-limiting example, the drawing software may be CorelDraw®. Such separation is achieved by generating a first traced curve "C1" (represented as circle "C1" in a first image of FIG. 10 and a first image of FIG. 11) by tracing a periphery of the delamination damage peaks; generating a second traced curve "$C_{Hole}$" by tracing a periphery of the hole in each scanned image as shown in the first image of FIG. 10; subtracting the background region from the scanned image. As shown in the top three images of FIG. 10, with aid of the drawing software, the computing device 116 is configured to convert the initial image to several layers, each having a different gradient shade color (as shown in third image of top row of images in FIG. 10), thereby accurately distinguishing each of the delamination (for example, indicated in light color), damage initiation (for example, indicated in gray color), and the background region 1004 (for example, indicated in black color).

As shown in FIG. 10, separation of the areas further includes determining a delamination region 1008 by subtracting the second traced curve "$C_{Hole}$" from the first traced curve "C1"; tracing contours ($T_1$, $T_2$, $T_3$, ..., $T_N$ as shown in a third image of top row of images in FIG. 10) of peripheral damage within the delamination region (as shown in the third image of top row of images in FIG. 10), thus generating a plurality of third traced curves "T"; combining the first traced curve "C1" with the second traced curve "$C_{Hole}$", thus generating a composite curve "$C_{Comp}$" (as shown in the fifth image in the order of images in the bottom row of FIG. 10) representing the delamination region of each scanned image of each drilled hole; and applying shading 1010 (as shown in a sixth image in the order of images in the bottom row of FIG. 10) to the delamination region 1008, thus generating a shaded delamination region 1008.

Figure 12B:
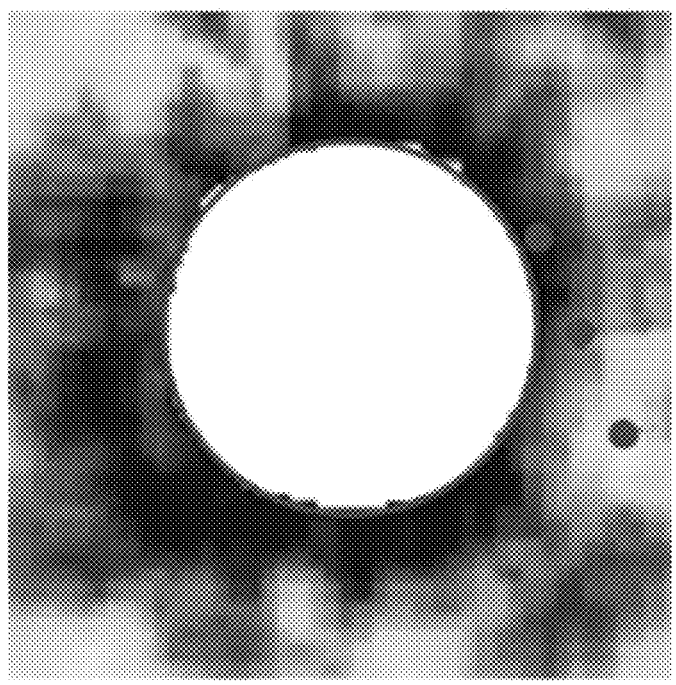
FIG. 12B shows a numerical simulation image depicting damages produced in drilling woven carbon fiber reinforced polymer (CFRP) composites, according to certain embodiments.
Figure 12A:
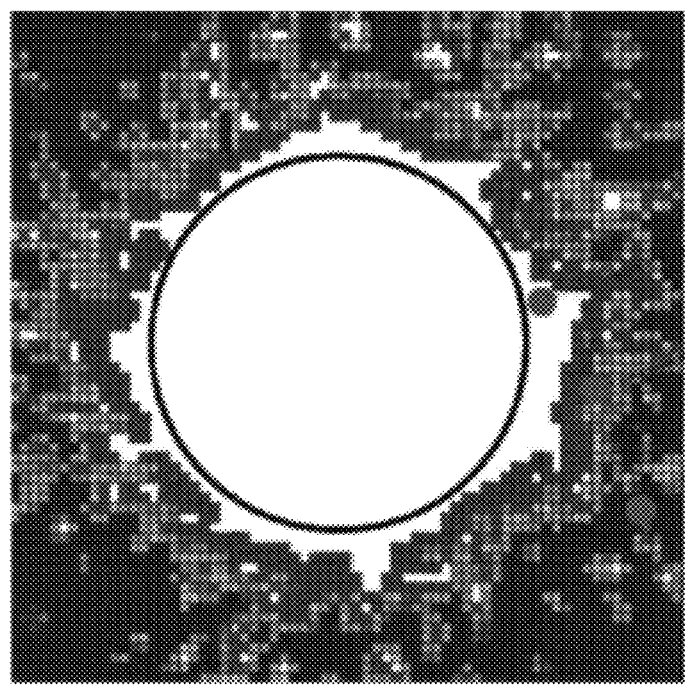
FIG. 12A shows a digital c-scan detection image depicting damages produced in drilling woven carbon fiber reinforced polymer (CFRP) composites, according to certain embodiments.

For example, through the CorelDraw utilities, "Quick Trace" tool may be used to convert the scanned image to several layers with different gradient shade colors. This stage accurately distinguishes among the complete delamination (lighter color), damage initiation (gray color) and intact regions (black color of a virgin material) compared to those obtained by a c-scan and a numerical simulation illustrated in FIG. 12A and FIG. 12B respectively. Further, a "Convert to Curves" tool of the CorelDraw utilities may be used to convert each layer to individual curve. Then, the background region 1004 (intact regions) and any other manufacturing defects away from the delamination and burr areas may be deleted.

The computing device 116 is further configured to calculate: (i) an area of a third circle "C3" (shown in FIG. 11), $A_{nom}$, from the nominal diameter, $D_{nom}$; (ii) an area of the shaded delamination region, $A_d$; (iii) a two-dimensional delamination factor, $F_a$, given by equation (4) below.

$$F_a = \frac{A_d}{A_{nom}} \quad (4)$$

The computing device 116 is further configured to calculate a maximum delamination area, $A_{max}$, from the maximum diameter, $D_{max}$; add the third circle "C3" as shown in the third image of FIG. 11 to the shaded delamination area; identify burr regions (dark shading) radiating from the delamination region into the third circle "C3"; determine a radius of each burr region from a center of the third circle "C3"; calculate each burr area from the radius of each burr region; and generate a total burr area, $A_b$, by summing the burr areas. Additionally, the computing device 116 calculates an adjusted delamination factor, $F_{da}$ (given by equation (5) below) and equivalent delamination factor, $F_{ed}$ (given by equation (6) below).

$$F_{da} = F_d + \frac{A_d(F_d^2 - Fd)}{A_{max} - A_{nom}} \quad (5)$$

$$F_{ed} = \frac{1}{D_{nom}} + \sqrt{\frac{4(A_d + A_{nom})}{\pi}} \quad (6)$$

For each of the plurality third traced curves "T", the computing device 116 is configured to measure a radius of a maximum periphery from a center of the third circle "C3"; calculate an area of the maximum periphery from the radius of the maximum periphery; subtract $A_{nom}$ from the area of the maximum periphery to determine a peripheral damage area; sum the peripheral damage areas to generate a maximum peripheral damage area, $A_p$; and calculate a peripheral delamination factor, $F_p$ and a burr delamination factor, $F_b$ based on below equations. In a non-limiting example, the area of the hole ($A_h$) and the maximum peripheral damage area, $A_p$, may be calculated with $10^{-6}$ mm$^2$ resolution using a Visual Basic Macros (VBM).

$$F_p = \frac{A_p}{A_{nom}} \quad (7)$$

$$F_b = \frac{A_b}{A_{nom}} \quad (8)$$

Therefore, all delamination and burr factors may be calculated as defined by the equations (1) through (8). The ACIP technique is calibrated in comparison to a typical standard rule that uses polygon shapes with known areas. A negligible error in a range of about 0.3% to about 0.8% was ascertained with the ACIP technique, hence rendering the technique reliable.

Testing the ACIP technique for different materials:

FIG. 13 and FIG. 14 illustrate digital scanned images of push-out delamination in drilling a quasi-transparent GFRP composite (FIG. 13) and an opaque GFRP composite (FIG. 14), respectively. Particularly, FIG. 13 and FIG. 14 compare the images obtained through a conventional technique (such as ImageJ software) (left side) with that of the ACIP technique (right side). The damages in these figures were photographed using digital scanners. Although the images in the two figures have undesirable shadows inside at an upper portion of the hole, the ACIP technique is capable of rendering clear images, as shown. In comparison to the image processing via the ImageJ software (represented by second and third image in the series of images), it can be observed that the ACIP technique provides well distinguished images, clearly indicates the damaged area, and accurately separates the delamination and the burr areas. A similar comparison can be observed in FIG. 14.

Figure 17:
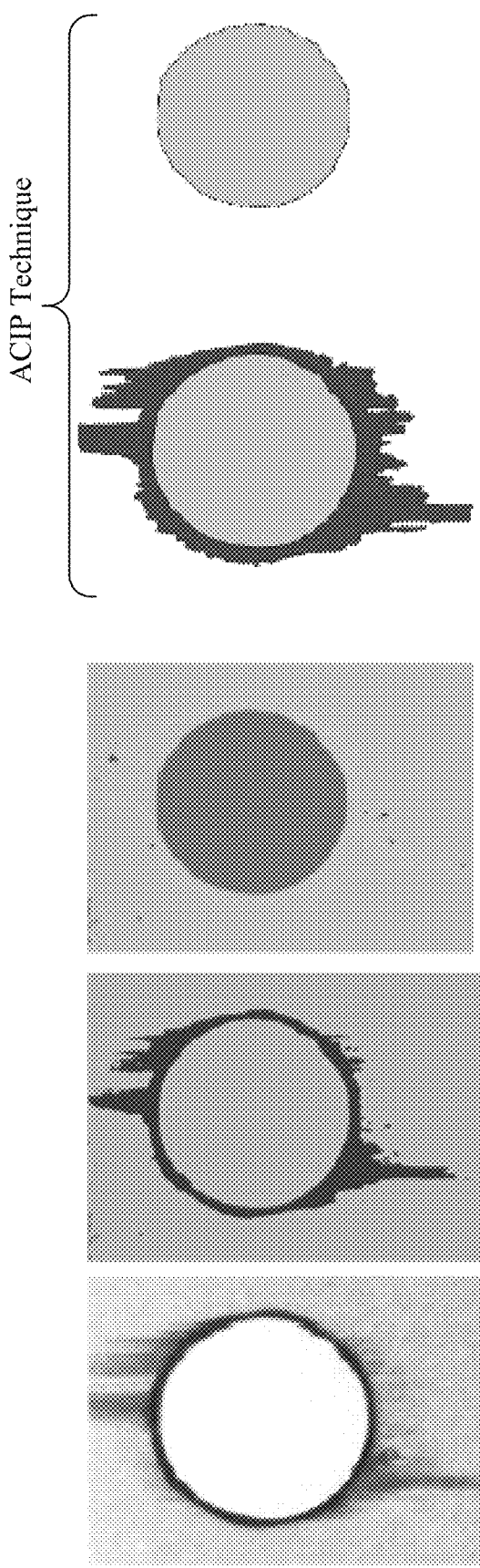
FIG. 17 shows X-ray image of push-out delamination in drilling the CFRE composites, according to certain embodiments.

The delamination and burr formation in drilling of the carbon fiber reinforced polymer (CFRP), as examples for the opaque composites, are also analyzed. FIG. 15 illustrates digital scanned images of push-out delamination produced in drilling holes in carbon fiber reinforced epoxy (CFRE) composites; FIG. 16 illustrates optical microscopy images of push-out delamination in drilling the CFRE composites; and FIG. 17 illustrates X-ray images of push-out delamination in drilling the CFRE composites. In comparison to the images obtained through the ImageJ software for binarization of the digital image via converting a grayscale image into a black-and-white image, the ACIP technique rendered images with high accuracy without missing any details in computed delamination and burr areas. A number of pixels representing the damaged area may vary during filtering the binary image to differentiate the grey and black areas.

In comparison with computational image processing, the damages in the ACIP technique were outlined by smooth digital curves that accurately describe and differentiate between the delamination and burr areas in drilling the CFRP/CFRE composites as against a finite element analysis and an image segmentation using a neuronal network approach.

FIG. 18 illustrates a table containing representative images of the delamination and burr factors measured at a speed of 14.3 m/min and different feeds. FIG. 19 illustrates another table containing representative images of delamination and burr factors measured at a speed of 27.5 m/min and different feeds. The representative images in the tables indicate that the ACIP technique successfully describes and accurately separates the delamination and burr areas. Particularly, the tables include the maximum concentric diameter of delamination area ($D_{max}$) and the minimum eccentric diameter ($D_{min}$), which are used for estimation $F_d$ and $F_{dmin}$ respectively. The tables also indicate images and values of the peripheral damaged area ($A_r$) and hole area ($A_h$) that are used for estimation delamination ($A_d$) area and burr ($A_b$) area.

From the tables of FIG. 18 and FIG. 19, it may be noticed that the damage area increases with the feed due to increasing thrust force for both cutting speeds. The delamination areas ($A_d$) at the drill entry are relatively lower than those at drill exit; the hole areas ($A_h$) at the drill entry are relatively smoother than those at the drill exit. The hole areas ($A_h$) at the drill entry are relatively smoother than those at the drill exit. The hole area decreases at an exit side and thus, the burr factor at the drill entry is lower than at the drill exit. The delamination and burr areas are relatively higher at the maximum speed (27.5 m/min) compared to the minimum speed (14.3 m/min). In FIG. 18, the first four examples (a) show peel-up delamination and the second four examples (b) show push-out delamination. Similarly, in FIG. 19, the first four examples (a) show peel-up delamination and the second four examples (b) show push-out delamination.

Figure 20:
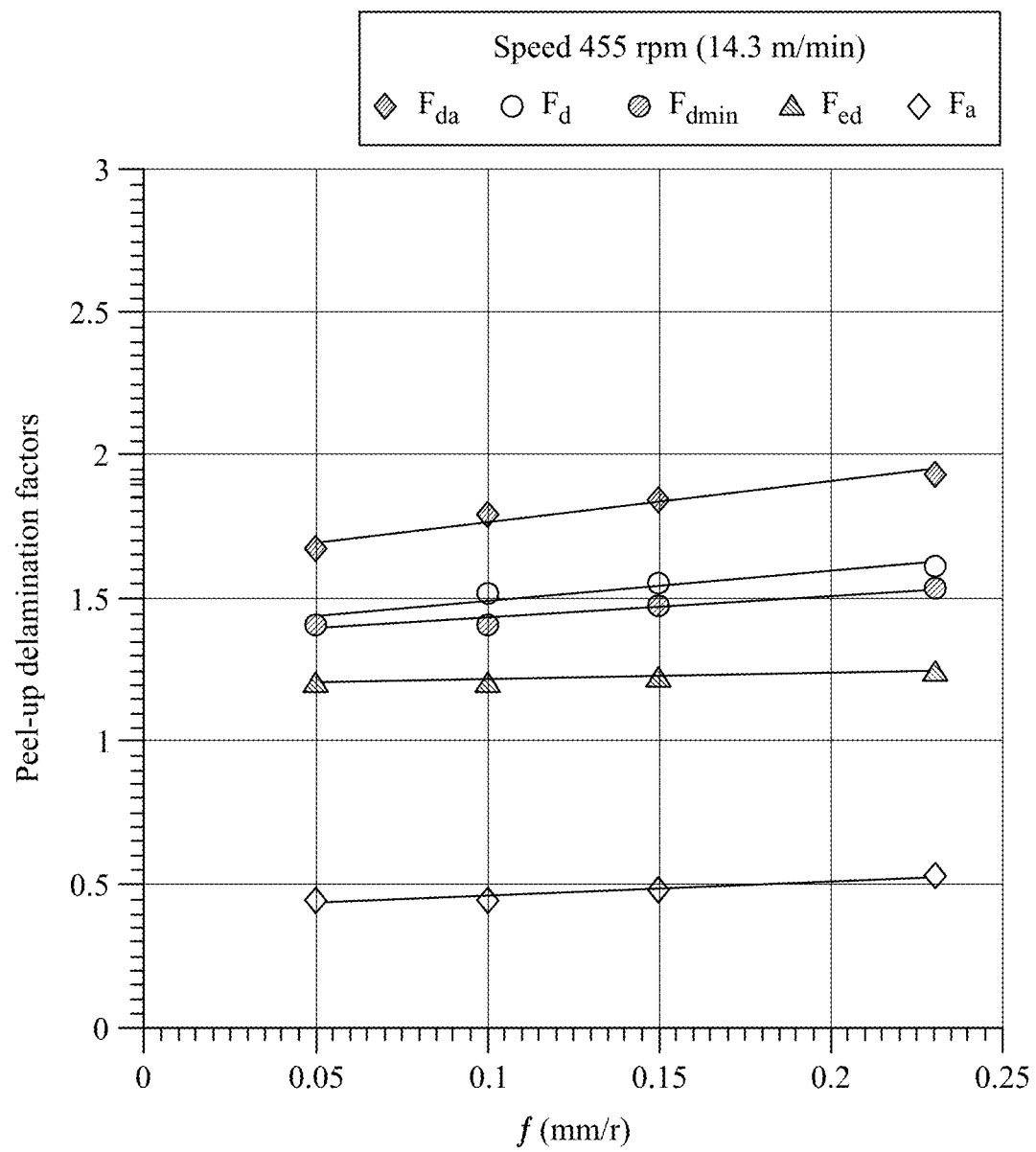
FIG. 20 illustrates the influence of the feed on peel-up delamination at a speed of 14.3 m/min, according to certain embodiments.
Figure 21:
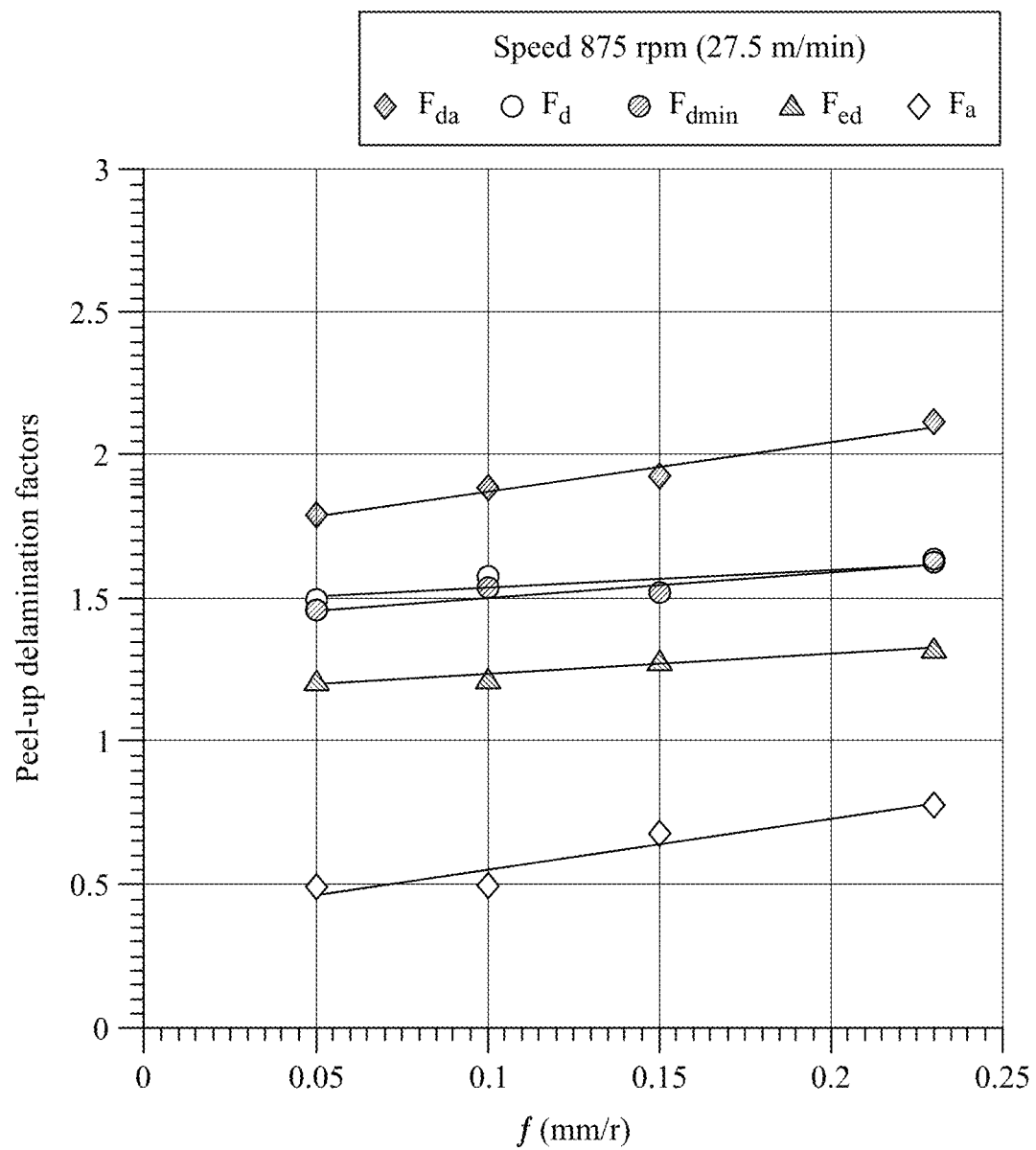
FIG. 21 illustrates the influence of the feed on peel-up delamination at a speed of 27.5 m/min, according to certain embodiments.

FIG. 20 and FIG. 21 illustrate the influence of the feed on peel-up delamination in the GFRP composite at a speed of 14.3 m/min (FIG. 20) and 27.5 m/min (FIG. 21). The delamination factors are presented via different forces, which include $F_a$, $F_{dmin}$, $F_{da}$, $F_{ed}$, and $F_p$.

Figure 22:
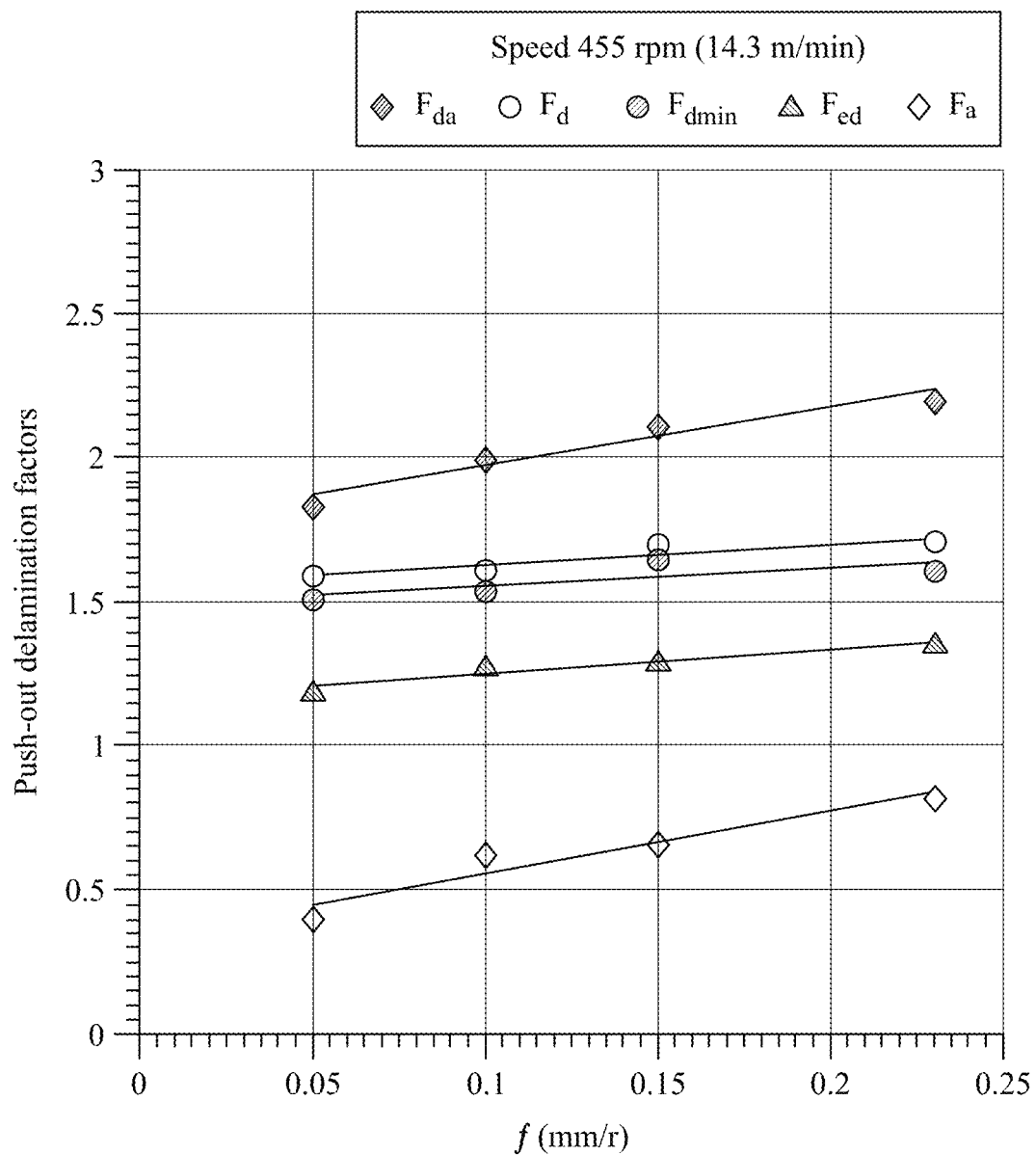
FIG. 22 illustrates the influence of the feed on push-out delamination at a speed of 14.3 m/min, according to certain embodiments.
Figure 23:
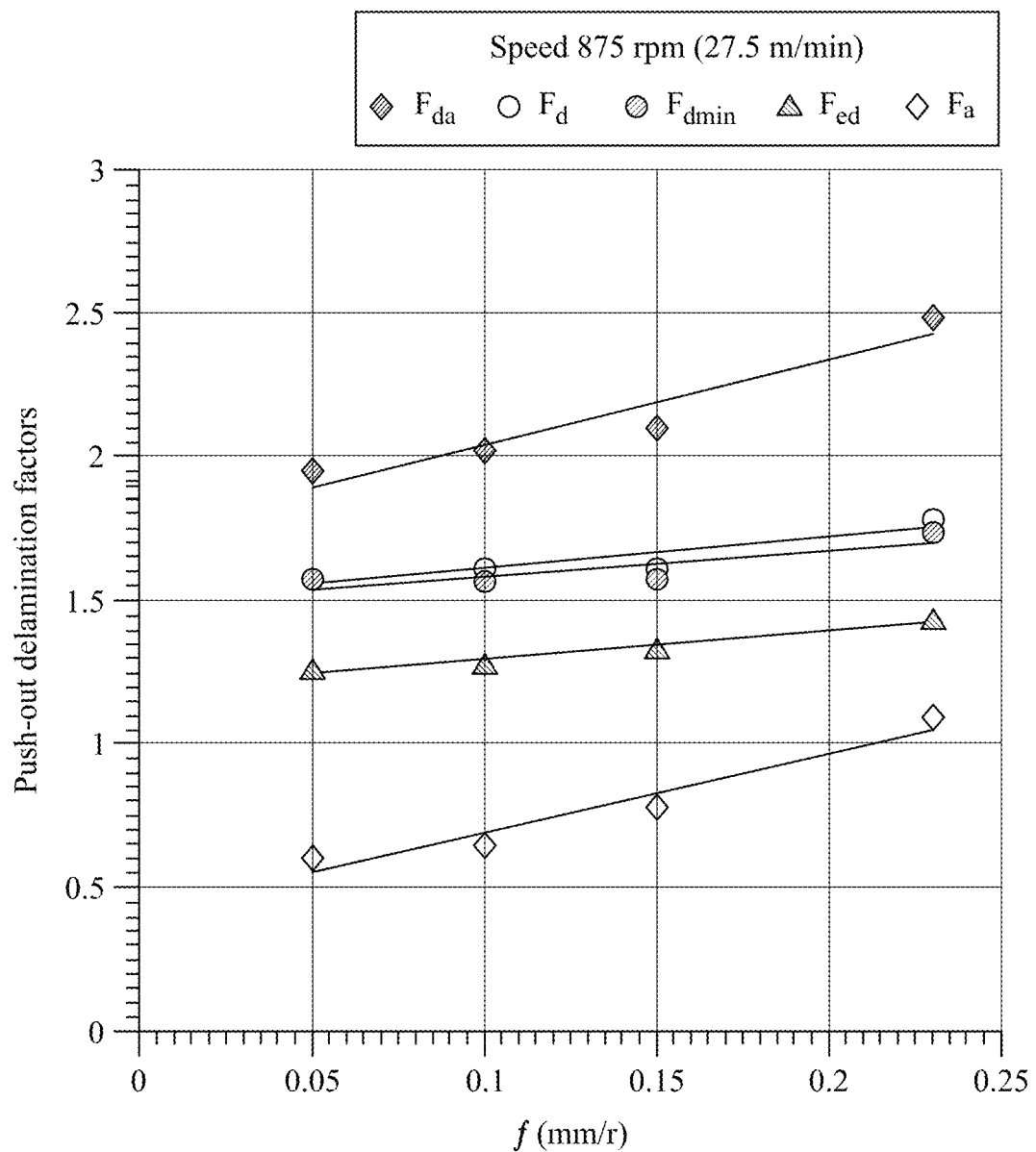
FIG. 23 illustrates the influence of the feed on push-out delamination at a speed of 27.5 m/min, according to certain embodiments.

FIG. 22 and FIG. 23 illustrate the influence of the speed of the feed on push-out delamination in the GFRP composite at a speed of 14.3 m/min (FIG. 22) and 27.5 m/min (FIG. 23). Values of the delamination factors increase with feed because of an increase in the thrust force. Although the thrust force reduces at higher cutting speed (such as 27.5 m/min), values of the peel-up and push-out delamination factors are increased as shown in FIG. 21 and FIG. 23. Similar results may be observed in Krishnaraj et al (Krishnaraj V, Prabukarthi A, Ramanathan A, Elanghovan N, Kumar M S, Zitoune R, Davim J P. "Optimization of machining parameters at high speed drilling of carbon fiber reinforced plastic (CFRP) laminates". Composites: Part B 2012; 43:1791-1799, incorporated herein by reference in its entirety). This is due to heating of the matrix, which reduces stiffness. Accordingly, a reduction in the stiffness owing to an increase in the temperature decreases the thrust force and increases delamination in drilling the FRP composites, affecting performance of the drilled holes. Also, it may be observed that push-up delamination is greater than peel-up delamination, as known in drilling the FRP composites. Such results may be exaggerated due to an absence of a backup supporting force, which can compensate of the produced thrust force during the drill process (See: Geng D, Liu Y, Shao Z, Lu Z, Cai J, Li X, Jiang X. Zhang D. "Delamination formation, evaluation, and suppression during drilling of composite laminates: A review". Composite Structures 2019; 216:168-186, incorporated herein by reference its entirety).

From the FIG. 20 to FIG. 23, it may be observed that the values of $F_d$ and $F_{dmin}$, which are measured via $D_{max}$ and $D_{mm}$, respectively, are marginally close. Such values demonstrate that the maximum delamination peak ($D_{max}$) is approximately located with the three peaks that are used for determining the $D_{min}$. This is consistent with the delamination images in tables of FIG. 15 and FIG. 16, which indicate that the damage initiation areas and delamination peaks are almost uniformly located around the drilled holes.

Figure 24:
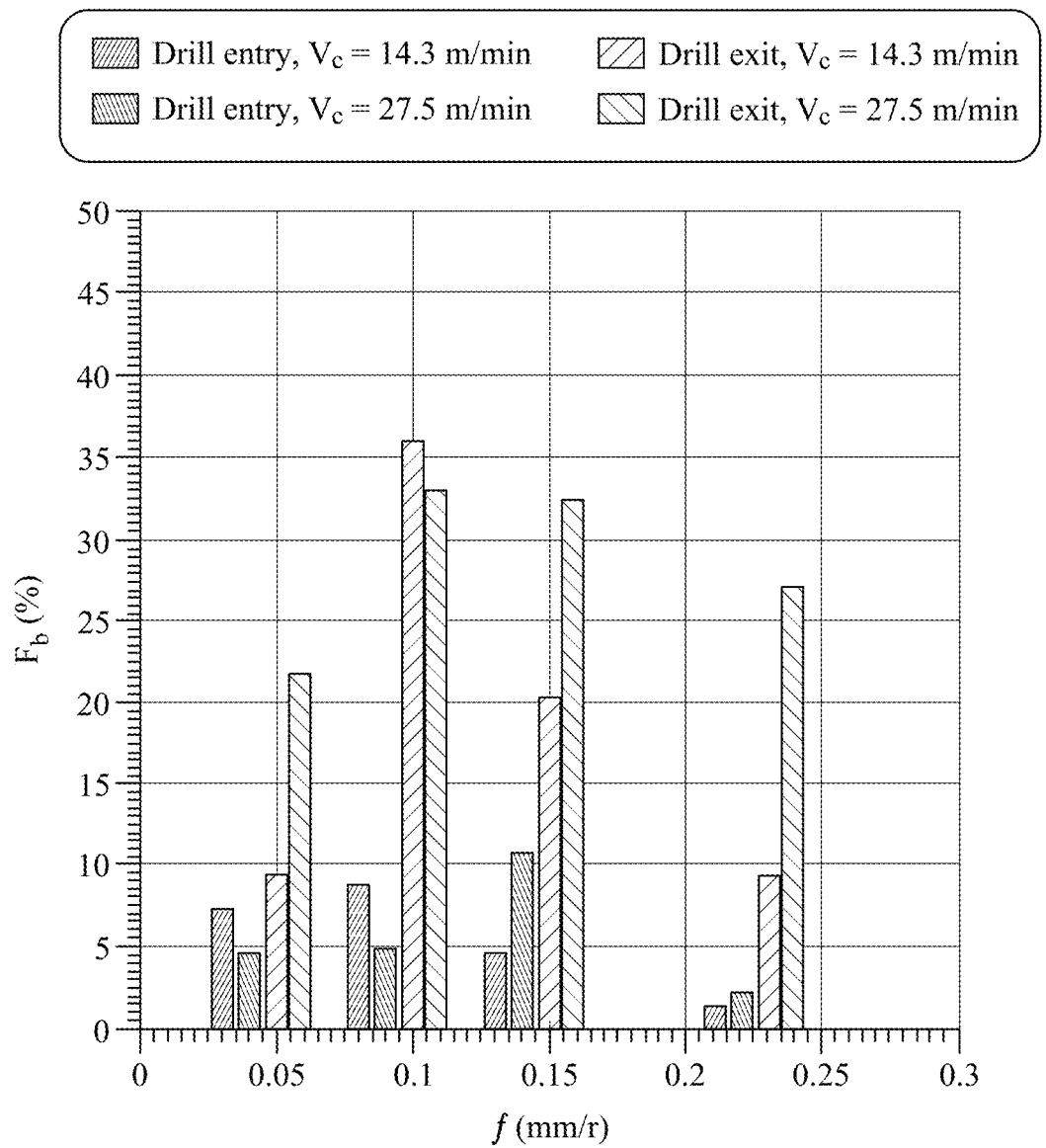
FIG. 24 illustrates the influence of the feed on burr factor at drill entry and exit for different speeds, according to certain embodiments.

FIG. 24 illustrates the influence of the feed on burr factor at drill entry and exit for different speeds. The burr factor at the drill exit is higher than the burr factor at the drill entry due to increase in accumulated heat at the drill exit relative to the drill entry. Thus, a push-down burr forms due to the fiber bending caused by the thrust force. From the FIG. 24, a maximum burr factor can be observed at the drill exit and the feed of 0.1 mm/r, whereas minimum burr factor can be observed at the maximum feed of 0.23 mm/r. Such values of the burr factor may be attributed to decrease in the accumulated heat with increase in the feed because of a reduced cutting time.

TABLE 2

Correlation coefficients of the delamination linear models for the peel-up delamination

| | Peel-up delamination | | | | | | | |
|---|---|---|---|---|---|---|---|---|
| | 14.3 m/min | | | | 27.5 m/min | | | |
| Model | a | c | R | $R^2$ | a | c | R | $R^2$ |
| $F_{da}$ | 1.417 | 1.622 | 0.982 | 0.965 | 1.749 | 1.705 | 0.990 | 0.980 |
| $F_{ed}$ | 0.194 | 1.190 | 0.979 | 0.9558 | 0.691 | 1.176 | 0.966 | 0.933 |
| $F_a$ | 0.472 | 0.416 | 0.978 | 0.957 | 1.763 | 0.376 | 0.967 | 0.934 |
| $F_p$ | 0.472 | 1.416 | 0.978 | 0.957 | 1.763 | 1.376 | 0.967 | 0.934 |
| $F_d$ | 1.051 | 1.382 | 0.960 | 0.921 | 0.612 | 1.483 | 0.810 | 0.656 |
| $F_{dmin}$ | 0.736 | 1.357 | 0.955 | 0.912 | 0.816 | 1.437 | 0.942 | 0.887 |

TABLE 3

Correlation coefficients of the delamination linear models for the push-out delamination

| | Push-out delamination | | | | | | | |
|---|---|---|---|---|---|---|---|---|
| | 14.3 m/min | | | | 27.5 m/min | | | |
| Model | a | c | R | $R^2$ | a | c | R | $R^2$ |
| $F_{da}$ | 2.079 | 1.763 | 0.979 | 0.959 | 2.956 | 1.753 | 0.955 | 0.912 |
| $F_{ed}$ | 0.842 | 1.162 | 0.959 | 0.919 | 1.016 | 1.201 | 0.978 | 0.956 |
| $F_a$ | 2.139 | 0.341 | 0.963 | 0.928 | 2.757 | 0.424 | 0.975 | 0.951 |
| $F_p$ | 2.139 | 1.341 | 0.963 | 0.928 | 2.757 | 1.424 | 0.975 | 0.951 |
| $F_d$ | 0.687 | 1.588 | 0.898 | 0.807 | 1.097 | 1.506 | 0.908 | 0.824 |
| $F_{dmin}$ | 0.634 | 1.490 | 0.769 | 0.592 | 0.912 | 1.496 | 0.835 | 0.697 |

The values of correlation coefficient (R) and coefficient of determination ($R^2$) between the measured delamination and those predicted using linear models are illustrated in Table 2 and 3. It can be observed from these tables that the adjusted delamination factor model ($F_{da}$) has the best fit (highest R and $R^2$) to the experimental measurements. Here, the $F_{da}$ considers the contributions of the maximum crack length ($D_{max}$) and the damage area ($A_d$) to overcome the drawbacks of the conventional delamination factor ($F_d$) and the two-dimensional delamination factor ($F_a$). In addition, the delaminated area ($A_d$) has a multiplication impact on the estimated values of the $F_{da}$, which have the highest indication of the delamination factor compared to the other models, as shown in FIG. 20 to FIG. 23.

Since the $F_d$ and $F_{dmin}$ are not accounted for in the damaged area, in some cases, these forces may not be suitable for representing the delamination. As shown in Table 2 and 3, the minimum values of $R^2$ for $F_d$ and $F_{dmin}$ are 0.656 and 0.592 respectively. On the other hand, the minimum value of $R^2$ for $F_{da}$, $F_{ed}$ and $F_a$ is 0.912. The results in Table 2 and 3 also show that the $F_p$ and $F_a$ have the same correlation coefficients (R) and coefficient of determination ($R^2$). The results in Table 2 and 3 also show that the $F_p$ have slope values "a" equal to those of the $F_a$ and higher intersection points "c". The parallelism of the two functions can also be demonstrated through the equality of the correlation coefficients (R) and coefficient of determination ($R^2$) of both delamination relationships. This is due to the difference between the damage areas of the $F_p$ and $F_a$ being a constant value equal to $A_{nom}$.

Figure 25A:
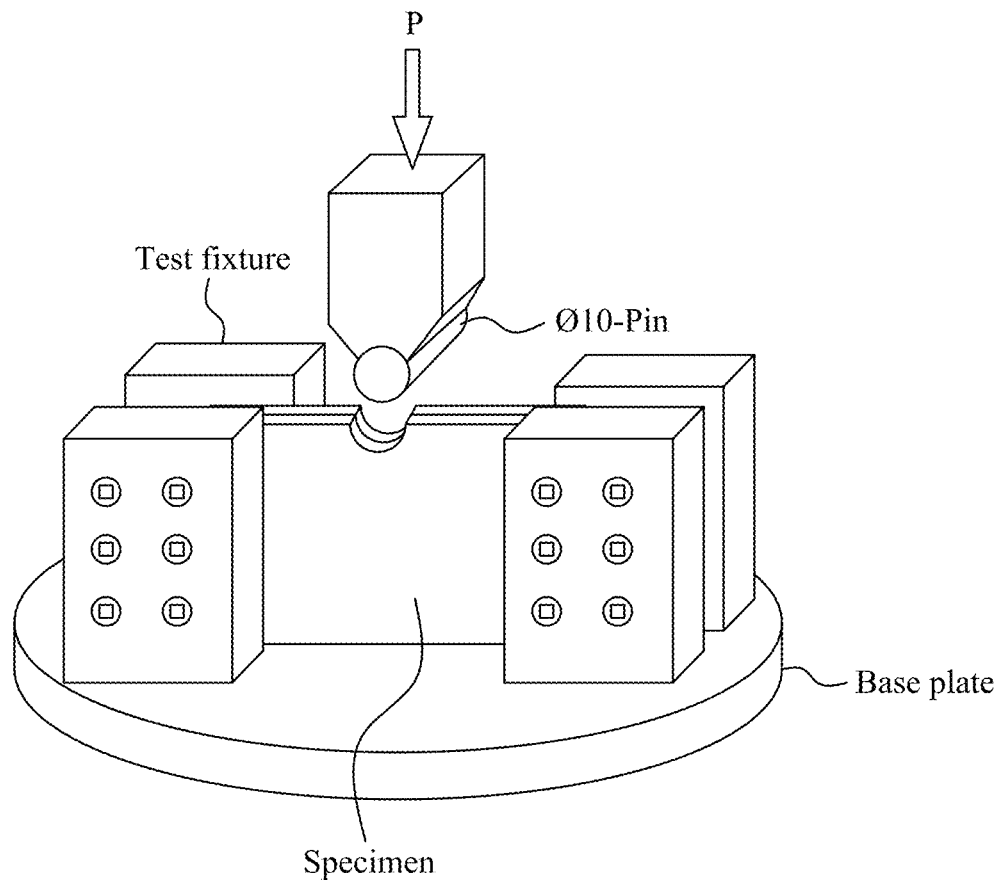
FIG. 25A is an exemplary pin-bearing test fixture, according to certain embodiments.
Figure 25B:
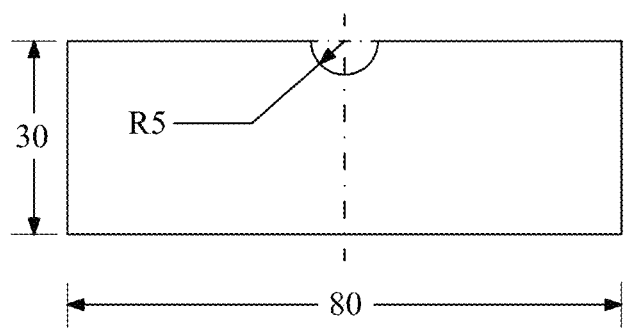
FIG. 25B illustrates dimensions of a bearing specimen used in the pin-bearing test fixture, according to certain embodiments.

FIG. 25A illustrates an exemplary pin-bearing test fixture. In one aspect, a bearing sample was examined to interpret the different failure mechanisms. For example, specimens with maximum diagonal of 5 mm were cut from the damaged area around the hole 106 (as shown in FIG. 25B). To improve conductivity, the SEM sample was bonded on a copper substrate using a carbon tab (smooth conductive tab of 260 μm) and coated with a thin film of gold (1 nm/min) inside a vacuum evaporator for 5 mins.

Since the main purpose of drilling holes in the composite laminates is to assemble the different composite structure components via bolted or riveted joints, determination of the load carrying capacity of such joints is very important in the practical applications. The failure of these joints was initiated by the bearing stress at bolt/hole contact area. Each drilled specimen (60 mm×80 mm) was cut from its center into two-bearing samples, as shown in FIG. 25B. The dimensions of the bearing specimens yielded w/d=8 and e/d=3, which satisfied the ASTM D 5961 requirements for the pin-bearing tests, where w is the specimen width (80 mm), d is the pin diameter (10 mm) and e is the distance between specimen centre to its edge (30 mm). A compression load was applied on the drilled area via hardened steel pin with nominal diameter of 10 mm, at rate of 1.0 mm/min. The bearing strength was calculated from the following equation $$\sigma b = \frac{P\max}{t * D}$$

where Pmax is the maximum load on the load-displacement curve in bearing test, t is the actual laminate thickness and D is the pin diameter (10 mm).

FIG. 25C shows representative fracture samples in the pin-bearing tests depicting the delamination of the GFRE layers, and top and front views of a bearing failure of the delaminated layers. The graph shown in FIG. 25D illustrates the influence of the feed rate on bearing strength. It may be observed from FIG. 25D that the values of bearing strength were significantly decreased with increasing feed due to increasing the thrust force and hence, the delamination damages of the drilled holes. A similar observation was made by Durao et al. (See: Durão L M P, Tavares J M R S, de Albuquerque V H C, Marques J F S, Andrade O N G. "Drilling Damage in Composite Material. Materials", 2014; 7: 3802-3819, incorporated herein by reference in its entirety). Although machining at higher feeds yields higher productivity, the drilled laminates have a lower mechanical resistance. In contrast, the bearing strength of the drilled holes at higher speed is higher than those machined at a lower speed. These observations may be attributed to reduction in internal damages as a result of decreasing the thrust force, as shown later in FIG. 30A.

Figure 25E:
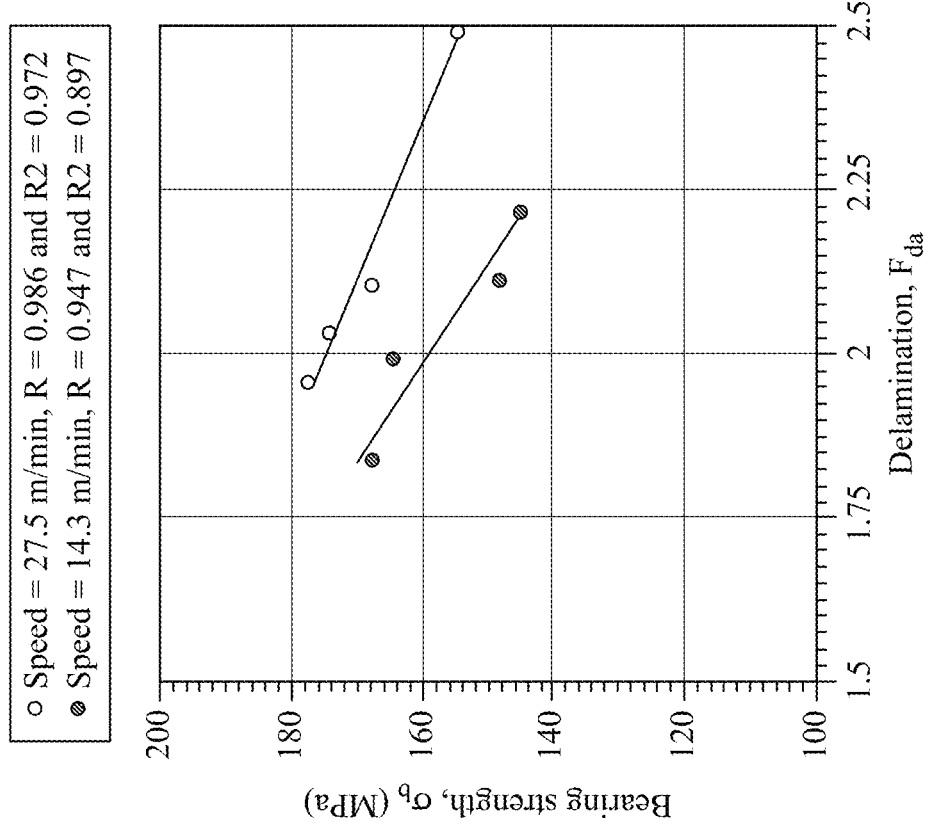
FIG. 25E illustrates a correlation between the bearing strength and the delamination factor, according to certain embodiments.
Figure 25D:
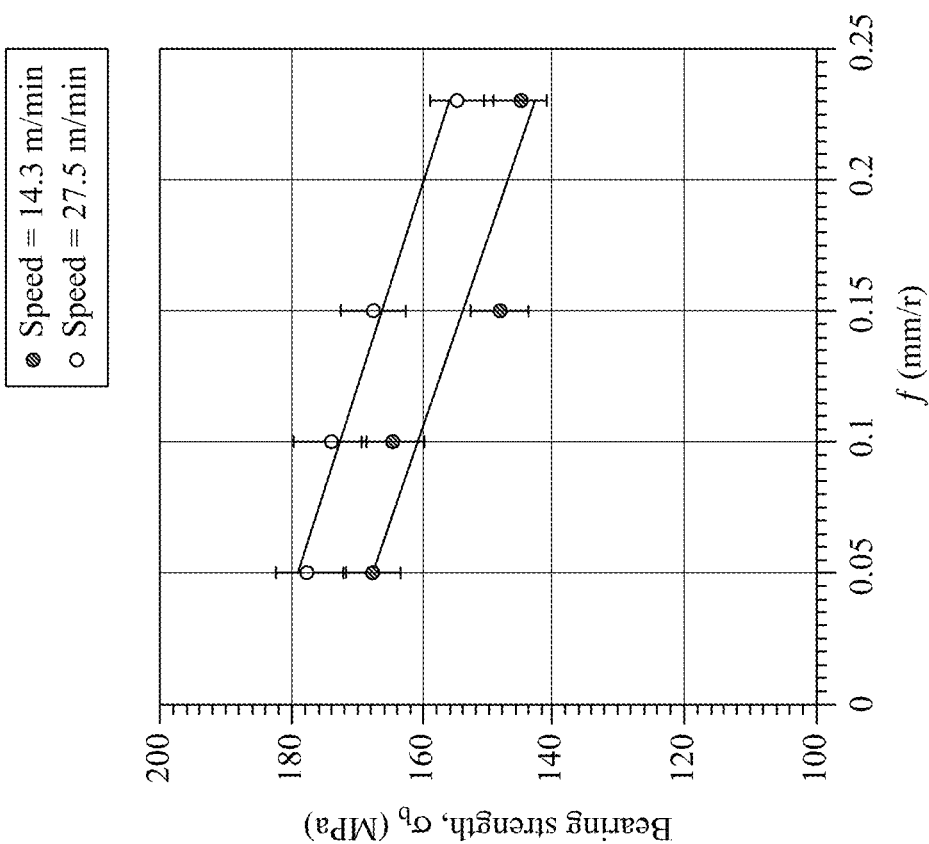
FIG. 25D illustrates the influence of the feed rate on bearing strength, according to certain embodiments.

The higher values of the correlation coefficients R and $R^2$ between the bearing strength and the delamination factor, shown in the graph of FIG. 25E, demonstrate the effect of delamination around the drilled holes on the reduction of bearing capacity of the mechanical fastening composite joints, which are extensively used for assembly purposes. Similar observation may be seen in Durão et al.

Figure 25F:
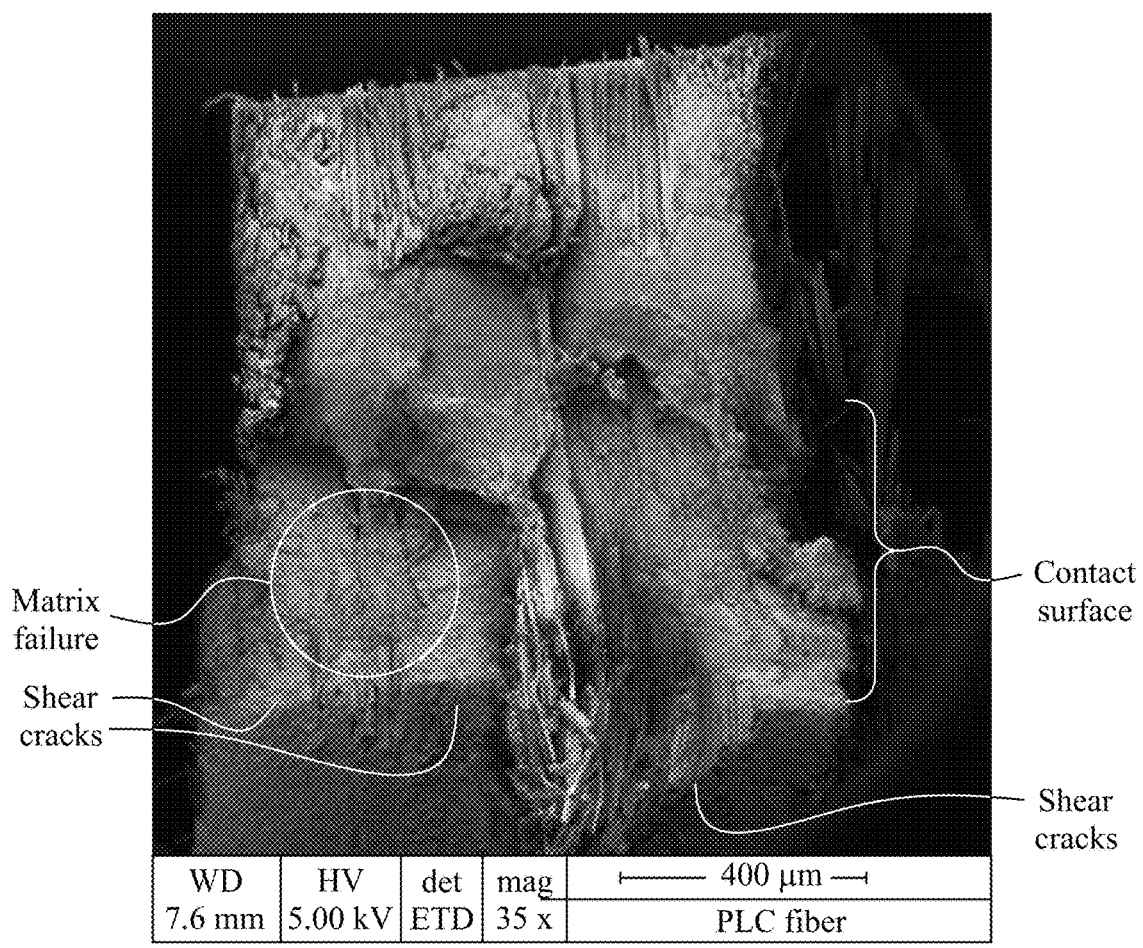
FIG. 25F shows an SEM image of fractures GFRP specimen in the pin-bearing test, according to certain embodiments.
Figure 25G:
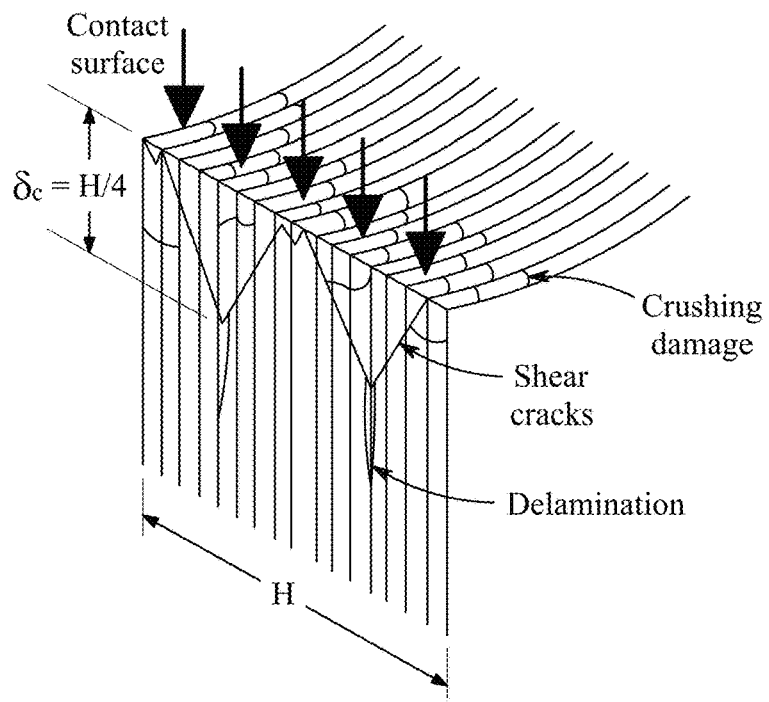
FIG. 25G illustrates schematic description of the failure mechanisms of damages in the pin-bearing test, according to certain embodiments.

FIG. 25F shows an SEM image of fractures in a GFRP specimen in the pin-bearing test. The pin-hole compressive loads results in interfacial damage that grows to form shear cracks at about 45° from the loading direction. The shear cracks are connected to indicate unstable delamination growth. At this point, laminates may lose their integrity and may become unable to carry higher bearing loads. A primary failure mode of the pin-loaded laminates occurs as the measured critical bearing distance δc from the bearing surface becomes equal to about one quarter of the laminate thickness, as shown schematically in FIG. 25G. Based on visual and microscopic examinations, it can be concluded that fiber kinking, fiber-matrix shearing, and matrix compression failure, FIG. 25F, are the main failure modes of the pin-bearing specimens. The bearing failure of the laminate include matrix cracks, fiber micro-buckling, delamination, and shear due to pin/hole contact compressive stress that results in a bearing failure mode (See: Galińska A. Mechanical Joining of Fiber Reinforced Polymer Composites to Metals—A Review. Part I: Bolted Joining. Polymers 2020; 12(10): 2252, incorporated herein by reference in its entirety).

Figure 26A:
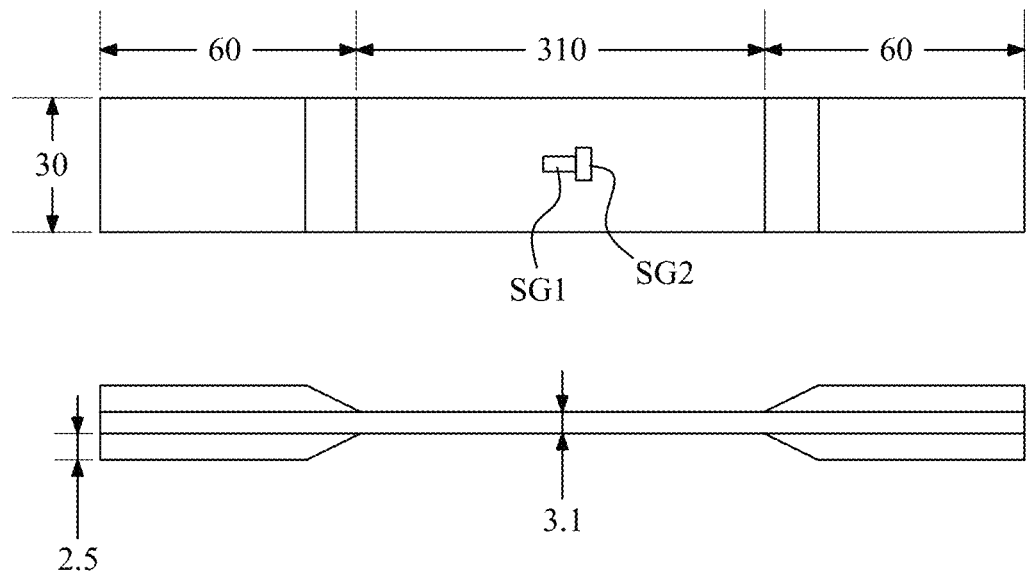
FIG. 26A illustrates the dimensions of a tensile specimen, according to certain embodiments.

FIG. 26A illustrates the dimensions of a tensile specimen. According to an aspect, the tensile strength tester 112 (FIG. 1) was configured to measure a tensile modulus and a Poisson's ratio of each block 102. In a non-limiting example, the tensile strength test may be performed on a servo hydraulic universal testing machine model Instron 8803, available from Instron, U.S.

A first strain gauge "SG1" was bonded at a midline on a first side of the drilled block 102, such that the first strain gauge "SG1" was oriented perpendicular to the drilled hole 106. A second strain gauge "SG2" was bonded at the midline on the first side of the drilled block 102, such that the second strain gauge "SG2" was oriented perpendicular to the first strain gauge "SG1". In an non-limiting example, the dimensions of the GFRE specimen may be 250×30×3.1 mm in accordance with ASTM D3039. Twenty-four specimens were tested to investigate the effect of drilling conditions on the notched strength (three specimens for each drilling condition). The specimens were clamped via serrated grips of the tensile testing machine with gripping length of about 60 mm.

A pulling force was attached to aluminum tabs on a first end of the drilled block 102, the first end being opposite to a second end. Further, a stationary clamp was attached to the aluminum tabs on the second end of the drilled block 102, the third side being parallel to the second side. By increasing the pulling force in increments, a tensile stress, σ, was measured by the first strain gauge "SG1" and a tensile strain, ε, was measured by the second strain gauge "SG2" and read at each increment. The pulling force was released when the drilled block 102 fractured and the tensile modulus, E, was calculated as:

$$E = \frac{\sigma}{\varepsilon} \quad (9)$$

Further, a first length, $L_1$, of the drilled block 102 between the first end and the second end was measured prior to subjecting the drilled block 102 to the pulling force and a change in the first length between the first end and the second end due to the pulling force at each increment was also measured. Similarly, a second length, $L_2$, perpendicular to the first length, was measured prior to subjecting the drilled block 102 to the pulling force and change in the second length, $dl_2$, due to the pulling force at each increment was also measured. A longitudinal strain and transverse strain were calculated as:

$$\varepsilon_1 = \frac{dl_1}{L_1} \quad (10)$$

$$\varepsilon_t = \frac{dl_2}{L_2} \quad (11)$$

Further, the Poisson's ratio, μ, was calculated as:

$$\mu = -\frac{\varepsilon_t}{\varepsilon_1} \quad (12)$$

Figure 26B:
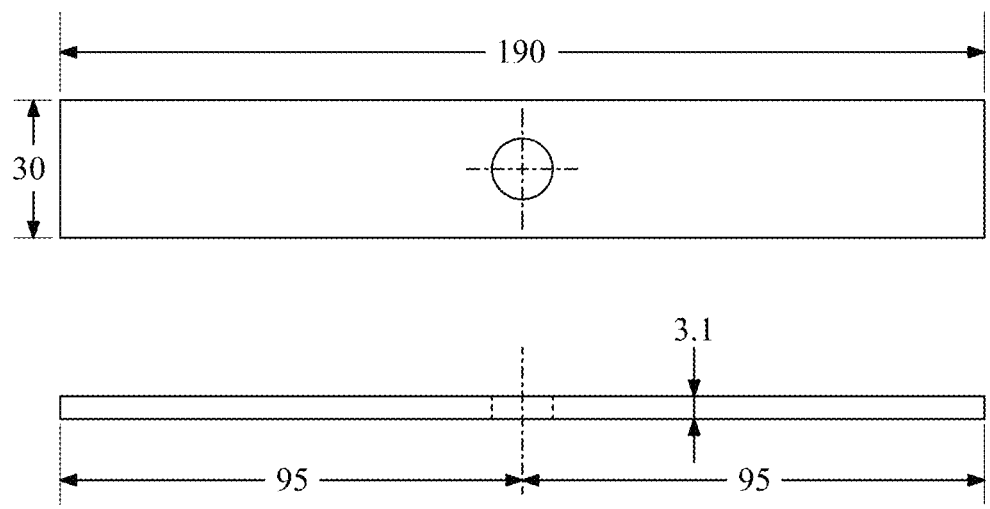
FIG. 26B illustrates the dimensions of a drilled specimen for determining notched strength, according to certain embodiments.

FIG. 26B illustrates the dimensions of a drilled specimen 2600 for determining notched strength. The drilled specimen 2600 shown in FIG. 26B has a length of 190 mm, a width of 30 mm and a thickness of 3.1 mm. A hole is drilled at a half-length distance, that is 95 mm, measured from one end of the drilled specimen 2600.

Figure 27:
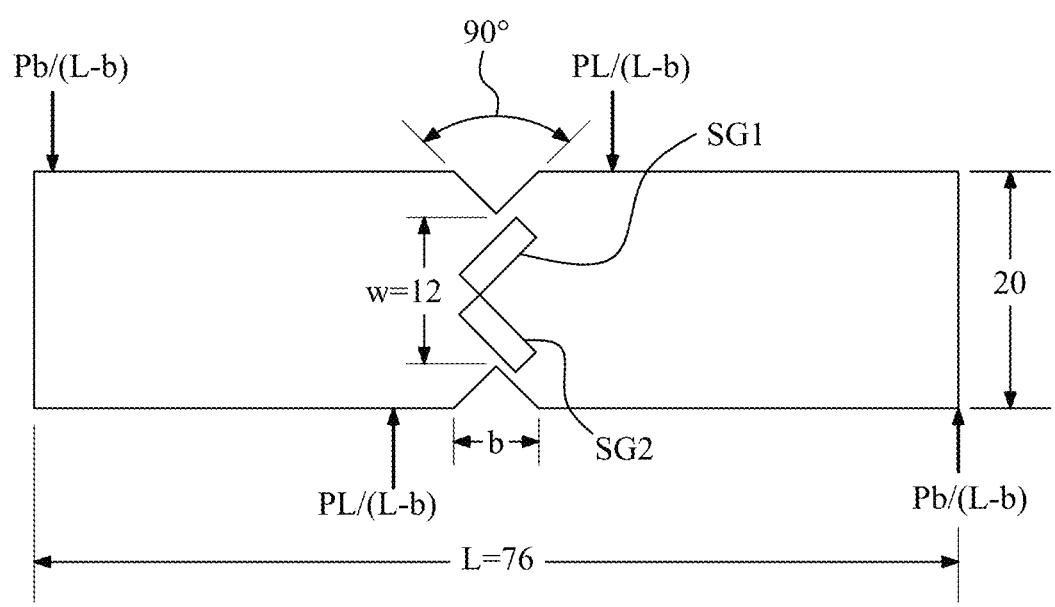
FIG. 27 illustrates a double V-notch specimen, according to certain embodiments.

FIG. 27 illustrates a double V-notch shear test. In an aspect, double V-notch shear test sample was cut to the dimensions as shown, corresponding to ASTM D5379.

Each of the forces indicated as "PL/(L–b)" was increased a maximum force "$P_{max}$" when the double V-notch shear test sample cracks. In an aspect, the forces may have a value of about 1.3 mm/min (0.050 in/min). The shear stress, $\tau_{xy}$, was calculated by:

$$\tau_{xy} = \frac{P_{max}}{A} \quad (13)$$

Further, a first shear strain, $\varepsilon_{-45}$, was measured with the first strain gauge "SG1" and a second shear strain, $\varepsilon_{+45}$, was measured with the second strain gauge "SG2" when the drilled block cracks. The shear strain, $\gamma_{xy}$, was calculated using $$\gamma_{xy} = \varepsilon_{-45} - \varepsilon_{+45} \quad (14)$$

Figure 28A:
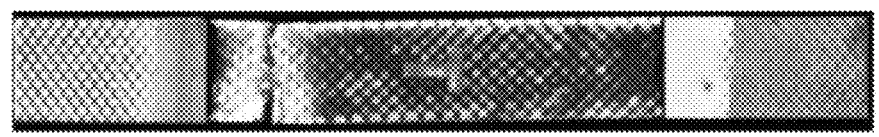
FIG. 28A illustrates SEM image of a fractured specimen in the tensile test, according to certain embodiments.
Figure 28B:
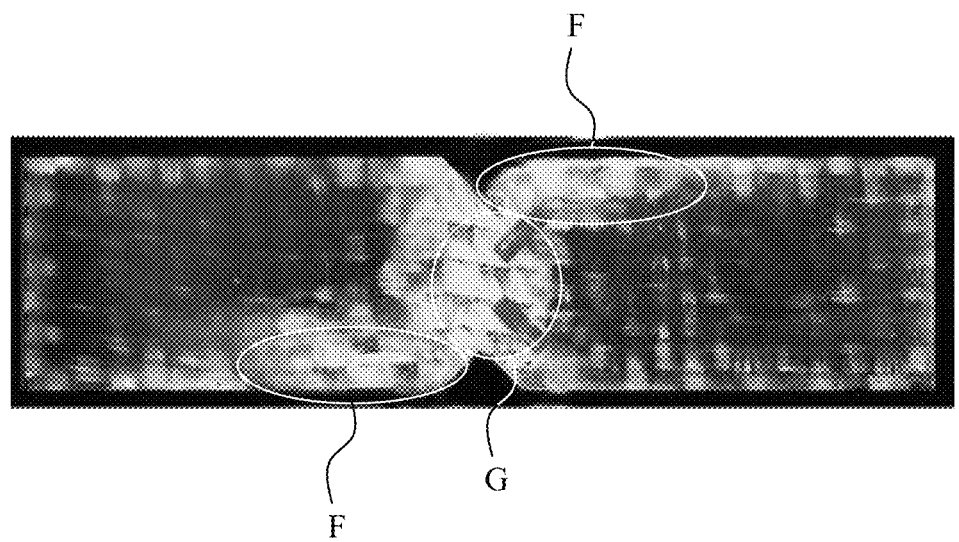
FIG. 28B illustrates SEM image of a fractured specimen in the in-plane shear test, according to certain embodiments.

FIG. 28A illustrates SEM image of a fractured specimen in the tensile test and FIG. 28B illustrates SEM image of a fractured specimen in the in-plane shear test. The damages were observed at the loading points near the V-notches 2700. The final fracture was due to the delamination along the roots of the V-notches 2700 as shown by the white areas, marked as regions "F" and region "G" in FIG. 28B.

Figure 28C:
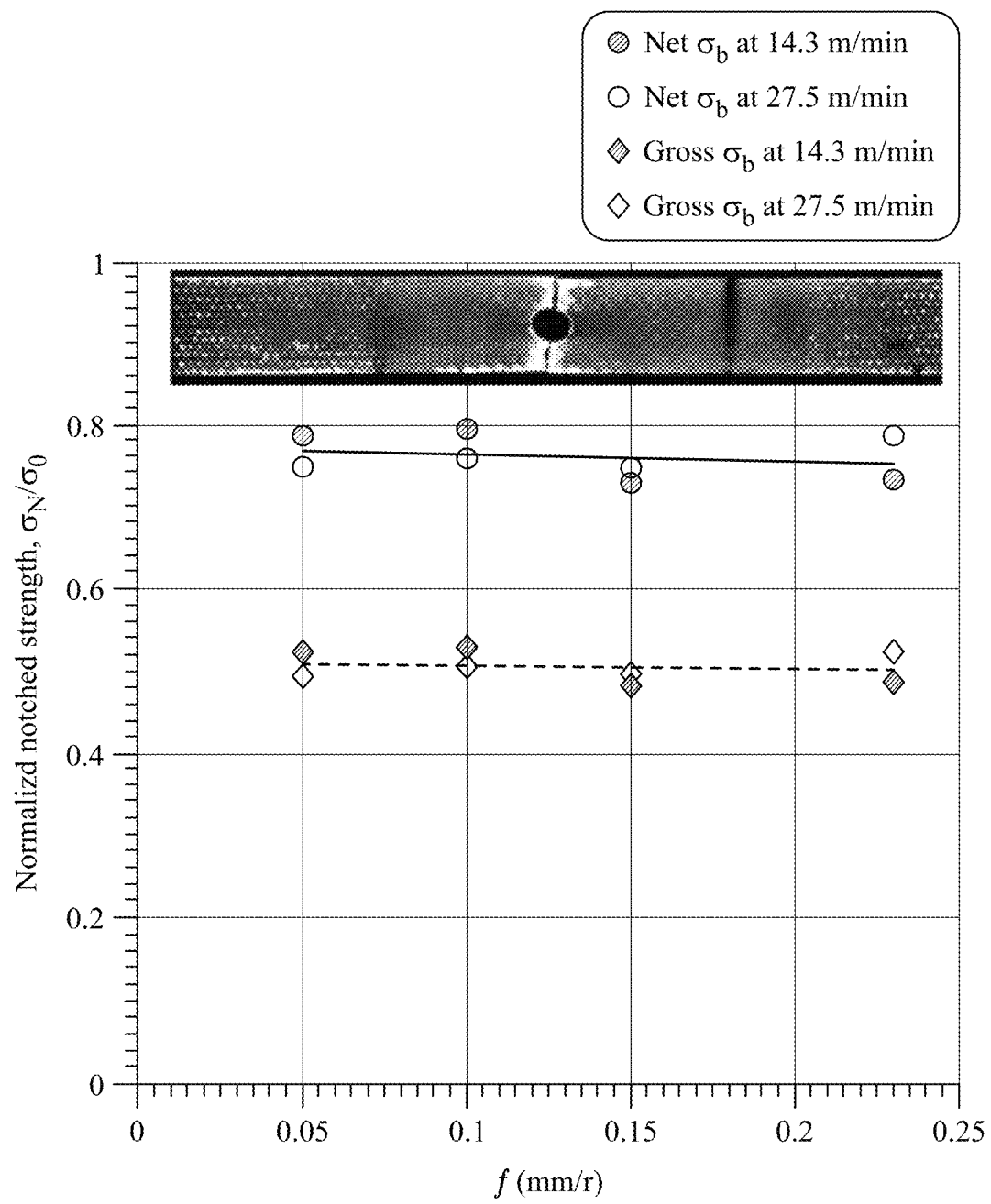
FIG. 28C is a graph illustrating the influence of the feed and the speed on normalized notched strength, according to certain embodiments.

The graph of FIG. 28C illustrates the influence of the feed and the speed on normalized notched strength. The notched strength was calculated based on net and gross-section areas, which was calculated as (w–d)t and (w·t) respectively, where, w is the specimen width, t is the thickness, and d is the hole nominal diameter. The net and gross notched strengths were obtained by dividing the maximum load to the corresponding cross-sectional area. The maximum load was obtained from the load-displacement curves as shown by the representative sample of FIG. 29A. It can be observed from the graph of FIG. 28C that the notched specimen failed catastrophically. FIG. 28C shows image of fractured notched specimen, which may be characterized by excessive de-bonded (brighter) spots started ahead of the drilled hole due to propagation of the maximum stress concentration towards the specimen edge. FIG. 28C also shows the variation of normalized notched strength versus the feeds at different cutting speeds. In this figure, the notched strength was normalized by the tensile strength of the unnotched strength ($\sigma_b$). The results shown in FIG. 28C shows that the feed and the cutting speed had a marginal effect on the notched strength. This result agrees with the results of Tagliaferri et al (See: Tagliaferri V, Caprino G, Diterlizzi A. "Effect of Drilling Parameters on The Finish and Mechanical Properties of GFRP Composites". Int. J. Mach. Tools Manufact. 1990; 30(1):77-84, incorporated by reference herein in its entirety).

Figure 29A:
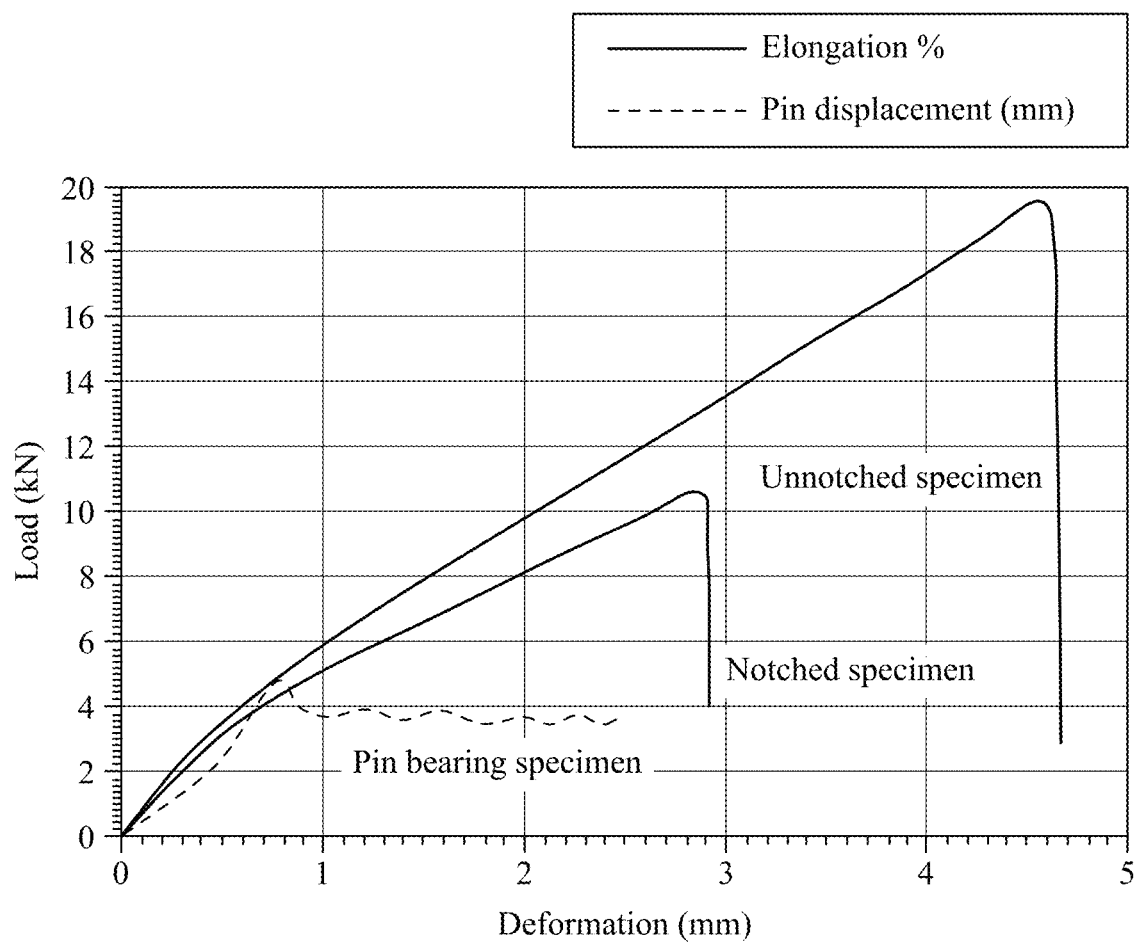
FIG. 29A is a graph illustrating representative samples of the load-deformation curves of unnotched, notched and bearing test specimens, according to certain embodiments.

The graph of FIG. 29A illustrates representative samples of the load-deformation curves of unnotched, notched and bearing test specimens. Specifically, FIG. 29A shows apparent load-deformation curves of the GFRP samples under tension (notched and unnotched) and bearing loads. The load-elongation curve of the unnotched (virgin) specimen can be divided into two portions. The first one is the linear behavior up to about 3 kN. In this portion the fiber and the matrix exhibited the same elastic deformation. A deviation from linearity was clearly observed at about 3 kN due to the microcracks initiation in the matrix, which has very low Young's modulus compared to the glass fiber. Therefore, the fiber was the main load-carrying components in the second stage. The fracture of tensile specimens was characterized by excessive fiber/matrix debonded (brighter) spots distributed along the specimen, FIG. 28A, which are visually observed at about 75% of the ultimate loads. This was attributed to the interlaced curved warp and weft fibers have different elastic properties compared to the matrix polymer. It was observed that the specimen fractured in a quasi-brittle manner, which was characterized by a sudden drop at the maximum load. The ultimate tensile strength was calculated at a peak load and an average value of five measurements are illustrated in Table 4. The Poisson's ratio and the Young's modulus were estimated from the stress-true strain relationships. The stress was estimated by dividing the load in FIG. 29A by the actual cross-sectional area of the specimen, whereas the true strain was obtained from the strain gauges SG1, SG2.

required. The noises of the torque and thrust force were filtered using the running average function. The results show that the filtered data of the thrust force still had large oscillations. This was due to the contacting of the cutting edges, warp, and weft fibers by different drill bit orientations. In addition, the interlacing of warp-weft yarn in a regular pattern style results in high stress concentrations resulting in crack initiation points, which significantly affects the cutting forces within a single ply. The other possible causes of the oscillating signals include the heterogeneous nature of the FRP composites, and the various thermal properties of the matrix and fibers (See: Choudhury M R, Srinivas M S, Debnath K. "Experimental investigations on drilling of lignocellulosic fiber reinforced composite laminates". Journal of Manufacturing Processes 2018; 34:51-61, incorporated herein by reference in its entirety).

After the chisel edge penetrated the workpiece surface, the thrust force was increased with a lower rate relative to the elastic initial portion due to the gradual increase of the uncut chip cross-sectional area (A=D·f/4) up to about 3 mm. This depth was equal to the approach allowance of the drill point with angle of 118°=(D/2)/tan(118°/2)=3 mm. As the drill point approached the last layer, at a 3 mm depth, the thrust force gradually slowed down till the chisel edge exited the workpiece at drilling depth of 3.1 mm. This behavior demonstrated that there was a decrease in the specimen stiffness at the last 0.1 mm due to raising the cutting temperature. After the drilling depth reached 3.1 mm (specimen thickness), a sharp decrease of the thrust forced was observed up to the end of drilling cycle owing to decreasing the contact length of the cutting lips with respect to the workpiece.

Figure 29B:
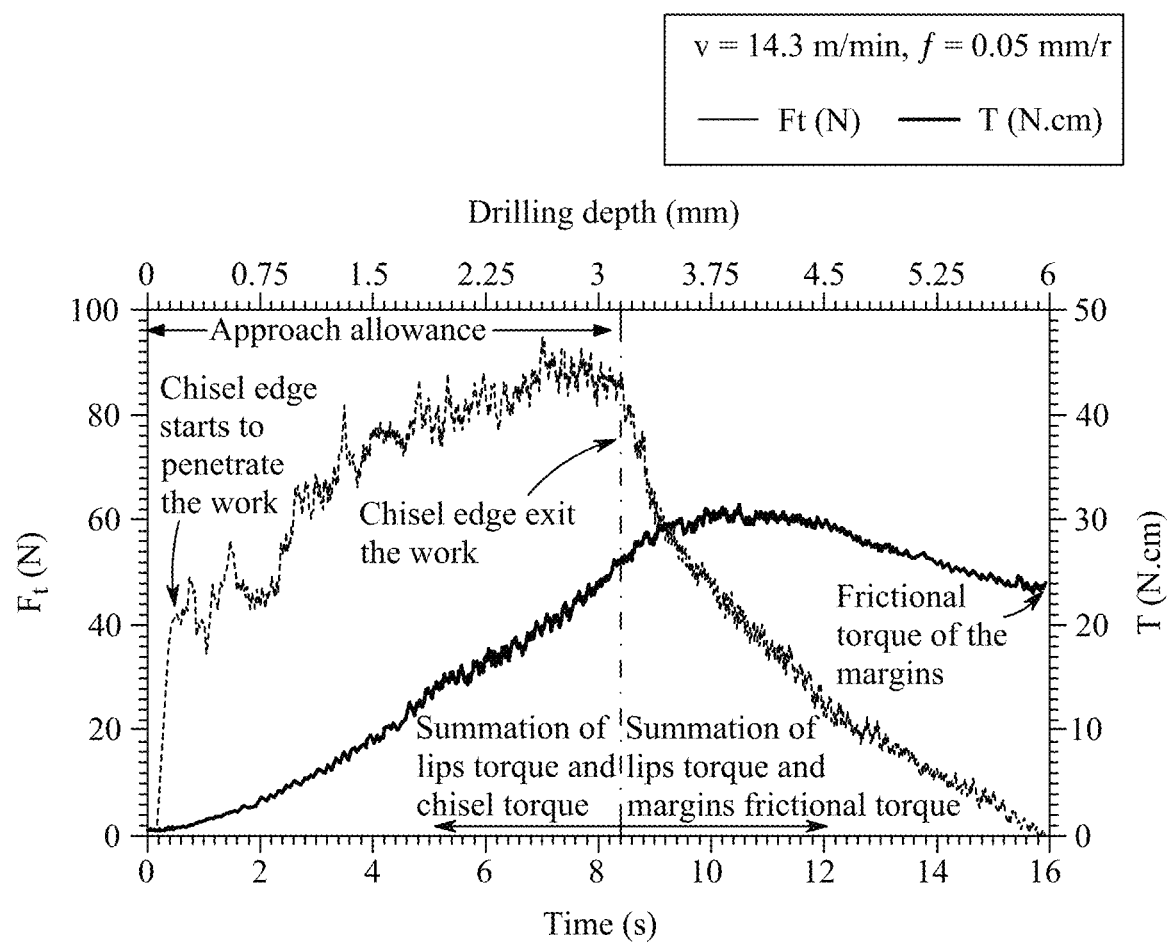
FIG. 29B illustrates representative sample of an evolution of cutting forces against time in drilling of GFRP composites, according to certain embodiments.

It may be observed from FIG. 29B that the torque gradually increased up to the maximum value at about 3.9

TABLE 4

Mechanical properties and standard deviation (SD) of woven GFRP composites

| Poisson's ratio | | Young's modulus | | Tensile strength | | Shear modulus | | Shear strength | | $G_{IC}$ | | $G_{IIC}$ | |
|---|---|---|---|---|---|---|---|---|---|---|---|---|---|
| $\upsilon 12 = \upsilon 21$ | SD | GPa | SD | MPa | SD | GPa | SD | MPa | SD | J/m$^2$ | SD | J/m$^2$ | SD |
| 0.295 | 0.015 | 16.05 | 0.116 | 203.86 | 4.215 | 3.78 | 0.123 | 28.04 | 1.86 | 270 | 6.4 | 513.1 | 10.3 |

FIG. 29B is a graph illustrating a representative sample of the evolution of cutting forces against time in drilling of GFRP composites at a feed of 0.05 mm/r and a speed of 14.3 m/min. A first portion in the thrust force-time (displacement) curve behaves in an elastic fashion up to about 41 N (45% of the peak value). The high elastic initial force is attributed to the zero-center speed of the chisel edge with large negative rake angle)(−50° which tends to extrude the material, instead of cutting through it. Tsao and Hocheng (See: Tsao C C, Hocheng H. "The effect of chisel length and associated pilot hole on delamination when drilling composite materials". Int. J. Mach. Tools Manuf. 2003; 43: 1087-1092, incorporated herein by reference in its entirety) noticed that in drilling the woven CFRP samples using 10 mm HSS drill and pre-drilling a pilot hole, the chisel edge contributed 40% to 50% of the maximum thrust force.

It may be observed from FIG. 29B that after the chisel edge penetrated the workpiece, the thrust force and torque curves had relatively high oscillating noise signals, which was attributed to the vibration of machine-fixture-tool-work system, hence filtering of the experimental data is often mm, that is, after the chisel edge exited the workpiece. The total torque up to drilling depth of 3.1 mm (specimen thickness) is the summation of the torque of the chisel edge and the cutting lips (See: Shan C, Zhang S, Zhang M, Qin K. "A prediction model of thrust force for drilling of bidirectional carbon fiber-reinforced carbon matrix composites". Science Progress 2020; 103(2) 1-22, incorporated herein by reference in its entirety). After the chisel edge exited the workpiece, the total torque measured may be equal to the summation of the cutting lips torque and the frictional torque of the margins with the machined surface. The torque was observed to gradually increase after the chisel edge exited the workpiece up to a drill depth of 3.9 mm. After this drilling depth, the torque gradually decreased until the cutting lips exited the workpiece at a drill depth of 6 mm. At this instant, the total torque was equal to the frictional torque of the margins with the machined hole wall.

Figure 30B:
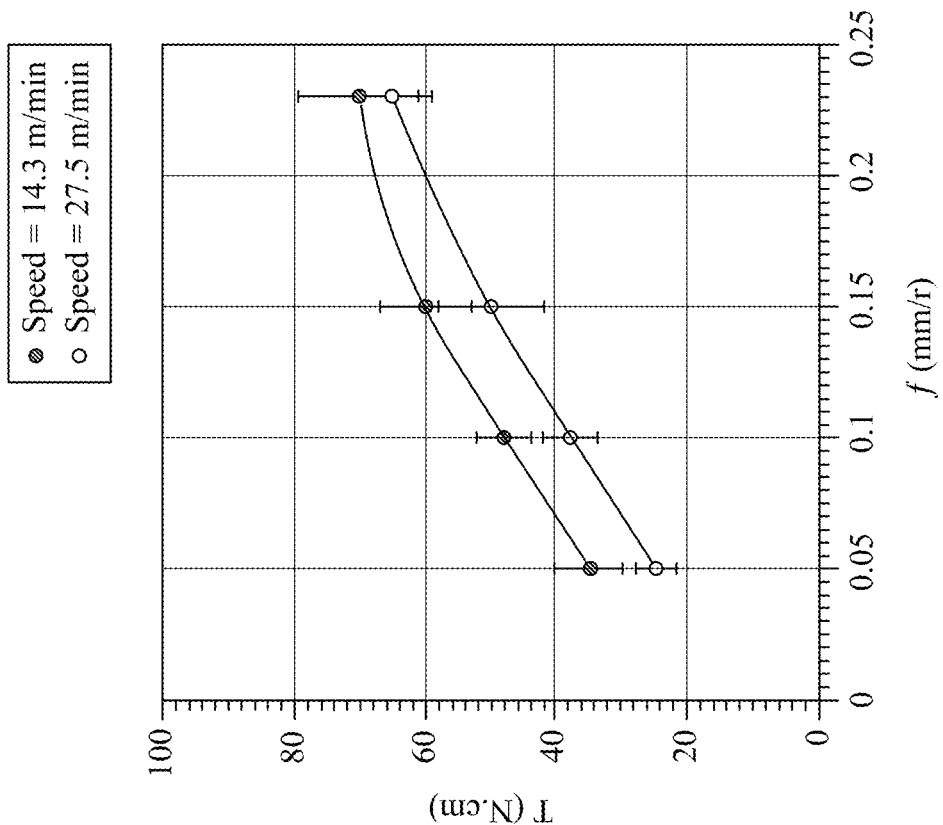
FIG. 30B illustrates the influence of the feed rate on a push-out, according to certain embodiments.
Figure 30A:
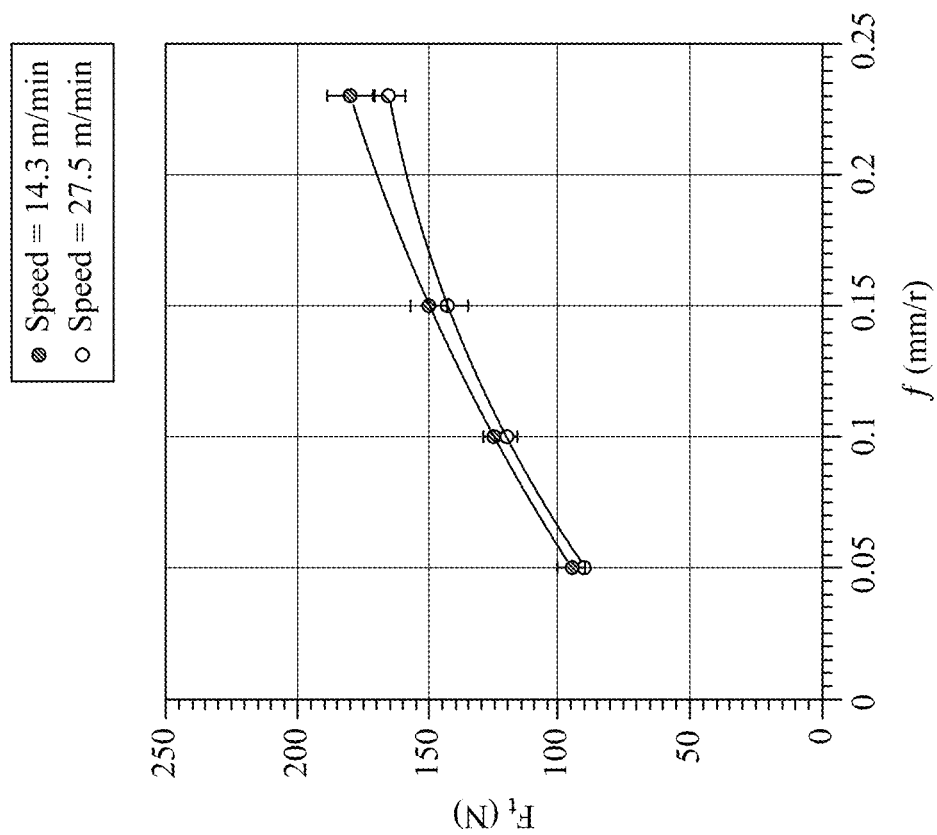
FIG. 30A illustrates the influence of the feed rate on the thrust force, according to certain embodiments.

FIG. 30A illustrates the influence of the feed rate on the thrust force and FIG. 30B illustrates the influence of the feed rate on a push-out. FIG. 30A and FIG. 30B are graphs showing that the thrust force and torque increased with the feed due to an increase in the cross-section area of the uncut chip (A=D·f/4). It may be observed from FIG. 30A that the thrust force was lower at the higher cutting speed (27.5 m/min) due to an increase in the cutting temperature, which decreased the stiffness of the workpiece. Increasing the cutting temperature with cutting speed was supported by the poorer thermal conductivity of polymeric composites. The accumulated heat about the drill edges caused matrix softening and hence, dry sliding may have occurred due to the self-lubricating ability of carbonous materials of the epoxy matrix which led to reduction in the friction torque of the chisel edge, cutting lips, and margins. Therefore, the cutting torque was decreased at higher cutting speed as shown in FIG. 30B. The effects of the cutting speed and the feed on the cutting temperature may have resulted in varied behaviors for thrust force and torque, which reflect the complexity of machining viscoelastic, heterogeneous, and anisotropic FRP composite materials.

Figure 31:
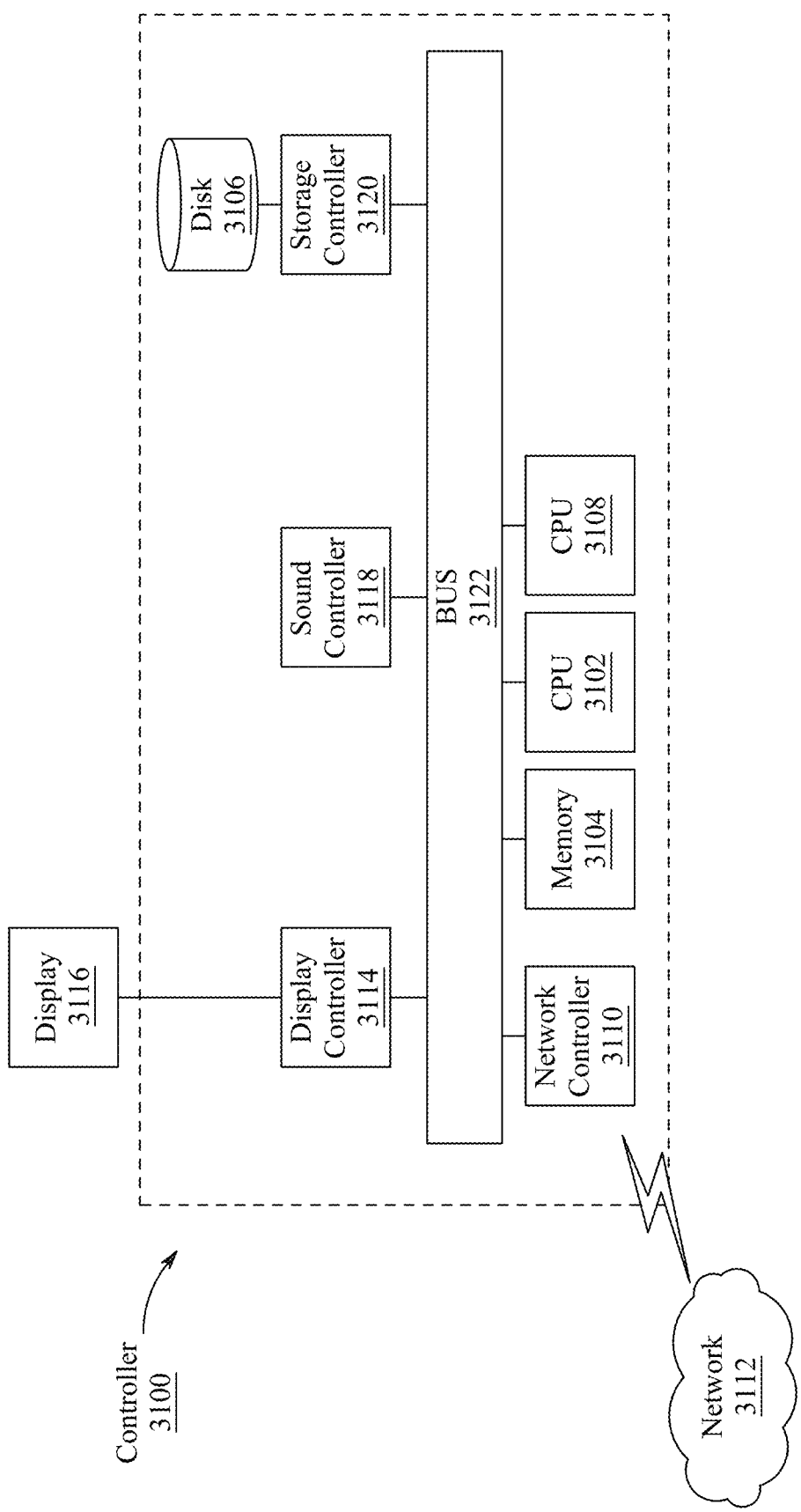
FIG. 31 is an illustration of a non-limiting example of details of computing hardware used in the computing system, according to certain embodiments.

Next, further details of the hardware description of the computing device 116 of FIG. 1 according to exemplary embodiments is described with reference to FIG. 31. In FIG. 31, a controller 3100 is described as representative of the computing device 116 which includes a CPU 3102 which performs the processes described above/below. The process data and instructions may be stored in a memory 3104. These processes and instructions may also be stored on a storage medium disk 3106, such as a hard drive (HDD) or portable storage medium or may be stored remotely.

Further, the claims are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the computing device communicates, such as a server or computer.

Further, the claims may be provided as a utility application, background daemon, or component of an operating system, or combination thereof, executing in conjunction with CPU 3102, 3108 and an operating system, such as Microsoft Windows 7, Microsoft Windows 10, UNIX, Solaris, LINUX, Apple MAC-OS, and other systems known to those skilled in the art.

The hardware elements in order to achieve the controller 3100 may be realized by various circuitry elements, known to those skilled in the art. For example, the CPU 3102 or CPU 3108 may be a Xenon or Core processor from Intel of America or an Opteron processor from AMD of America or may be other processor types that would be recognized by one of ordinary skill in the art. Alternatively, the CPU 3102, 3108 may be implemented on an FPGA, ASIC, PLD or using discrete logic circuits, as one of ordinary skill in the art would recognize. Further, the CPU 3102, 3108 may be implemented as multiple processors cooperatively working in parallel to perform the instructions of the inventive processes described above.

The controller 3100 also includes a network controller 3110, such as an Intel Ethernet PRO network interface card from Intel Corporation of America, for interfacing with network 2612. As can be appreciated, the network 3112 can be a public network, such as the Internet, or a private network such as an LAN or WAN network, or any combination thereof and can also include PSTN or ISDN sub-networks. The network 3112 can also be wired, such as an Ethernet network, or can be wireless such as a cellular network including EDGE, 3G and 4G wireless cellular systems. The wireless network can also be WiFi, Bluetooth, or any other wireless form of communication that is known.

The controller 3100 further includes a display controller 3114, such as a NVIDIA GeForce GTX or Quadro graphics adaptor from NVIDIA Corporation of America for interfacing with display 2616, such as a Hewlett Packard HPL2445w LCD monitor. A sound controller 3118 is also provided in the controller 3100, such as Sound Blaster X-Fi Titanium from Creative, to interface with speakers/microphone thereby providing sounds and/or music.

A general purpose storage controller 3120 connects the storage medium disk 2606 with a communication bus 2622, which may be an ISA, EISA, VESA, PCI, or similar, for interconnecting all of the components of the controller 2600. A description of the general features and functionality of the display 3116, the display controller 3114, the storage controller 3120, the network controller 3110, and the sound controller 3118 is omitted herein for brevity as these features are known.

Figure 32:
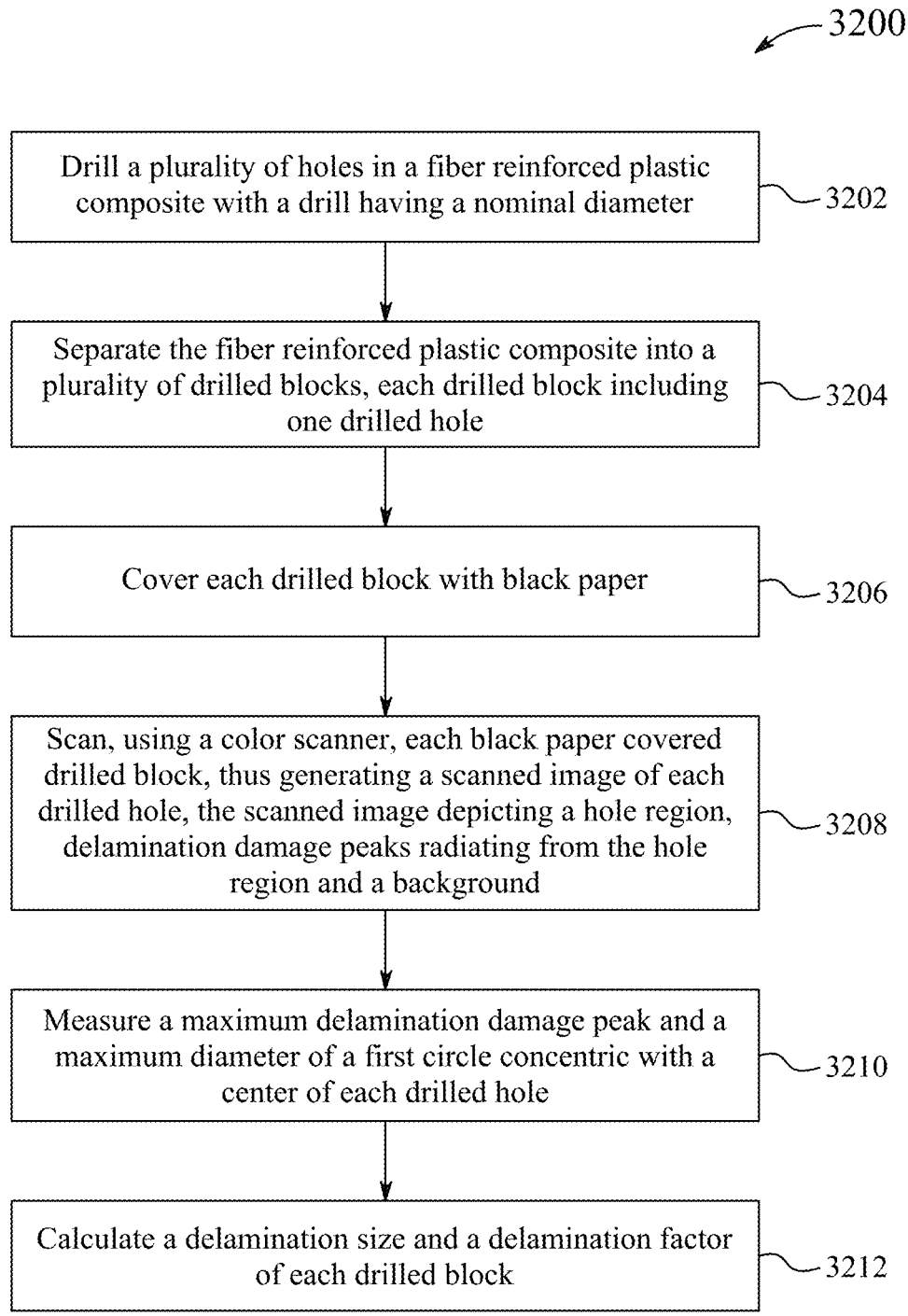
FIG. 32 is a flowchart of a method for measuring drilling damage in fiber reinforced plastic composites, according to certain embodiments.

FIG. 32 illustrates a flowchart of a method 3200 of measuring drilling damage in FRP composites. According to an aspect, at step 3202, the method 3200 includes drilling a plurality of holes in a fiber reinforced plastic composite with a drill having a nominal diameter, $D_{nom}$.

At step 3204, the method 3200 includes separating, with a cutting tool, the FRP composite into a plurality of drilled blocks 102, each drilled block 102 including one drilled hole 106.

At step 3206, the method 3200 includes covering each drilled block with the black substrate 104.

At step 3208, the method 3200 includes scanning, with the scanner 108, each drilled block 102 covered with the black substrate 104, thus generating a scanned image of each drilled hole 106. The scanned image depicts the hole region 802, a background region 804, and delamination damage peaks radiating from the hole region 806.

At step 3210, the method 3200 includes measuring, with a computing device 116, a maximum delamination damage peak and a maximum diameter $D_{max}$ of the first circle "C 1" (see FIG. 9) concentric with the center of each drilled hole 106. The maximum diameter $D_{max}$ extends through the center to the tip of the maximum delamination damage peak.

At step 3212, the method 3200 includes calculating, with the computing device 116, the delamination size, $S_d$, and the delamination factor, $F_d$, of each drilled block based on the equations (1) and (2) described above.

Although not explicitly illustrated through blocks in FIG. 27, the method 3200 further includes measuring, with the computing device 116, the radius of each delamination damage peak; sorting, with the computing device 116, the radii from largest to smallest; selecting, with the computing device 116, the delamination peaks having the three largest radii; and generating, with the computing device 116, a second circle "C2" (see FIG. 11) eccentric to the drilled hole and tangent to the delamination peaks having the three largest radii. The method 3200 further includes determining, with the computing device 116, the maximum second circle diameter, $D_{min}$, and calculating, with the computing device 116, the delamination parameter, $F_{dmin}$, based on the maximum second circle diameter, $D_{min}$, and the nominal diameter, $D_{nom}$ using the equation (3) described above.

The method 3200 further includes separating, with the computing device 116, the burr area from the delamination damage area of each scanned image of each drilled hole. In one aspect, such separation may be achieved by generating, with the computing device 116, the first traced curve by tracing the periphery of the delamination damage peaks; generating, with the computing device 116, the second traced curve by tracing the periphery of the hole 106 of each scanned image; subtracting, with the computing device 116, the background from the scanned image; determining, with the computing device 116, the delamination region by subtracting the second traced curve from the first traced curve; tracing, with the computing device 116, contours of peripheral damage within the delamination region, thus generating a plurality of third traced curves. The method 3200 further includes combining, with the computing device 116, the first traced curve with the second traced curve, thus generating the composite curve representing the delamination region of each scanned image of each drilled hole; applying, with the computing device 116, shading to the delamination region, thus generating a shaded delamination region; calculating, with the computing device 116, (i) the area, $A_{nom}$, of the first circle "C1" from the nominal diameter, $D_{nom}$, area of the shaded delamination region, $A_d$, (iii) the maximum delamination area, $A_{max}$, from the maximum diameter, $D_{max}$. The method 3200 further includes adding, with the computing device 116, the first circle "C1" back into to the shaded delamination area; identifying, with the computing device 116, burr regions radiating from the delamination region into the first circle "C 1"; determining, with the computing device 116, a radius of each burr region from a center of the first circle "C1"; calculating, with the computing device 116, each burr area from the radius of each burr region; and generating, with the computing device 116, a total burr area, $A_b$, by summing the burr areas.

The method 3200 further includes calculating, with the computing device 116, (i) the two-dimensional delamination factor, $F_a$, (ii) the adjusted delamination factor, $F_{da}$, and (iii) the equivalent delamination factor, $F_{ed}$, based on the equations (4), (5), and (6), respectively, as described above.

In an aspect, the method 3200 further includes measuring, with the computing device 116, for each of the plurality of third traced curves, a radius of a maximum periphery from the center of the first circle "C1"; calculating, with the computing device 116, for each of the plurality of third traced curves, an area of the maximum periphery from the radius of the maximum periphery and subtracting $A_{nom}$ from the area of the maximum periphery to determine a peripheral damage area; summing, with the computing device 116, the peripheral damage areas to generate a maximum peripheral damage area, $A_p$, and calculating, with the computing device 116, (i) the peripheral delamination factor, $F_p$, and (ii) the burr delamination factor, $F_b$, based on the equations (7) and (8), respectively, as described above.

According to another aspect of the present disclosure, the method 3200 includes drilling, with a drilling tool, a first set of the plurality of holes at a first feed velocity and a first drill speed; drilling, with the drilling tool, a second set of the plurality of holes at a second feed velocity and a second drill speed; recording, with a scanning electron microscopy (SEM), the first set and the second set; measuring, with the computing device 116, a burr formation and a chip formation from SEM images of the first set and the second set; comparing, with the computing device 116, the burr formation and the chip formation from the SEM images of the first set to the SEM images of the second set; determining, with the computing device 116, whether the SEM image of the first set or the SEM image of the second set has a smallest amount of burr formation and chip formation; and identifying, with the computing device 116, a feed velocity and a drill speed which gives the smallest amount of burr formation and chip formation.

In one aspect, the step of examining by the SEM may include slicing, with the cutting tool, the drilled block 102 into a plurality of SEM cross sections; depositing a 5 nm film of gold over each of the plurality of SEM cross sections by vacuum evaporation; improving a conductivity of each SEM cross section by bonding each SEM cross section to a copper support using a carbon tab; scanning each SEM cross section with the SEM to generate an SEM image; and measuring, with the computing device 116, the burr formation and chip formation of each SEM image.

According to another aspect of the present disclosure, the method 3200 includes performing, with a tensile strength tester, the tensile test on each of the plurality of drilled blocks 102 and measuring, with the tensile strength tester, the tensile modulus and a Poisson's ratio of each drilled block 102.

Performing the tensile test includes steps of attaching an aluminum tab to each corner of a drilled block; bonding a first strain gauge at the midline of the first side of the drilled block 102, where the first side is parallel to the drilled hole, and where the first strain gauge is oriented perpendicular to the drilled hole 106. The method 3200 further includes bonding a second strain gauge at the midline, wherein the second strain gauge is oriented perpendicular to the first strain gauge and parallel to the drilled hole; attaching the tensile strength tester to the aluminum tabs on a second side of the drilled block perpendicular to the first side and parallel to the drilled hole; attaching a stationary clamp to the aluminum tabs on a third side of the drilled block parallel to the second side; increasing, with the tensile strength tester, a pulling force in increments while reading a tensile stress, σ, measured by the first strain gauge and a tensile strain, ε, measured by the second strain gauge at each increment; releasing the pulling force when the drilled block fractures; and calculating, with the computing device 116, the tensile modulus, E, of the drilled block based the equation (9) described above.

The method 3200 also includes measuring, with the tensile strength tester, a first length, $L_1$, of the drilled block between the second side and the third side; measuring a change in the first length, $dl_1$, between the second side and the third side due to the pulling force at each increment; measuring a second length, $L_2$, perpendicular to the first length, LL between a fourth side and an opposite fifth side; measuring a change in the second length, $dl_2$, between the fourth side and the fifth side due to the pulling force at each increment; calculating, with the computing device 116, the longitudinal strain, and the transverse strain, $\varepsilon_t$, and the Poisson's ratio, μ, based on the equations (10), (11), (12) respectively, as described above.

According to yet another aspect, the method 3200 includes performing, with an in-plane shear tester, in-plane shear test on each of the plurality of drilled blocks 102 to measure the shear stress and the shear strain; and calculating, with the in-plane shear tester, the shear modulus, from the shear stress and the shear strain.

Performing the in-plane shear test includes steps of cutting, with the cutting tool, V-notches on the first side and the second side of the drilled block 102, such that each V-notch extends parallel to the drilled hole 106. The method 3200 further includes adhesively bonding a first strain gauge at a 45 degree angle with respect to a first midline of a third side, wherein the third side is perpendicular to the first side and parallel to the drilled hole, where the first midline is perpendicular to the drilled hole; adhesively bonding a second strain gauge along the first midline at a −45 degree angle to the first strain gauge; applying a first force, Pb, to a first corner of a first edge of the first side; applying a second force, −Pb, to a second corner of a second edge of the second side, wherein the second corner is diagonally opposite the first corner; applying a third force, PL, to a position proximal to the V notch of the first side; applying a fourth force, −PL, to a position proximal to the V notch of the second side; increasing the third force and the fourth force to a force, $P_{max}$, when the drilled block cracks; and calculating, with the computing device 116, an area, A, of the first side and shear stress, based on the equation (13) as described above, where "A" is the area of the first side.

The method 3200 further includes measuring, with the first strain gauge, a first shear strain, $\varepsilon_{-45}$, when the drilled block cracks and measuring, with the second strain gauge, a second shear strain, $\varepsilon_{+45}$, when the drilled block cracks; and calculating, with the computing device 116, the shear strain, $\gamma_{xy}$, based on the equation (14) described above.

To this end, with the developed ACIP technique, the damages are accurately outlined by very smooth digital curves, which enable the separation of the delamination and the burr areas. The enclosed areas inside the curves are calculated via, but not limited to, CorelDraw software and developed Visual Basic Macros. The developed ACIP technique has successfully measured the delamination and burr areas of the quasi-transparent and the opaque FRP composites that have acquired using color flatbed scanner, C-Scan image, and X-ray radiographic image. The results obtained from the ACIP technique match with the results obtained through other conventional methods.

Obviously, numerous modifications and variations of the present disclosure are possible in light of the above teachings. It is therefore to be understood that within the scope of the appended claims, the invention may be practiced otherwise than as specifically described herein.

The invention claimed is:

1. A method for measuring drilling damage in fiber reinforced plastic composites, comprising:
    drilling a plurality of holes in a fiber reinforced plastic composite with a drill having a nominal diameter, $D_{nom}$;
    separating, with a cutting tool, the fiber reinforced plastic composite into a plurality of drilled blocks, each drilled block including one drilled hole;
    covering each drilled block with a black substrate;
    scanning, with a scanner, each drilled block covered with the black substrate, thus generating a scanned image of each drilled hole, the scanned image depicting a hole region, delamination damage peaks radiating from the hole region and a background;
    for each scanned image:
        measuring, with a computing device, a maximum delamination damage peak;
        measuring, with the computing device, a maximum diameter $D_{max}$ of a first circle concentric with a center of each drilled hole, wherein the maximum diameter $D_{max}$ extends through the center to a tip of the maximum delamination damage peak; and
        calculating, with the computing device, a delamination size, $S_d$, based on:

$$S_d = \frac{(D_{max} - D_{nom})}{2};$$

and
   calculating, by the computing device, a delamination factor, $F_d$, of each drilled block based on:

$$F_d = \frac{D_{max}}{D_{nom}}.$$

2. The method of claim 1, further comprising:
for each scanned image:
    measuring, with a computing device, a radius of each delamination damage peak;
    sorting, with the computing device, the radii from largest to smallest;
    selecting, with the computing device, the delamination peaks having the three largest radii;
    generating, by the computing device, a second circle eccentric to the drilled hole and tangent to the delamination peaks having the three largest radii;
    determining by the computing device, a maximum second circle diameter, $D_{min}$; and
    calculating by the computing device, a delamination parameter, $F_{dmin}$, based on the maximum second circle diameter, $D_{min}$, wherein the delamination parameter, $F_{dmin}$, is given by:

$$F_{dmin} = \frac{D_{min}}{D_{nom}}.$$

3. The method of claim 1, further comprising:
separating, with the computing device, a burr area from a delamination damage area of each scanned image of each drilled hole by:
    generating, with the computing device, a first traced curve by tracing a periphery of the delamination damage peaks;
    generating, with the computing device, a second traced curve by tracing a periphery of the hole region of each scanned image;
    subtracting, with the computing device, the background from the scanned image;
    determining, with the computing device, a delamination region by subtracting the second traced curve from the first traced curve;
    tracing contours, with the computing device, of peripheral damage within the delamination region, thus generating a plurality of third traced curves;
    combining, with the computing device, the first traced curve with the second traced curve, thus generating a composite curve representing the delamination region of each scanned image of each drilled hole;
    applying, with the computing device, shading to the delamination region, thus generating a shaded delamination region;
    calculating, with the computing device, an area of the first circle, $A_{nom}$, from the nominal diameter, $D_{nom}$;
    calculating, with the computing device, an area of the shaded delamination region, $A_d$;
    calculating, with the computing device, a maximum delamination area, $A_{max}$, from the maximum diameter, $D_{max}$;
    adding, with the computing device, the first circle back into the shaded delamination area;
    identifying, with the computing device, burr regions radiating from the delamination region into the third circle;
    determining, with the computing device, a radius of each burr region from a center of the first circle;

calculating, with the computing device, each burr area from the radius of each burr region; and generating, with the computing device, a total burr area, $A_b$, by summing the burr areas.

4. The method of claim 3, further comprising:

calculating, with the computing device, a two-dimensional delamination factor, Fa, based on:

$$F_a = \frac{A_d}{A_{nom}}.$$

5. The method of claim 3, further comprising:

calculating, with the computing device, an adjusted delamination factor, $F_{da}$, based on:

$$F_{da} = F_d + \frac{A_d(F_d^2 - Fd)}{A_{max} - A_{nom}}.$$

6. The method of claim 3, further comprising:

calculating, with the computing device, an equivalent delamination factor, $F_{ed}$, based on:

$$F_{ed} = \frac{1}{D_{nom}} + \sqrt{\left(\frac{4(A_d + A_{nom})}{\pi}\right)}.$$

7. The method of claim 3, further comprising:

measuring, with the computing device, for each of the plurality of third traced curves, a radius of a maximum periphery from the center of the first circle, $A_{nom}$;

calculating, with the computing device, for each of the plurality of third traced curves, an area of the maximum periphery from the radius of the maximum periphery and subtracting $A_{nom}$ from the area of the maximum periphery to determine a peripheral damage area;

summing, with the computing device, the peripheral damage areas to generate a maximum peripheral damage area, $A_p$; and calculating, with the computing device, a peripheral delamination factor, $F_p$, based on:

$$F_p = \frac{A_b}{A_{nom}}.$$

8. The method of claim 7, further comprising:

calculating, with the computing device, a burr delamination factor, $F_b$, based on:

$$F_b = \frac{A_b}{A_{nom}}.$$

9. The method of claim 1, further comprising:

drilling, with the drilling tool, a first set of the plurality of holes at a first feed velocity and a first drill speed;

drilling, with the drilling tool, a second set of the plurality of holes at a second feed velocity and a second drill speed;

recording, with a scanning electron microscope (SEM), SEM images of the first set;

measuring, with the computing device, a burr formation and a chip formation of the SEM images of the first set;

recording, with the SEM, SEM images of the second set;

measuring, with the computing device, the burr formation and the chip formation of the SEM images of the second set;

comparing, with the computing device, the burr formation and the chip formation of the SEM images of the first set to the SEM images of the second set;

determining, with the computing device, whether the SEM images of the first set or the SEM images of the second set has the smallest amount of burr formation and chip formation; and identifying, with the computing device, the feed velocity and drill speed which gives the smallest amount of burr formation and chip formation.

10. The method of claim 9, wherein recording images by the SEM comprises:

slicing, with the cutting tool, a drilled block into a plurality of SEM cross sections;

depositing a 5 nm film of gold over each of the plurality of SEM cross sections by vacuum evaporation;

improving a conductivity of each SEM cross section by bonding each SEM cross section to a copper support using a carbon tab;

scanning each SEM cross section with the SEM to generate an SEM image; and measuring, with the computing device, the burr formation and chip formation of each SEM image.

11. The method of claim 1, further comprising:

performing, with a tensile strength tester, a tensile test on each of the plurality of drilled blocks; and measuring, with the tensile strength tester, a tensile modulus and a Poisson's ratio of each drilled block.

12. The method of claim 11, wherein performing a tensile test on each of the plurality of drilled blocks comprises:

attaching an aluminum tab to each corner of a drilled block;

bonding a first strain gauge at a midline of a first side of the drilled block, wherein the first side is parallel to the drilled hole, wherein the first strain gauge is oriented perpendicular to the drilled hole;

bonding a second strain gauge at the midline, wherein the second strain gauge is oriented perpendicular to the first strain gauge and parallel to the drilled hole;

attaching the tensile strength tester to the aluminum tabs on a second side of the drilled block perpendicular to the first side and parallel to the drilled hole;

attaching a stationary clamp to the aluminum tabs on a third side of the drilled block parallel to the second side;

increasing, with the tensile strength tester, a pulling force in increments while reading a tensile stress, $\sigma$, measured by the first strain gauge and a tensile strain, $\varepsilon$, measured by the second strain gauge at each increment;

releasing the pulling force when the drilled block fractures; and calculating, with the computing device, the tensile modulus, E, of the drilled block based on:

$$E = \frac{\sigma}{\varepsilon}.$$

13. The method of claim 12, further comprising:
measuring, with the tensile strength tester, a first length, $L_1$, of the drilled block between the second side and the third side;
measuring a change in the first length, $dl_1$, between the second side and the third side due to the pulling force at each increment;
measuring a second length, $L_2$, the perpendicular to the first length, LL between a fourth side and an opposite fifth side;
measuring a change in the second length, $dl_2$, between the fourth side and the fifth side due to the pulling force at each increment;
calculating, with the computing device, a longitudinal strain, $\varepsilon_l$, based on:

$$\varepsilon_l = \frac{dl_1}{L_1};$$

calculating, with the computing device, a transverse strain, $\varepsilon_t$, based on:

$$\varepsilon_t = \frac{dl_2}{L_2};$$

and
calculating, with the computing device, the Poisson's ratio, $\mu$, based on:

$$\mu = -\frac{\varepsilon_t}{\varepsilon_l}.$$

14. The method of claim 1, further comprising:
performing, with an in-plane shear tester, an in-plane shear test on each of the plurality of drilled blocks to measure a shear stress and a shear strain; and
calculating, with the computing device, a shear modulus, $G_{xy}$, from the shear stress and the shear strain.

15. The method of claim 14, wherein performing an in-plane shear test on a drilled block comprises:
cutting, with the cutting tool, V-notches at a first side and a second side of the drilled block;
adhesively bonding a first strain gauge at a 45 degree angle with respect to a first midline of a third side, wherein the third side is perpendicular to the first side, wherein the first midline is perpendicular to the drilled hole;
adhesively bonding a second strain gauge along the first midline at a −45 degree angle to the first strain gauge;
applying a first force, Pb, to a first corner of a first edge of the first side;
applying a second force, −Pb, to a second corner of a second edge of the second side, wherein the second corner is diagonally opposite the first corner;
applying a third force, PL, to a position proximal to the V notch of the first side;
applying a fourth force, −PL, to a position proximal to the V notch of the second side;
increasing the third force and the fourth force to a force, $P_{max}$, when the block cracks;
calculating, with the computing device, an area, A, of the first side;
calculating, with the computing device, the shear stress, $\tau_{xy}$, based on:

$$\tau_{xy} = \frac{P_{max}}{A}.$$

16. The method of claim 15, wherein performing an in-plane shear test on a drilled block further comprises:
measuring, with the first strain gauge, a first strain, $\varepsilon_{-45}$, when the block cracks;
measuring, with the second strain gauge, a shear strain, $\varepsilon_{+45}$, when the block cracks;
calculating, with the computing device, the shear strain, $\gamma_{xy}$, based on:

$$\gamma_{xy} = \varepsilon_{-45} - \varepsilon_{+45}.$$

17. A system for measuring drilling damage in fiber reinforced plastic composites, comprising:
a plurality of blocks, each block having a drilled hole;
a plurality of black substrates, each black substrate covering one side of a face of a block over the drilled hole;
a scanner configured to scan the one side of each block covered by the black substrate and generate a scanned image, wherein the scanned image depicts a hole region, delamination damage peaks radiating from the hole region and a background region;
a computing device that includes circuitry and a memory storing program instructions, which include drawing software, in which the program instructions, when executed by one or more processors, are configured to:
measure a maximum delamination damage peak;
measure a maximum diameter $D_{max}$ of a first circle concentric with a center of each drilled hole, where the maximum diameter $D_{max}$ extends through the center to a tip of the maximum delamination damage peak; and
calculate a delamination size, $S_d$, based on:

$$S_d = \frac{(D_{max} - D_{nom})}{2};$$

calculate a delamination factor, $F_d$, of each drilled block based on:

$$F_d = \frac{D_{max}}{D_{nom}};$$

measure the radius of each delamination damage peak;
sort the radii from largest to smallest;
select the delamination peaks having the three largest radii;
generate a second circle eccentric to the drilled hole and tangent to the delamination peaks having the three largest radii;
determine a maximum second circle diameter, $D_{min}$; and
calculate a delamination parameter, $F_{dmin}$, based on the maximum second circle diameter, $D_{min}$, wherein the delamination parameter, $F_{dmin}$, is given by:

$$F_{dmin} = \frac{D_{min}}{D_{nom}}.$$

18. The system of claim 17, wherein the computing device is further configured to:
- separate a burr area from a delamination damage area of each scanned image of each drilled hole by:
  - generating a first traced curve by tracing a periphery of the delamination damage peaks;
  - generating a second traced curve by tracing a periphery of the hole region of each scanned image;
  - subtracting the background region from the scanned image;
  - determining a delamination region by subtracting the second traced curve from the first traced curve;
  - tracing contours of peripheral damage within the delamination region, thus generating a plurality of third traced curves;
  - combining the first traced curve with the second traced curve, thus generating a composite curve representing the delamination region of each scanned image of each drilled hole;
  - applying shading to the delamination region, thus generating a shaded delamination region;
- calculate an area of a third circle, $A_{nom}$, from the nominal diameter, $D_{nom}$;
- calculate an area of the shaded delamination region, $A_d$;
- calculate a maximum delamination area, $A_{max}$, from the maximum diameter, $D_{max}$;
- add the third circle to the shaded delamination area;
- identify burr regions radiating from the delamination region into the third circle;
- determine a radius of each burr region from a center of the third circle;
- calculate each burr area from the radius of each burr region;
- generate a total burr area, $A_b$, by summing the burr areas;
- calculate a two-dimensional delamination factor, Fa, based on:

$$F_a = \frac{A_d}{A_{nom}};$$

calculate an adjusted delamination factor, $F_{da}$, based on:

$$F_{da} = F_d + \frac{A_d(F_d^2 - Fd)}{A_{max} - A_{nom}};$$

measure, for each of the plurality third traced curves, a radius of a maximum periphery from a center of the third circle:
calculate, for each of the plurality third traced curves, an area of the maximum periphery from the radius of the maximum periphery and subtracting $A_{nom}$ from the area of the maximum periphery to determine a peripheral damage area;

sum the peripheral damage areas to generate a maximum peripheral damage area, $A_p$;
calculate a peripheral delamination factor, $F_p$, based on:

$$F_p = \frac{A_b}{A_{nom}};$$

and
calculate a burr delamination factor, $F_b$, based on:

$$F_b = \frac{A_b}{A_{nom}}.$$

19. The system of claim 17, further comprising:
- a scanning electron microscope (SEM) connected to the computing device, wherein the scanning electron microscope is configured to scan a cross section each drilled block and generate an SEM image;
- wherein the computing device and drawing software is further configured to measure the burr formation and chip formation of each SEM image;
- a tensile strength tester connected to the computing device, the tensile strength tester configured to measure a tensile modulus and a Poisson's ratio of each block; and
- an in-plane shear tester, connected to the computing device, the in-plane shear tester including strain gauges configured to measure a stress and a strain of each block upon application of a breaking force, wherein the computing device is configured to calculate a shear modulus, Gxy, a shear stress and a shear strain from the stress and the strain measured when the block cracks.

20. A method for determining a feed velocity and a drilling speed for drilling holes in fiber reinforced plastic composites, comprising:
- drilling, with a drilling tool, a first set of a plurality of holes at a first feed velocity and a first drill speed;
- drilling, with the drilling tool, a second set of a plurality of holes at a second feed velocity and a second drill speed;
- measuring, with a computing device, a burr formation and a chip formation of the first set;
- measuring, with the computing device, a burr formation and a chip formation of the second set;
- comparing, with the computing device, the burr formation and chip formation of the first set to the second set;
- determining, with the computing device, whether the first set or the second set has the smallest amount of burr formation and chip formation; and
- identifying, with the computing device, the feed velocity and drill speed which gives the smallest amount of burr formation and chip formation.

* * * * *